United States Patent [19]

Johnson et al.

[11] Patent Number: 5,380,721
[45] Date of Patent: Jan. 10, 1995

[54] ARYL-FUSED AND HETARYL-FUSED-2,4-DIAZEPINE AND 2,4-DIAZOCINE ANTIARRHYTHMIC AGENTS

[75] Inventors: Robert E. Johnson, East Greenbush; Donald C. Schlegel, Schodack; Alan M. Ezrin, Colonie, all of N.Y.

[73] Assignee: Sterling Winthrop Inc., New York, N.Y.

[21] Appl. No.: 250,995

[22] Filed: May 31, 1994

Related U.S. Application Data

[63] Continuation of Ser. No. 21,926, Feb. 24, 1993, abandoned, which is a continuation-in-part of Ser. No. 974,396, Nov. 10, 1992, abandoned, which is a continuation-in-part of Ser. No. 743,853, Jun. 13, 1991, abandoned, which is a continuation-in-part of Ser. No. 580,065, Sep. 10, 1990, abandoned.

[51] Int. Cl.$^6$ .............. C07D 243/04; C07D 245/06; A61K 31/395; A61K 31/55
[52] U.S. Cl. .................... 514/183; 514/221; 540/473; 540/557; 540/558; 540/561; 540/567; 540/568; 564/207; 564/306; 564/388
[58] Field of Search ............... 540/473, 567; 514/183, 514/221

U.S. PATENT DOCUMENTS

| | | | |
|---|---|---|---|
| 3,696,093 | 10/1972 | Rodriguez, H.R. et al. | 260/239 |
| 4,840,948 | 6/1989 | Láng, T. et al. | 514/221 |
| 4,325,957 | 4/1982 | Zeugner et al. | 424/263 |
| 4,382,030 | 5/1983 | Zeugner et al. | 260/239 |

FOREIGN PATENT DOCUMENTS

| | | |
|---|---|---|
| 59-13766 | 1/1984 | Japan . |
| 389765 | 10/1990 | EPO . |
| 1183135 | 3/1970 | United Kingdom . |
| 11770135 | 9/1971 | West Germany . |
| 66303 | 12/1982 | EPO . |

OTHER DOCUMENTS

Elslager, E.F. et al. "The synthesis of 5,10-dihydro- and 2,3,5,10-tetrahydrothiazolo-[3,2-b] [2,4]benzodiazepines, 1,2,3,4,7,12-hexahydrobenzothiazolo-[3,2-b] [2,4]benzodiazepine, and 9,14-dihydro-6H-[1] benzothiopyrano-[4',3':4, 5] thiazolo[3,2-b] [2,4]benzodiazepine via 1,2,4,5-tetrahydro-3H-2,4-benzodiazepine-3-thione", J. Het. Chem. 5:609–613, 1968.

Primary Examiner—John M. Ford
Assistant Examiner—Philip I. Datlow
Attorney, Agent, or Firm—Michael D. Alexander; Paul E. Dupont

[57] ABSTRACT

Aryl-fused- and hetaryl-fused-2,4-diazepines of formula XXXVI, benzodiazocines of formula XXX, benzodiazepines of formula II

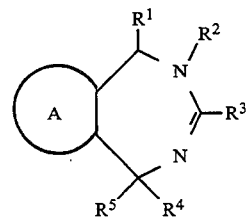

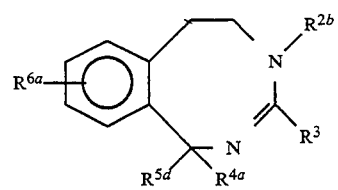

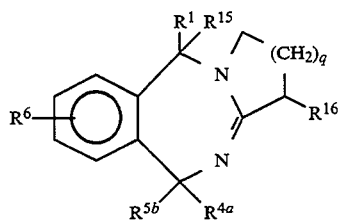

δ-aminoamides of formula III and aryldimethanamines of formula XXXVII

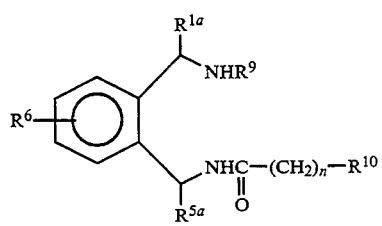

(Abstract continued on next page.)

ABSTRACT—Continued

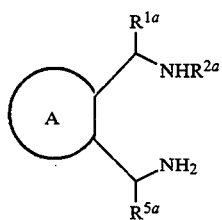

XXXVII wherein
A is an aryl or hetaryl ring;
$R^1$ is hydrogen, alkyl, aryl or hetaryl;
$R^2$ is hydrogen, alkyl, substituted alkyl, or aryl;
$R^3$ is alkyl, aryl, aralkyl or heteroatom substituted alkyl or aralkyl;
$R^4$ is hydrogen or alkyl;
$R^5$ is hydrogen, alkyl, aryl or hetaryl;
$R^6$ is hydrogen, alkyl, alkoxy, halogen or a fused benzene ring;
$R^9$ is hydrogen, alkyl, or substituted alkyl; and
$R^{10}$ is hydrogen, alkyl, or substituted alkyl.

The invention further relates to processes for the preparation of, pharmaceutical compositions containing, and methods of treating cardiac arrhythmia with the compounds of formulas XXXVI, XXX, II, III, and XXXVII.

60 Claims, No Drawings

ARYL-FUSED AND HETARYL-FUSED-2,4-DIAZEPINE AND 2,4-DIAZOCINE ANTIARRHYTHMIC AGENTS

CROSS REFERENCE TO RELATED APPLICATIONS

This application is a continuation of our prior copending application Ser. No. 08/021,926, filed Feb. 24, 1993, now abandoned, which in turn is a continuation-in-part of our prior copending application Ser. No. 07/974,396, filed Nov. 10, 1992, now abandoned, which in turn is a continuation-in-part of our prior copending application Ser. No. 07/743853, filed Jun. 13, 1991, now abandoned, which in turn is a continuation-in-part of our prior copending application Ser. No. 07/580065, filed Sep. 10, 1990, now abandoned.

BACKGROUND OF THE INVENTION

FIELD OF THE INVENTION

The present invention relates to novel 4,5-dihydro-1H-2,4-aryl fused diazepines, and benzodiazocines to related diamines and aminoamides, to processes for preparing them and to methods and compositions for treating cardiac arrhythmias in mammals utilizing said 4,5-dihydro-1H-2,4-benzodiazepines, and diazocines.

INFORMATION DISCLOSURE STATEMENT

U.S. Pat. No. 3,696,093 to Rodriguez et al. discloses a single 3,4-disubstituted benzodiazepine: 3,4-dimethyl-4,5-dihydro-1H-2,4-benzodiazepine hydrochloride.

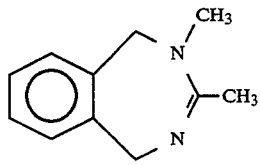

Also disclosed are 4,5-dihydro-1H-2,4-benzodiazepines monosubstituted in the 3 position with benzyl, dimethylaminoethyl, amino, 1-piperidinylmethyl, and phenyl. The compounds are said to be useful as cardiovascular agents, for example, in the treatment or management of the various forms of hypertension or of congestive heart failure. The patent does not disclose antiarrhythmic properties for the genus, and the single example of a disubstituted benzodiazepine was found to be inactive as an antiarrhythmic when tested in the protocol used to evaluate the compounds of the present invention.

Japanese application 59/013766 (CA 101:23612m) discloses a series of 1,2,4-trisubstituted-tetrahydrobenzodiazepines of general structure

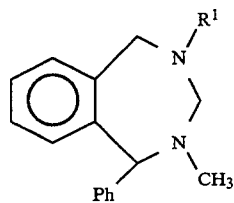

wherein $R^1$ is lower alkyl or phenethyl (opt. substd. with lower alkoxy). The compounds are said to be analgesics.

Elslager et al [J. Het. Chem. 5, 609–613 (1968)] describe the synthesis of a series of tetrahydrothiazolo-[3,2-b][2,4] benzodiazepines. The authors state that "None of the compounds possessed appreciable biological activity." As intermediates in the synthesis, they disclose

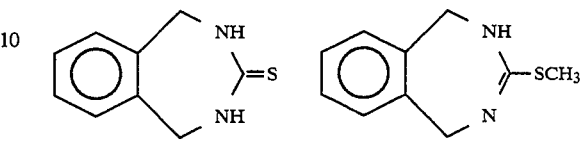

1,2,4,5-tetrahydro-3H-2,4-benzodiazepine-3-thione and 2,5,dihydro-3-(methylthio)-1H-2,4-benzodiazepine hydroiodide.

U.S. Pat. No. 4,840,948 to Lang et al. discloses a series of 1-(hydroxystyryl)-5H-2,3-benzodiazepines of general formula:

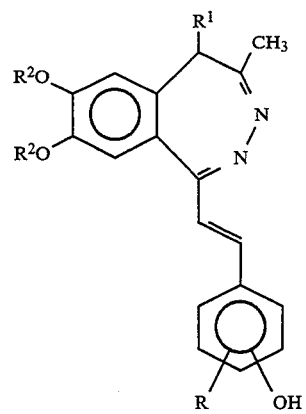

wherein
R stands for a hydrogen or halogen atom, or a $C_{1-4}$ alkoxy group,
$R^1$ represents a hydrogen atom or a $C_{1-4}$ alkyl group,
$R^2$ and $R^3$ are identical and denote a $C_{1-4}$ alkyl group, or combined they denote a methylene group.

The compounds are said to be positive inotropes and therefore useful as cardiotonics.

Carr et al., European Patent Application 389765, published Oct. 30, 1990, disclose compounds of the formula:

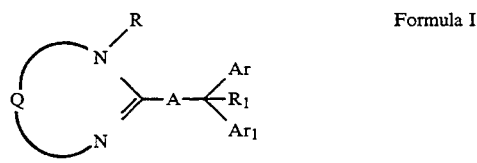

Formula I in which Q is represented by a substituent selected from the group consisting of $(CH_2)_n$ in which n is an integer from 2–10,

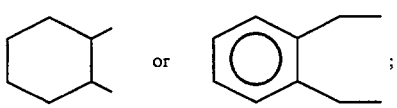

A is a substituent selected from the group consisting of —NH—(CH$_2$)$_m$ in which m is an integer from 0–5, a piperidino substituent, or a piperazino substituent; both Ar and Ar$_1$ are each independently represented by a phenyl ring each of which may be optionally substituted with up to 3 substituents, each selected from the group consisting of halogen, C$_{1-4}$ alkyl, C$_{1-4}$ alkoxy, hydroxy, and trifluoromethyl; and R is represented by hydrogen or C$_{1-4}$ alkyl; R$_1$ is represented by hydrogen or C$_{1-4}$ alkyl; the optical isomers and tautomers thereof; and the pharmaceutically acceptable acid addition salts thereof; with the provisos that: 1) when Q is represented by (CH$_2$)$_{2,3}$ or 4, then A is not represented by NH—(CH$_2$)$_o$; and 2) when Q is represented by (CH$_2$)$_2$ and R is a C$_{1-4}$ alkyl; then A is not NH—(CH$_2$). The compounds are said to be useful as calcium antagonists and thus to be useful in the treatment of a variety of disease states, for example, cardiac arrhythmias, angina, depression, hypertension, epilepsy and mania.

Rodriquez and Stevens, GB 1183135, published Mar. 4, 1970, disclose 4,5-dihydro-1H-2,4-benzodiazepines of the formula:

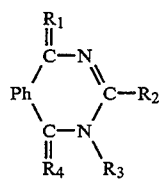

in which Ph represents an optionally substituted 1,2-phenylene group, R$_1$ and R$_4$ (which may be the same or different) each represents two hydrogen atoms or two aliphatic groups, or a hydrogen atom together with an aliphatic group, an araliphatic group, an aromatic group, a heterocyclic group of aromatic characteristics or a heterocyclic-aliphatic group, in which the heterocyclic portion has aromatic characteristics; R$_2$ represents a hydrogen atom, a hydroxy group, a mercapto group, an optionally substituted amino group, an aliphatic group, an araliphatic group, an aromatic group, a heterocyclic group of aromatic characteristics or a heterocyclic-aliphatic group, in which the heterocyclic portion has aromatic characteristics; and R$_3$ represents a hydrogen atom, an aliphatic group, an araliphatic group, an aromatic group, a heterocyclic group of aromatic characteristics or a heterocyclic-aliphatic group, in which the heterocyclic portion has aromatic characteristics, or the acyl group of a carboxylic acid; N-oxides, quaternary derivatives and salts thereof. The compounds are said to be useful as cardiovascular agents, for example, in the treatment of congestive heart failure; and as coccidiostatic or CNS-stimulating agents. A substantially similar disclosure can be found in Rodriquez and Stevens, DE 11770135, published Sep. 23, 1971.

Zeugner et al., European Patent Application 66303, published Dec. 8, 1982, disclose compounds of the formula:

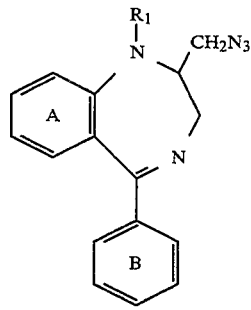

wherein R$_1$ is H or lower-alkyl; rings A and B have 0–3 substituents selected from halogen, lower-alkylthio, lower-alkoxy, lower-alkyl, OH, NO$_2$ and CF$_3$, or a methylenedioxy or ethylenedioxy group attached to 2 adjacent C atoms. The compounds are said to be useful as intermediates and to have sedative, broncholytic and antiarrhythmic activity.

Zeugner et al., U.S. Pat. No. 4,325,957, issued Apr. 20, 1982, disclose compounds of the formula:

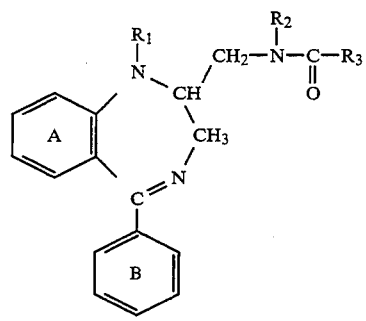

wherein

R$_1$ represents hydrogen, lower alkyl, lower alkenyl or cyclopropylmethyl,

R$_2$ represents hydrogen, lower alkyl or lower alkenyl,

R$_3$ represents a group of the formula a, b, c, or d

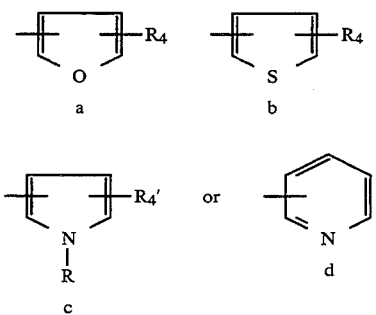

wherein R is hydrogen or C$_1$–C$_3$-alkyl, R$_4$ is hydrogen, lower alkyl, lower alkoxy, nitro or halogen, in particular chlorine or bromine, and R$_4'$ is hydrogen or C$_1$–C$_4$-alkyl, and the aromatic groups A and B independently from each other each may be unsubstituted or be substituted by 1 to 3 substituents selected from the group consisting of halogen, lower alkythio, lower alkoxy, lower alkyl, hydroxy, nitro and trifluoromethyl, or be substituted at two adjacent carbon atoms by methylenedioxy or ethylenedioxy, and optical isomers and pharmaceutically-acceptable acid addition salts thereof. The compounds are said to exhibit pscho pharmacological, diuretic, antiarrhythmic and analgesic activities. A substantially similar disclosure can be found in Zeugner et al., U.S. Pat. No. 4,382,030, issued May 3, 1983, which is a divisional of U.S. Pat. No. 4,325,957.

SUMMARY OF THE INVENTION

In a product aspect, the invention relates to compounds of the formula XXXVI:

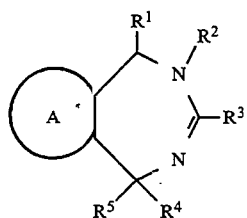

wherein

A is a ring chosen from the group consisting of phenyl, thienyl, furanyl, naphthyl, pyridinyl, cyclohexyl and phenyl having one or two substituents chosen from the group consisting of amino, lower-alkyl, lower-alkoxy, halogen, nitro, and lower-alkylsulfonamido;

$R^1$ is hydrogen, lower-alkyl, benzyl, naphthyl, thienyl, pyridinyl, phenyl, or phenyl having one or two substituents chosen from the group consisting of lower-alkyl and lower-alkoxy;

$R^2$ is hydrogen; lower-alkyl; benzyl; phenyl; phenyl substituted with halogen, lower-alkyl or lower-alkoxy; or $R^2$ is —CH$_2$CH$_2$R$^7$ where R$^7$ is lower-alkoxy; benzyl; di-(lower-alkyl) amino, pyrrolidino; piperidino; morpholino; pyridinyl; phenyl; or phenyl substituted with amino, nitro or lower-alkyl-sulfonamido;

$R^3$ is $Y_p$—(CH$_2$)$_m$—X$_n$—R$^8$ wherein
Y is —NH—, —O—, —S—, or

p is zero or one;
m is an integer from zero to seven;
X is —S—, —O—, —SO$_2$—,

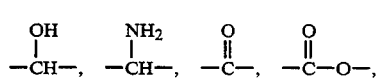

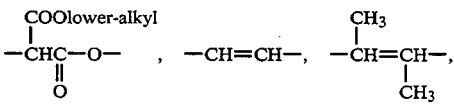

or —NHSO$_2$—;
n is zero or one; and $R^8$ is hydrogen; lower-alkyl; phenyl; furanyl; thienyl; pyridinyl; phenyl having one or two substituents chosen independently from the group consisting of halogen, lower-alkyl, nitro, hydroxy, lower-alkoxy, lower-alkylamido, lower-alkylsulfonamido polyfluorolower-alkylsulfonamido, lower-alkylaminosulfonyl, dilower-alkylaminosulfonyl, and amino; or when n is zero and m is other than zero, R$^8$ is additionally halogen; benzyl(lower-alkyl)amino; di-(lower-alkyl)amino; or a 5- or 6-membered heterocycle containing one or two nitrogens, said heterocycle being unsubstituted or substituted with one lower-alkyl group; or X and R$^8$ taken together are cyclohexylidine;

$R^4$ is hydrogen; lower-alkyl; allyl; lower-alkoxy-lower-alkyl; acetyl; lower-alkylaceto; lower-alkyl carboxyl; or α-hydroxy-lower-alkyl; and $R^5$ is hydrogen; lower-alkyl; naphthyl; thienyl; pyridinyl; benzyl; phenyl; or phenyl having one or two substituents chosen independently from the group consisting of lower-alkyl, lower-alkoxy, halogen, hydroxyl, amino, di-(lower-alkyl)amino, lower-alkylsulfonamido, lower-acylamino, lower-alkylthio, and lower-alkylsulfonyl;

or an acid-addition salt thereof;
with the proviso that the total number of carbon atoms in R$^1$ plus R$^2$ plus R$^4$ plus R$^5$ must be five or greater.

The compounds of formula XXXVI are useful as antiarrhythmic agents.

Among the compounds within the ambit of Formula XXXVI above are those wherein:

A, R$^1$, and R$^4$ are as defined hereinabove and
R$^2$ is hydrogen; lower-alkyl; benzyl; phenyl; phenyl substituted with halogen, lower-alkyl or lower-alkoxy; or R$^2$ is —CH$_2$CH$_2$R$^7$ where R$^7$ is lower-alkoxy; benzyl; di-(lower-alkyl)amino, pyrrolidino; piperidino; morpholino; phenyl; or phenyl substituted with amino, nitro or lower-alkyl sulfonamido;

R$^3$ is $Y_p$—(CH$_2$)$_m$—X$_n$—R$^8$ wherein
Y is —NH—, —O—, —S—, or

p is zero or one;
m is an integer from zero to seven;
X is —S—, —O—, —SO$_2$—,

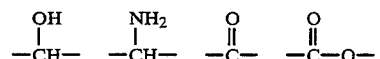

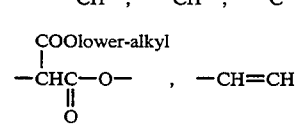

n is zero or one; and
R$^8$ is hydrogen; lower-alkyl; phenyl; furanyl; thienyl; pyridinyl; phenyl having one or two substituents chosen independently from the group consisting of halogen, lower-alkyl, nitro, hydroxy, lower-alkoxy, lower-alkylamido, lower-alkylsulfonamido dilower-alkylaminosulfonyl, and amino; or when n is zero and m is other than zero, R$^8$ is additionally halogen; benzyl(lower-alkyl)amino; di-(lower-alkyl)amino; or a 5- or 6-membered heterocycle containing one or two nitrogens, said heterocycle being unsubstituted or substituted with one lower-alkyl group; or X and $R^8$ taken together are cyclohexylidine; and $R^5$ is hydrogen; lower-alkyl; naphthyl; thienyl; pyridinyl; benzyl; phenyl; or phenyl having one or two substituents chosen independently from the group consisting of lower-alkyl, lower-alkoxy, halogen, hydroxyl, amino, di-(lower-alkyl)amino, lower-alkylsulfonamido, and lower-acylamino;

or an acid-addition salt thereof;

with the proviso that the total number of carbon atoms in $R^1$ plus $R^2$ plus $R^4$ plus $R^5$ must be five or greater.

Lower-alkyl as used herein describes linear, branched, or cyclic saturated carbon chains of eight or fewer carbon atoms; lower-alkoxy as used herein describes linear or branched alkyloxy substituents containing eight or fewer carbon atoms; halogen describes bromine, chlorine or fluorine.

In the text that follows, the substituents R are defined when initially presented and maintain that definition whenever they occur subsequently.

In a further product aspect, the invention relates to compounds of the formula II

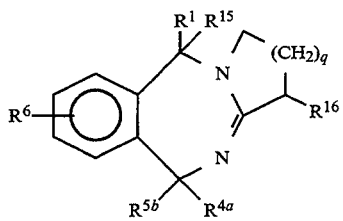

wherein $R^{4a}$ is hydrogen or lower-alkyl;

$R^{5b}$ is hydrogen; lower-alkyl; phenyl; phenyl having one or two substituents chosen from the group consisting of lower-alkyl, lower-alkoxy, and halogen; naphthyl; thienyl; pyridinyl; or benzyl;

$R^6$ is one or two substituents chosen independently from the group consisting of hydrogen, lower-alkyl, lower-alkoxy, halogen, nitro, and lower-alkylsulfonamido; or $R^6$ is a fused benzene ring;

$R^{15}$ is hydrogen or, when $R^1$ is phenyl, $R^{15}$ may additionally be lower-alkyl;

$R^{16}$ is $(CH_2)_m$—$(X^a)_n$—$R^{8a}$;

m is an integer from zero to seven;

$X^a$ is —S—, —$SO_2$—, —O—, or —CH=CH—;

n is zero or one;

$R^{8a}$ is hydrogen; lower-alkyl; phenyl; or phenyl having one or two substituents chosen from the group consisting of lower-alkyl;

lower-alkoxy, and halogen; and q is one or two; or an acid addition salt thereof.

The compounds of formula II are useful as antiarrhythmic agents.

In a further product aspect, the invention relates to compounds of formula XXX

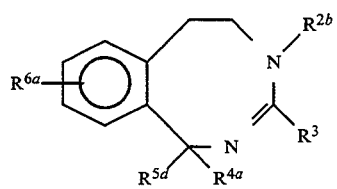

wherein $R^{2b}$ is hydrogen; lower-alkyl; di(lower-alkyl)aminoalkyl; phenyl; phenethyl or phenyl substituted with halogen, lower-alkyl or lower-alkoxy;

$R^{5d}$ is lower-alkyl; phenyl; naphthyl; thienyl; pyridinyl; benzyl; or phenyl having one or two substituents chosen from the group consisting of lower-alkyl, lower-alkoxy and halogen;

$R^{6a}$ is one or two substituents chosen independently from the group consisting of hydrogen, lower-alkyl, lower-alkoxy and halogen; or an acid-addition salt thereof.

The compounds of formula XXX are useful as antiarrhythmic agents.

In a further product aspect, the invention relates to compounds of formula III

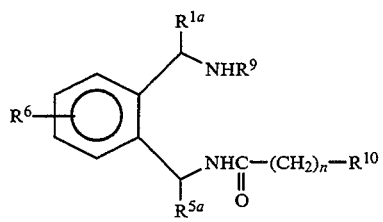

wherein $R^{1a}$ is hydrogen, lower-alkyl or phenyl;

$R^{5a}$ is hydrogen; phenyl; phenyl having one or two substituents chosen from the group consisting of halogen, lower-alkyl and lower-alkoxy; naphthyl; thienyl; pyridinyl; or benzyl;

$R^9$ is hydrogen, lower-alkyl, benzyl, phenethyl or [di-(lower-alkyl)amino]lower-alkyl;

$R^{10}$ is hydrogen; lower-alkyl; phenyl; phenyl substituted with halogen, lower-alkyl, lower-alkylsulfonamido or lower-alkoxy; phenoxy; phenoxy substituted with halogen, lower-alkyl or lower-alkoxy; benzyl; or $R^{10}$ is a 5- or 6-membered heterocycle containing one or two nitrogens; and n is zero or one; or an acid-addition salt thereof.

The compounds of formula III are all useful as intermediates in the synthesis of compounds of formula I (see below) and are useful as antiarrhythmic agents as well.

In a further product aspect, the invention relates to compounds of formula XXXVII

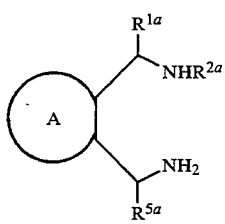

wherein $R^{2a}$ is lower-alkyl; benzyl; phenyl; phenyl substituted with halogen, lower-alkyl or lower-alkoxy; or $R^{2a}$ is —$CH_2CH_2R^7$ where $R^7$ is lower-alkoxy, phenyl, benzyl, di(lower-alkyl)amino, pyrrolidino, piperidino, or morpholino; and at least one of $R^{1a}$ and $R^{5a}$ is phenyl, substituted phenyl, benzyl, naphthyl, thienyl or pyridinyl; or an acid-addition salt thereof.

The compounds of formula XXXVII are useful as intermediates in the synthesis of compounds of formula XXXVI and are useful as antiarrhythmic agents as well.

In a further product aspect, the invention relates to compounds of formula XXXII or acid-addition salts thereof.

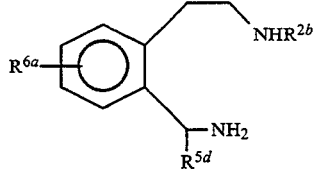

XXXII

The compounds are useful as intermediates in the synthesis of compounds of formula XXX.

In a process aspect, the invention relates to processes for the production of benzodiazepines of formula V

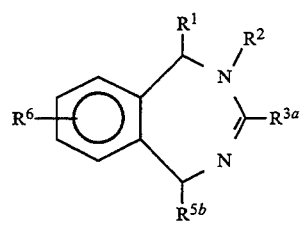

V wherein
R$^{3a}$ is (Y$^a$)$_p$—(CH$_2$)$_m$—(X$^a$)$_n$—R$^8$ wherein
Y$^a$ is —O—, —S— or $$-\overset{CH_3}{\underset{|}{CH}}-;$$

and
X$^a$ is —S—, —SO$_2$—, —O— or —CH=CH—;
by the condensation of diamines of formula VId

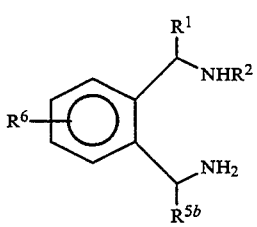

VId with iminoethers of formula R$^{3a}$C(OR$^{12}$)NH, wherein R$^{12}$ is methyl or ethyl, with orthoesters of formula R$^{3a}$C(OR$^{12}$)$_3$ or with esters of formula R$^{3a}$COOR$^{12}$.

In a further process aspect the invention relates to a process for producing a compound of formula V

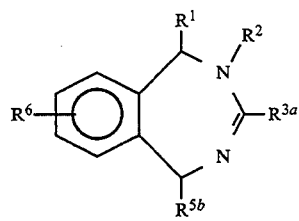

V which comprises reacting a compound of formula XXVII or XXVIII with a trialkylaluminum.

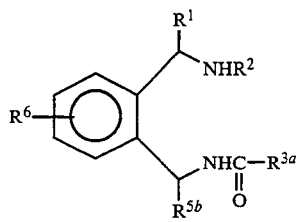

XXVII or

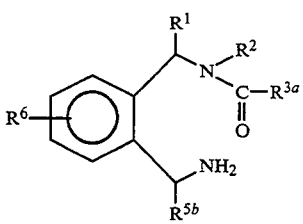

XXVIII

In a further process aspect, the invention relates to a process for preparing a compound of formula Ia

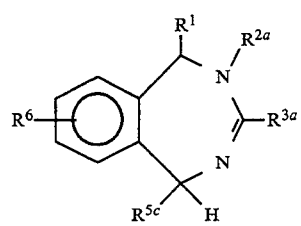

Ia wherein
R$^{4b}$ is lower-alkyl, allyl, lower-alkoxylower-alkyl, acetyl, lower-alkylaceto, lower-alkoxycarbonyl, or α-hydroxyloweralkyl; and
R$^{5c}$ is phenyl; phenyl having one or two substituents chosen from the group consisting of lower-alkyl, lower-alkoxy and halogen; naphthyl; thienyl; or pyridinyl;
which comprises reacting a compound of formula Va

Va with a strong base and then with a suitable electrophile.

In a further process aspect, the invention relates to a process for preparing a compound of formula VII

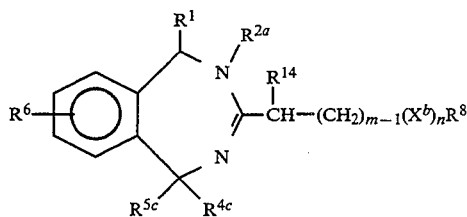

wherein
$X^b$ is —S—, —SO$_2$—, —O—, —CH=CH—,

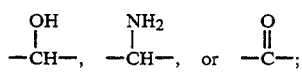

$R^{4c}$ is lower-alkyl, allyl, or lower-alkoxylower-alkyl;
$R^{14}$ is hydrogen or methyl,
which comprises reacting a compound of formula VIIa

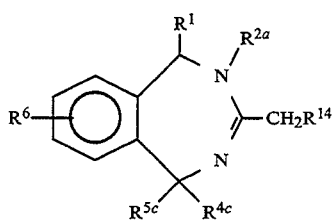

with a strong base followed by reaction with an electrophile chosen from the group consisting of $R^8COOR^{12}$, $R^8CHNR^{12}$, $R^8CHO$, $R^8SSR^8$ and $R^8(X^b)_n(CH_2)_{m-1}Z$ wherein Z is a group subject to nucleophilic displacement.

In a further process aspect, the invention relates to a process for preparing a compound of formula VIa

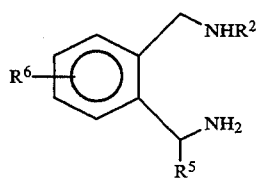

which comprises reacting a compound of formula VIII or IX

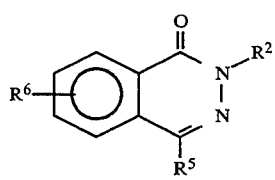

or

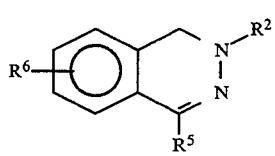

with an excess of diborane.

In a further process aspect, the invention relates to a process for preparing a compound of formula VIb

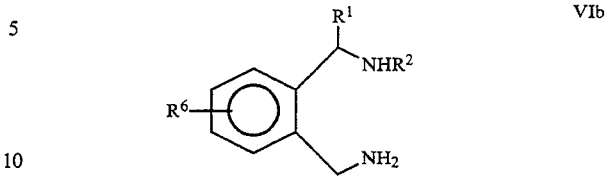

which comprises reacting a compound of formula X or XI

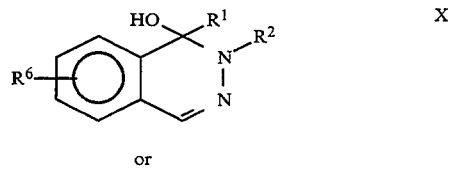

or

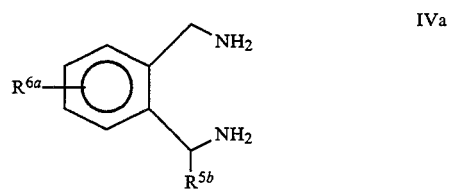

with an excess of diborane.

In a further process aspect, the invention relates to a process for preparing a compound of formula IVa

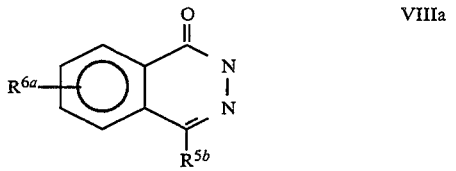

which comprises reducing a compound of formula VIIIa

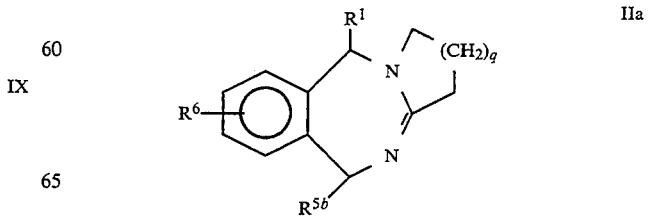

sequentially with an aluminum hydride, hydrogen in the presence of a noble-metal catalyst and hydrogen in the presence of a nickel catalyst.

In a further process aspect, the invention relates to a process for preparing a compound of formula IIa which comprises reacting a diamine of formula VIc

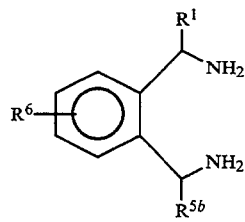

VIc with an ω-haloorthoester or ψ-haloiminoether of formula ZCH$_2$(CH$_2$)$_q$CH$_2$C(OR$^{12}$)$_3$ or ZCH$_2$(CH$_2$)$_q$CH$_2$C(OR$^{12}$)NH.

In a further process aspect, the invention relates to a process for preparing a compound of formula IIa

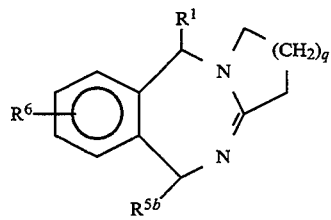

IIa which comprises reacting a compound of formula XII (Bzl=benzyl)

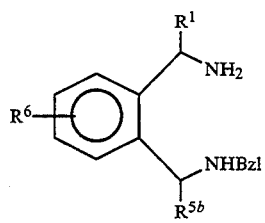

XII with a ω-chloroester of formula ClCH$_2$(CH$_2$)$_q$CH$_2$COOR$^{12}$, followed by cyclization of the resulting ω-chloroalkylamide, hydrogenolysis of the benzylamine, and closure of the diazepine ring.

Other aspects of the invention comprise methods of using the benzodiazepines of the invention for the treatment of cardiac arrhythmia in patients and compositions for the treatment of cardiac arrhythmia containing those compounds. The benzenemethanamines and the δ-aminoamides of the invention are useful both as intermediates and in their own right in methods and compositions for the treatment of arrhythmia.

It has been further found that certain compounds of the invention within the ambit of formula XXXVI above do not reduce (depress) cardiac function and they are thus particularly useful in the treatment of cardiac arrhythmia in a patient with impaired ventricular function or congestive heart failure as is described more fully hereinbelow in the Biological Test Result section. Accordingly, another aspect of the invention comprises a method for the treatment of cardiac arrhythmia in a patient with impaired ventricular function or congestive heart failure which comprises the administration of an antiarrhythmically effective amount of a compound of the formula:

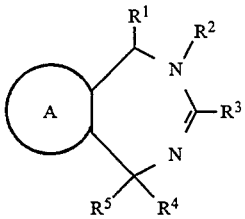

wherein:
A is a ring chosen from the group consisting of phenyl, thienyl and phenyl substituted at any available carbon atom by one or two lower-alkylsulfonamido groups;

R$^1$ is hydrogen or phenyl;

R$^2$ is lower-alkyl or —CH$_2$CH$_2$R$^{7'}$ wherein R$^{7'}$ is lower-alkoxy, pyridinyl, phenyl or phenyl having one or two lower-alkylsulfonamido substituents;

R$^3$ is —(CH$_2$)$_m$—X$_n$—R$^8$ wherein
m is an integer from zero to seven;
X$_n$ is —S—, —O—, —SO$_2$—, —CH=CH—, or —NHSO$_2$—;
n is zero or one;

R$^8$ is lower-alkyl, phenyl, pyridinyl, phenyl having one or two substituents chosen independently from the group consisting of halogen, lower-alkyl, lower-alkoxy, lower-alkylsulfonamido, dilower-alkylaminosulfonyl and polyfluoro-lower-alkylsulfonamido; or pyridinyl having one or two lower-alkyl substituents;

R$^4$ is hydrogen or lower-alkyl; and

R$^5$ is hydrogen, pyridinyl, benzyl, phenyl or phenyl having one or two substituents chosen independently from the group consisting of halogen, lower-alkyl, lower-alkoxy, lower-alkylthio, lower-alkylsulfonyl, lower-alkylsulfonamido, and hydroxy;

or an acid-addition salt thereof; with the proviso that the total number of carbon atoms in R$^1$ plus R$^2$ plus R$^4$ plus R$^5$ must be five or greater; further provided that at least one of R$^2$, R$^3$, R$^5$ or ring A must contain a pyridinyl group, an —NHSO$_2$— group, or a lower-alkylsulfonamido, dilower-alkylaminosulfonyl, or polyfluorolower-alkylsulfonamido substituent.

Still another aspect of the invention comprises compositions for the treatment of cardiac arrhythmia in a patient with impaired ventricular function or congestive heart failure which comprises an antiarrhythmically effective amount of a compound of the formula:

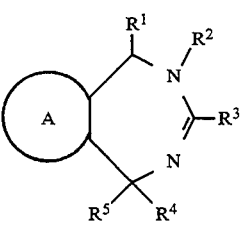

wherein:
A is a ring chosen from the group consisting of phenyl, thienyl and phenyl substituted at any available carbon atom by one or two lower-alkylsulfonamido groups;

R$^1$ is hydrogen or phenyl;

$R^2$ is lower-alkyl or —$CH_2CH_2R^{7'}$ wherein $R^{7'}$ is lower-alkoxy, pyridinyl, phenyl or phenyl having one or two lower-alkylsulfonamido substituents;

$R^3$ is —$(CH_2)_m$—$X_n$—$R^8$ wherein m is an integer from zero to seven;

$X_n$ is —S—, —O—, —$SO_2$—, —CH=CH—, or —$NHSO_2$—;

n is zero or one;

$R^8$ is lower-alkyl, phenyl, pyridinyl, phenyl having one or two substituents chosen independently from the group consisting of halogen, lower-alkyl, lower-alkoxy, lower-alkylsulfonamido, dilower-alkylaminosulfonyl and polyfluoro-lower-alkylsulfonamido; or pyridinyl having one or two lower-alkyl substituents;

$R^4$ is hydrogen or lower-alkyl; and $R^5$ is hydrogen, pyridinyl, benzyl, phenyl or phenyl having one or two substituents chosen independently from the group consisting of halogen, lower-alkyl, lower-alkoxy, lower-alkylthio, lower-alkylsulfonyl, lower-alkylsulfonamido, and hydroxy;

or an acid-addition salt thereof; together with a pharmaceutically acceptable vehicle, adjuvant or excipient; with the proviso that the total number of carbon atoms in $R^1$ plus $R^2$ plus $R^4$ plus $R^5$ must be five or greater; further provided that at least one of $R^2$, $R^3$, $R^5$ or ring A must contain a pyridinyl group, an —$NHSO_2$— group, or a lower-alkylsulfonamido, dilower-alkylaminosulfonyl, or polyfluorolower-alkylsulfonamido substituent.

DETAILED DESCRIPTION INCLUSIVE OF PREFERRED EMBODIMENTS

A general synthesis of compounds of the invention sharing general formula XXXVI may be outlined as shown in Scheme A.

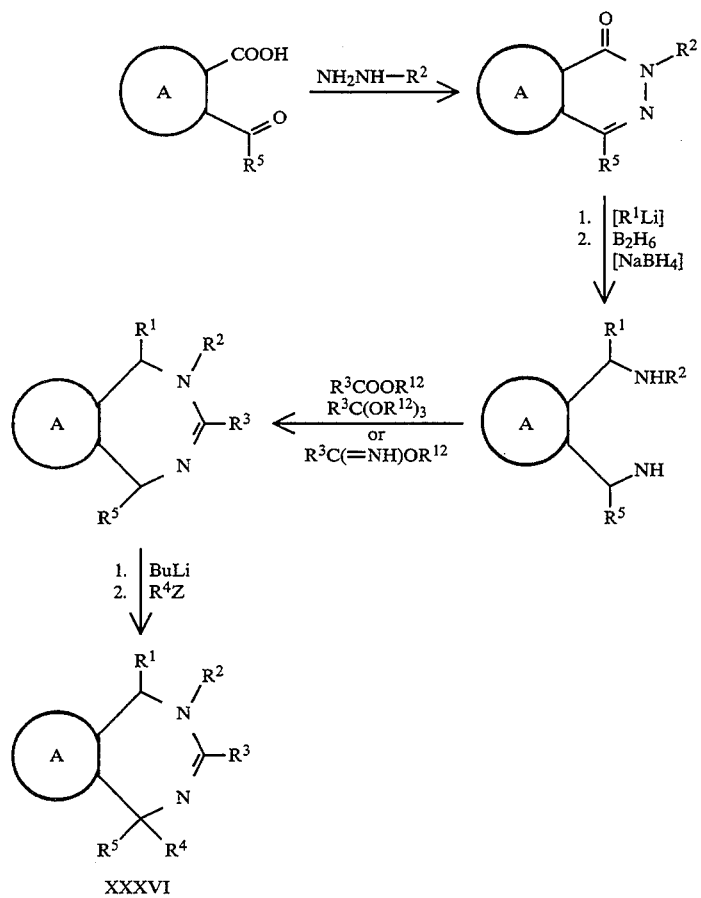

Scheme A

This is more particularly illustrated in Scheme B wherein A is phenyl or substituted phenyl:

Scheme B

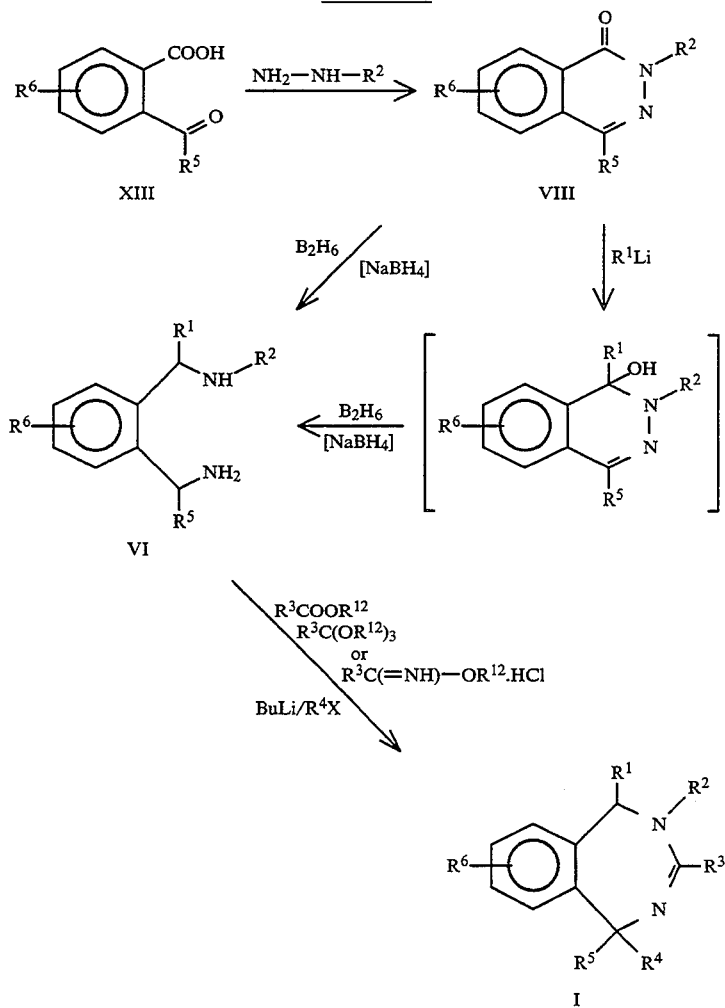

A suitably substituted γ-oxo-acid of formula XIII is reacted with a suitably substituted hydrazine to form a phthalazinone (VIII). In the case where it is desired that $R^1$ be other than hydrogen, the phthalazinone is reacted with a slight excess of a suitable alkyl or aryllithium compound in an inert solvent, preferably THF, at −78° to 0° C., preferably about −65° C., and the resulting adduct is reduced as described below without isolation. In the case where $R^1$ is hydrogen, the phthalazinone (VIII) is reduced directly to the diamine (VI) with 3.5 to 9.0 equivalents of diborane in an inert solvent, preferably THF, at 20° to 100°, preferably 67° C. A catalytic amount of sodium borohydride and some diglyme may be added.

The diamine (VI) may be condensed in one of three ways to produce the benzodiazepine (I, $R_4$=H): (1) the free base of the diamine in acetic acid is treated with five to seven equivalents of the appropriate orthoester $R^3C(OR^{12})_3$ at 0°–50° C., preferably 25° C., or the diacid salt of the diamine, preferably the dihydrochloride salt, in an inert solvent is treated with one to seven equivalents of an appropriate orthoester plus one to two equivalents of a weak base, preferably sodium or potassium acetate; (2) a diacid salt of the diamine (VI), preferably the dihydrochloride salt, in an inert solvent, preferably methanol, is treated with two to three equivalents of the appropriate iminoether hydrochloride and about two equivalents of a weak base, preferably sodium acetate, at 0° to 60° C., preferably 25° C., or the free base of the diamine (VI) in an inert solvent, preferably methanol, is treated with two to three equivalents of the appropriate iminoether hydrochloride and two to three equivalents of a weak acid, preferably acetic acid, at 0° to 60° C., preferably 25° C., or (3) a diamine or a diacid salt of the diamine, preferably the dihydrochloride salt, in an inert solvent, preferably toluene or sulfolane or a mixture thereof, is treated with slightly more than two equivalents of trimethylaluminum to 4.5 equivalents of trimethylaluminum at −30° C. up to the boiling point of the solvent used, preferably at −30° to +110° C., or with 2.5–3.5 equivalents of triisobutylaluminum at a temperature in the range of about room temperature up to the boiling point of the solvent used, followed by treatment with 1 to 1.5 equivalents of a lower-alkyl ester of the appropriate acid ($R^3COOR^{12}$).

In the case where it is desired that $R^4$ be other than hydrogen, the diazepine (I, $R_4$=H) may be reacted with a strong base such as butyllithium and the resulting anion reacted with an appropriate electrophile.

It will, of course, be appreciated that all of the reactions described for the compounds of formula XXXVI wherein A is a phenyl ring are equally applicable to the compounds wherein A is other than phenyl. The starting materials are likewise commercially available or known in the art.

Compounds of formula XXXV (wherein $R^{2c}$ is lower-alkyl, benzyl, phenyl, or phenethyl), which may also be visualized as analogs of the compounds of formula I having an alkylene substituent $R^2$ cyclized into the methine to which $R^1$ is attached, may be synthesized in a similar fashion using butyllithium and an alkylene dihalide followed by reductive debenzylation when $R^{2c}$ is benzyl:

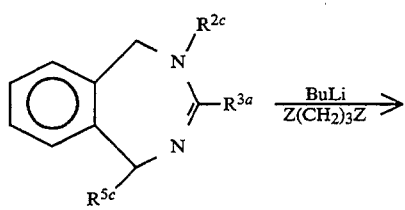

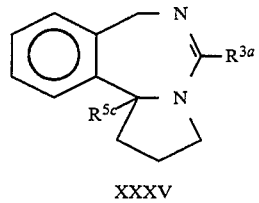

XXXV

Compounds of formula V, a subset of benzodiazepines of formula I, may be prepared by the ring closure of aminoamides. A monosalt of the aminoamide XXVII or XXVIII, preferably the monohydrochloride in an inert solvent, preferably toluene, is treated with a slight excess, preferably about 1.1 equivalents, of trimethylaluminum at 0° to 150°, preferably about 110° to produce a benzodiazepine of formula V:

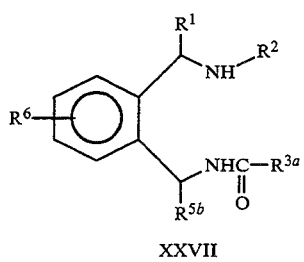

XXVII

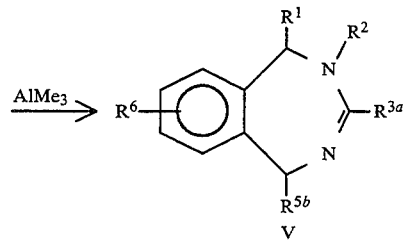

V

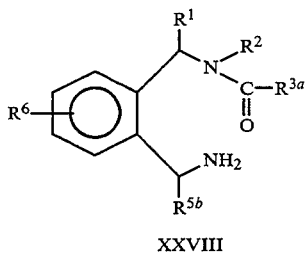

XXVIII

Aminoamides of formula XXVII may be obtained as described in Examples 177–184 by incomplete cyclization or, as described in General Method U, by hydrolytic cleavage of benzodiazepines. Aminoamides XXVII or XXVIII or mixtures of the two may also be obtained by procedures well known in the art for condensing acids of formula $R^{3a}COOH$ with amines of formula VId

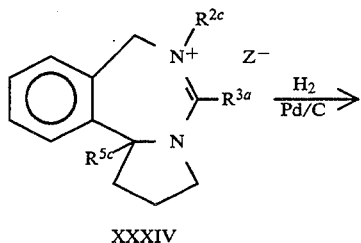

XXXIV

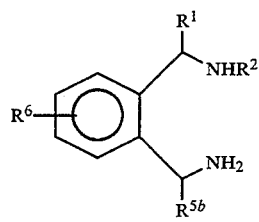

VId

In the case of compounds of formula I where p (in $R^3$) is one and $Y^b$ is —NH—, —S—, or —O—, the compounds may be made by an alternate route from the diamine VI shown in Scheme C:

then be displaced by an appropriate nucleophile, as before, optionally in an inert solvent at 0°–100° C. Example 153 illustrates an alternative, lower-yield conversion of the thione to the compounds of formula Vb.

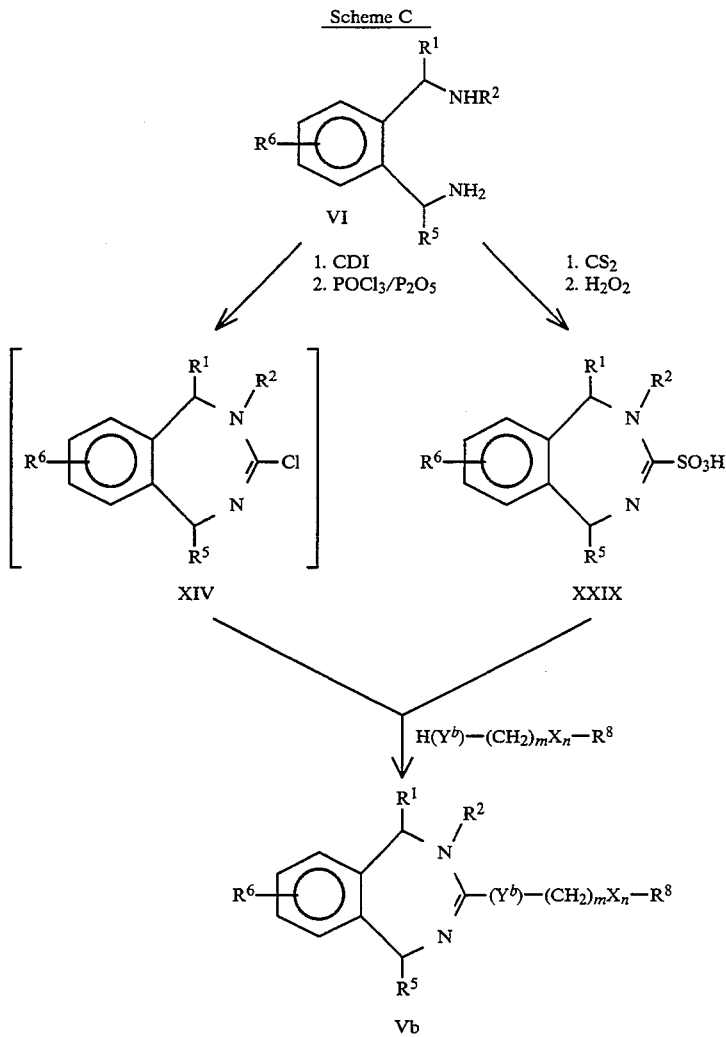

The diamine (VI) is reacted with carbonyl diimidazole (CDI) in an inert solvent, preferably chloroform, at ambient temperature to produce a benzodiazepin-3-one, which is treated with a large excess, preferably about 13 equivalents, of phosphorus oxychloride and preferably about 0.25 equivalents of phosphorus pentoxide to produce a 3-chlorobenzodiazepine (XIV). The 3-chlorobenzodiazepine is then reacted, usually without isolation, with the appropriate nucleophile, $R^8X_n(CH_2)_m(Y^b)H$, to produce the benzodiazepines of structure Vb.

Alternatively the diamine VI is reacted with preferably about one equivalent of carbon disulfide in an inert solvent, preferably 2-propanol, at 0° to 100° C., preferably at about 20° to 85° C. and the resulting carbamodithioic acid is treated with a catalytic amount of an acid, preferably hydrochloric acid, in an inert solvent, preferably ethanol, at 0° to 100° C., preferably at about 78° C., to produce a tetrahydrobenzodiazepine-3-thione. The thione is oxidized with slightly more than three equivalents of 30% hydrogen peroxide according to the procedure of Maryanoff et al. [*J. Org. Chem.* 51, 1882 (1986)] to produce the sulfonic acid XXIX. The sulfonate may In the case where all of $R^2$, $R^4$ and $R^5$ are other than hydrogen, the subgenus of compounds of formula VII wherein $R^3$ is attached to the benzodiazepine ring through a carbon (i.e. p in $R^3$ is zero and $R^3$ is —$CH_2(CH_2)_{m-1}X_nR^8$ or p is one and Y is

may be made alternately

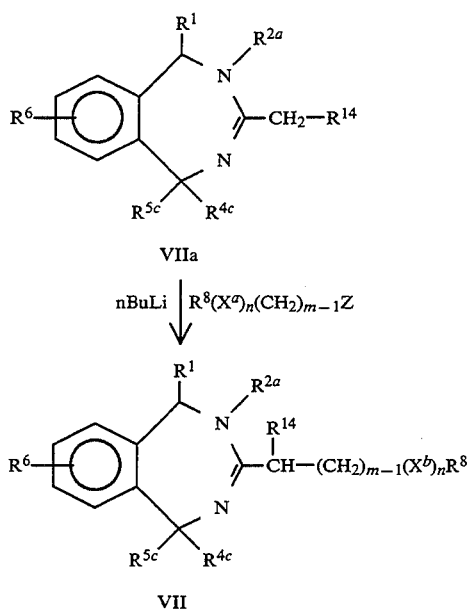

VIIa nBuLi | R⁸(Xᵃ)ₙ(CH₂)ₘ₋₁Z

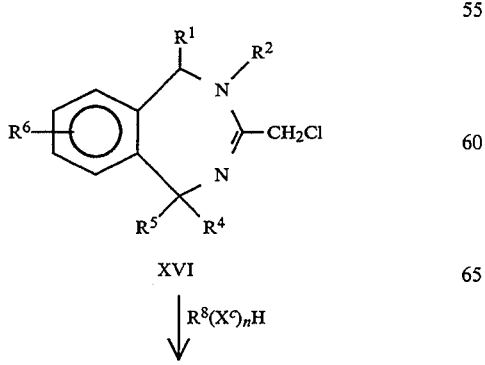

VII by treatment of a compound of formula VIIa wherein R¹⁴ is hydrogen or methyl in an inert solvent, preferably THF, at −78° to +25° with a slight excess, preferably about 10 to 20%, of a strong base, preferably n-butyllithium followed by a slight excess, preferably 10–50%, of an appropriate electrophile. The electrophile can be of the form $R^8—(X^a)_n—(CH_2)_{m-1}—Z$ wherein Z is a group that is readily displaced by an anion, such as a halogen, sulfide, sulfonate, ester, etc. or in the case where m minus one is zero it can take the form of an aldehyde, ketone or imine so that addition of the anion to the electrophile followed by quenching with a proton source results in the overall addition of the elements of VIIa to the electrophile.

In cases where R³ is attached to the benzodiazepine via a heteroatom-methylene link (XV), that is R³ is of the form —CH₂(Xᶜ)ₙR⁸ wherein Xᶜ is —S—, —O— or —SO₂— (i.e. in formula XXXVI, X is —S—, —O— or —SO₂—, p is zero, m is one and n is one when R⁸ is lower-alkyl, phenyl or substituted phenyl; n is zero when R⁸ is amino or an N— attached heterocycle) the compounds may conveniently be synthesized from the corresponding chloromethyl species (XVI).

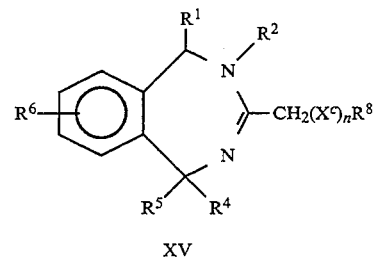

XVI

↓ R⁸(Xᶜ)ₙH

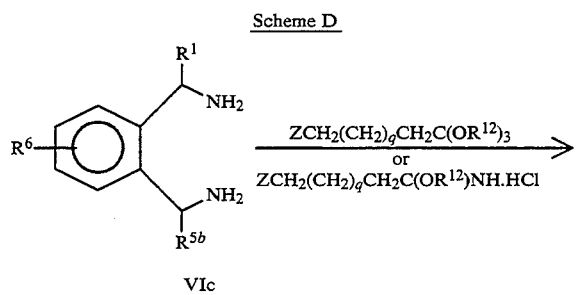

XV

The 3-chloromethyl-2,4-benzodiazepine (XVI) in an inert solvent, preferably chloroform when the heteroatom is nitrogen and methanol or acetonitrile when the heteroatom is sulfur, is treated with one to three equivalents of the R⁸(Xᶜ)ₙH species at 0° to 100° C., preferably at 25° to 65° C. The chloromethyl benzodiazepine XII can be synthesized directly from the diamine VI by condensation with ethyl 2-chloroethanimidate or in the case where all of R², R⁴ and R⁵ are other than hydrogen, the chloromethyl benzodiazepine (XVI) may be synthesized from the corresponding 3-methylbenzodiazepine by anion formation as described in the foregoing paragraph and quenching with about 1.1 equivalents of hexachloroethane.

Compounds of formula IIa and XVII may be synthesized by the routes shown in Schemes D and E. Scheme D produces mixtures from which the isomers can be separated by chromatography; Scheme E produces a single isomer selectively.

Scheme D

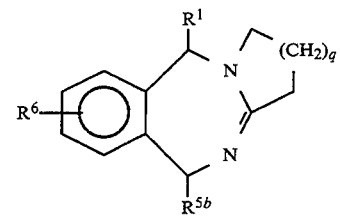

VIc

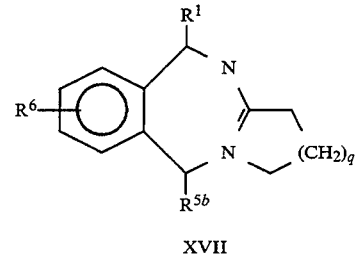

IIa

+

XVII

A diamine of formula VIc as its dihydrochloride is treated with about two equivalents of an appropriate ω-haloiminoether salt, preferably the ω-chloroiminoether hydrochloride, and about two equivalents of a weak base, preferably sodium acetate, in an inert solvent, preferably methanol. The resulting mixture of isomers is separated, usually by chromatography on silica gel, although in some cases separation may be achieved by simple crystallization. It will be noted that the compounds of structure XVII can be represented by formula IIa wherein the substituents $R^1$ and $R^{5b}$ are interchanged.

zyl is removed, preferably by hydrogenolysis in the presence of a palladium metal catalyst. The aminoamide XXI as its salt, preferably the hydrochloride, is treated with a slight excess of trimethylaluminum in an inert solvent, preferably toluene, at 50 to 150° preferably 110°, to provide a tricyclic benzodiazepine of formula IIa.

If it is desired that $R^{4a}$ or $R^{15}$ in formula II be other than hydrogen, the compounds of formula IIa may be alkylated in a similar fashion to that described for the benzodiazepines of formula I, using a strong base such as butyllithium and an electrophile such as $R^{4a}Z$ or

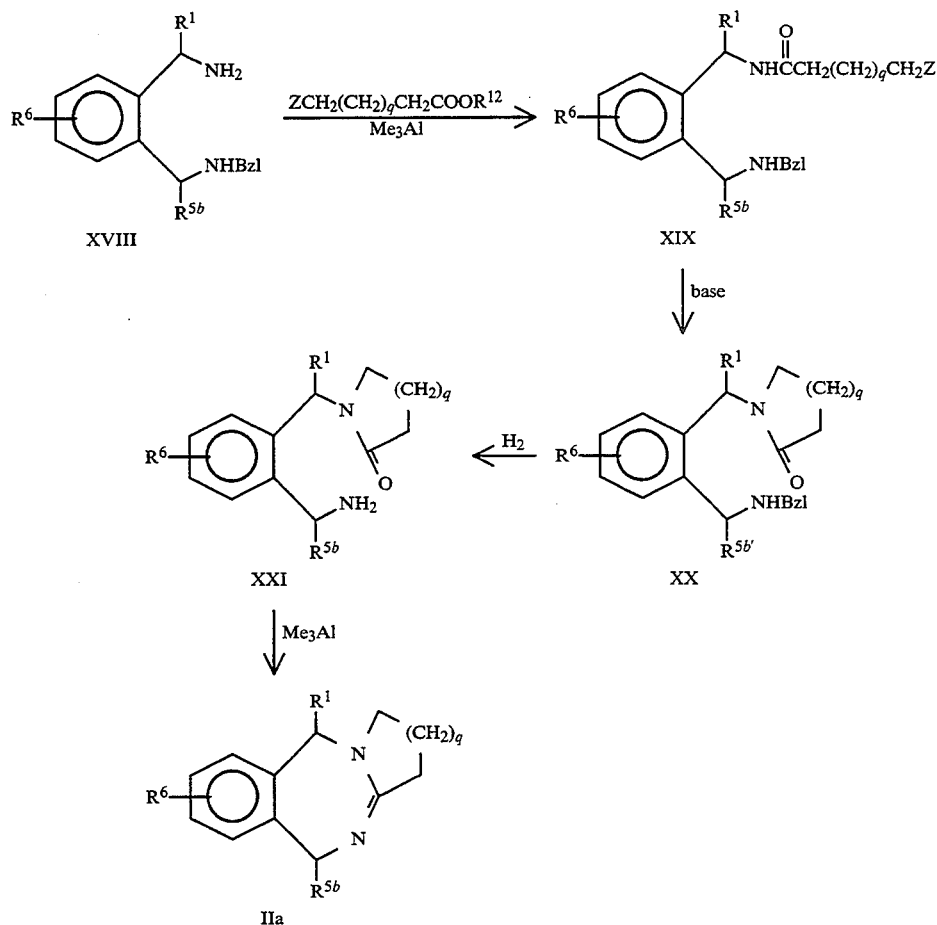

A disalt, preferably a dihydrochloride, of a monobenzyldiamine of formula XVIII is treated with 1 to 1.5 equivalents of an ω-activated methyl or ethyl ester of formula $ZCH_2(CH_2)_qCH_2COOR^{12}$ and about two equivalents of trimethylaluminum in an inert solvent, preferably toluene, at 0 to 60°, preferably about 55°. The resulting amide (XIX) is treated with about a 3-fold excess of a hindered strong base, preferably potassium t-butoxide, in an inert solvent, preferably THF, at 0°–60°, preferably about 25°, to produce a pyrrolidinone (XX, q=21) or a piperidinone (XX, q=2). The N-ben- $R^{15}Z$. Similarly, if it is desired that $R^{16}$ be other than hydrogen, the appropriately substituted tricycles may be alkylated as before, using a strong base such as butyllithium and an electrophile, $R^{16}Z$. The sequence of alkylations will depend on the nature of the substituents $R^1$ and $R^5$. For example, when $R^1$ is aryl and $R^5$ is other than aryl, the alkylation will occur first for $R^{15}$ and then for $R^{16}$ (via IId and IIe); when $R^5$ is aryl and $R^1$ is other than aryl, the alkylation will occur first for $R^{4a}$ and then for $R^{16}$ (via IIb and IIc):

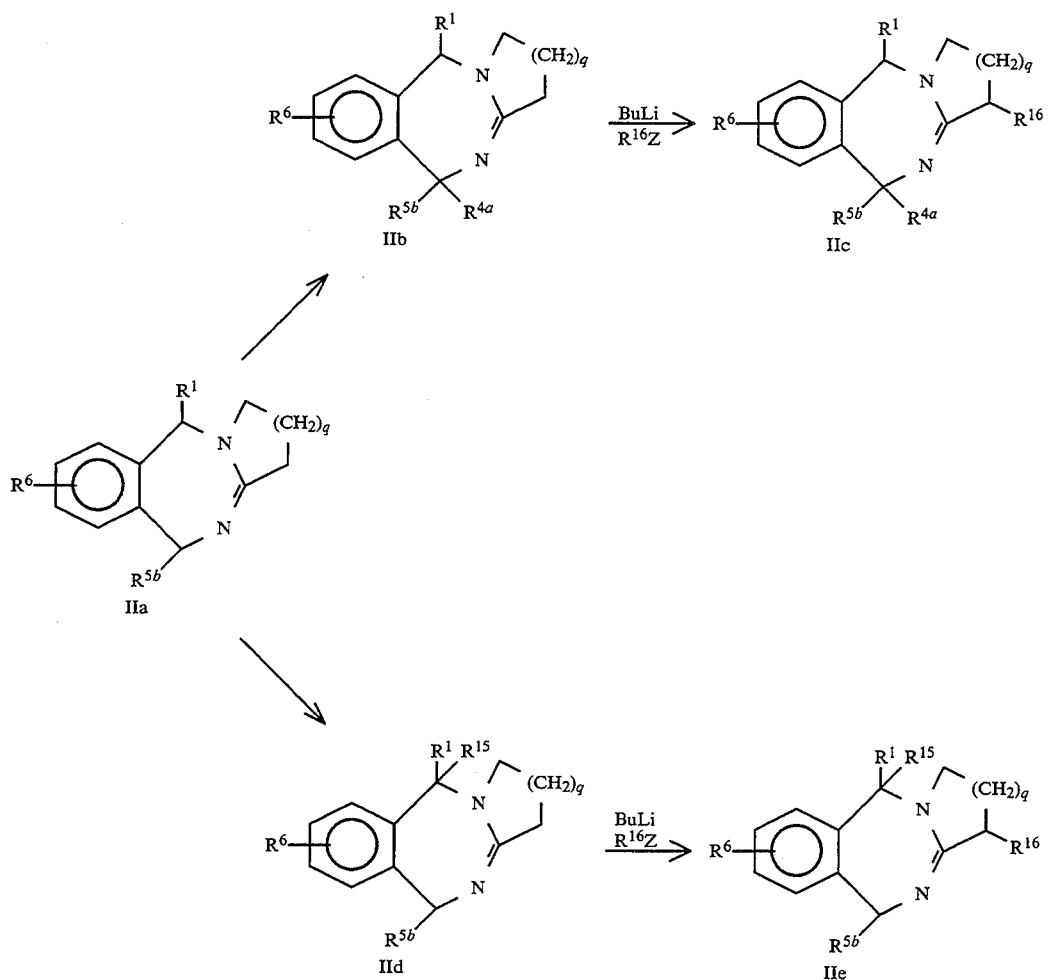

Compounds of formula III may be synthesized from the corresponding compounds of formula I by hydrolysis in the presence of 1 to 5 equivalents of aqueous base, preferably potassium hydroxide, in a cosolvent, preferably methanol, at 0° to 70°, preferably 25 to 30°.

Compounds of formula IV may be prepared by the reduction and cleavage of phthalazinones and phthalazines as shown in Scheme F.

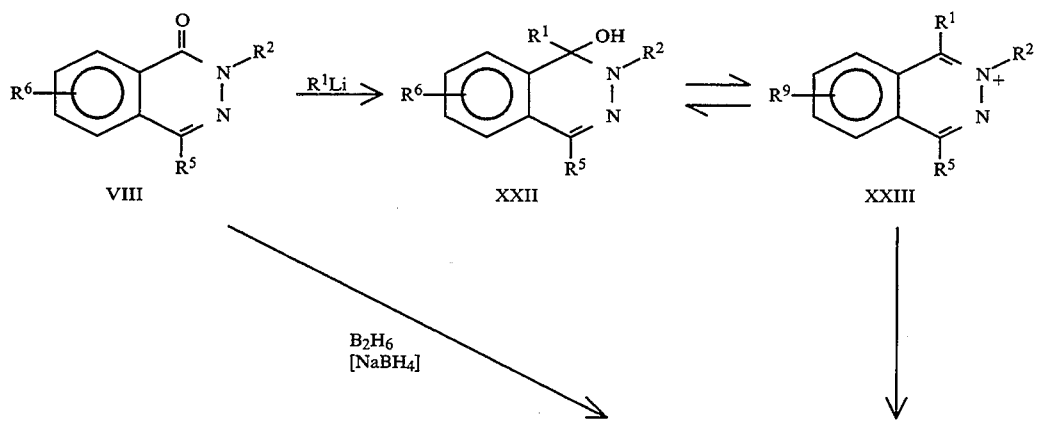

-continued
Scheme F

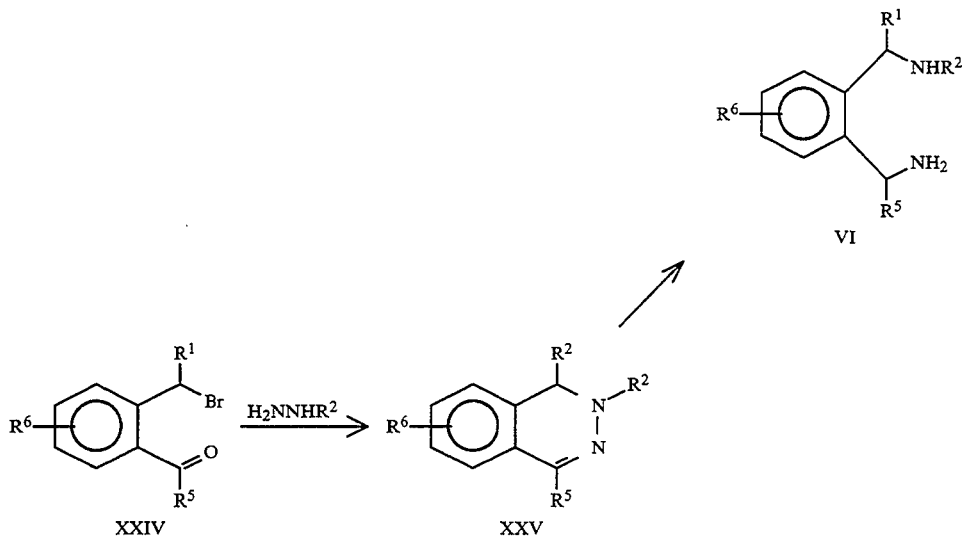

A phthalazinone of formula VIII is reacted with 3.5 to 9.0 equivalents of diborane in an inert solvent, preferably THF, at 20° to 100°, preferably about 67°, to produce diamines of the formula VI wherein $R^1$ is hydrogen. A catalytic amount of sodium borohydride in diglyme may be added. If it is desired that $R^1$ be other than hydrogen, phthalazines of formulas XXII, XXIII and XXV may be reduced in like fashion. The phthalazines XXII and XXIII may be obtained from the corresponding phthalzinones by reaction with a suitable alkyllithium or aryllithium in an inert solvent, preferably THF, at −78° to 0°, preferably about −65°. The resulting phthalazine may exist as the hydroxyphthalazine XXII or may spontaneously eliminate the elements of water to form the phthalazinium species XXIII. The phthalazines of formula XXV may be synthesized by the condensation of the appropriate hydrazine with a γ-haloketone, preferably a γ-bromoketone.

The diamines of the formula VI wherein $R^1$ is hydrogen, can also be prepared by (a) the treatment of an aminoamide of the formula XXVII, wherein $R^{5b}=R^5$, with an excess of an appropriate acid, such as sulfuric acid or hydrochloric acid, or a mixture of said acids, at a temperature of about room temperature up to the boiling point of the acid or acid mixture; or (b) the treatment of a benzodiazepine of formula I, wherein $R^4$=hydrogen, with an excess of ethylene diamine, in an inert solvent, such as toluene, or neat, at a temperature in the range of about room temperature up to the boiling point of the solvent used.

In the case wherein in formula VIII $R^2$ is hydrogen, the simple reduction with diborane described above is so slow as to be of less practical use than a three-step reduction:

Scheme G

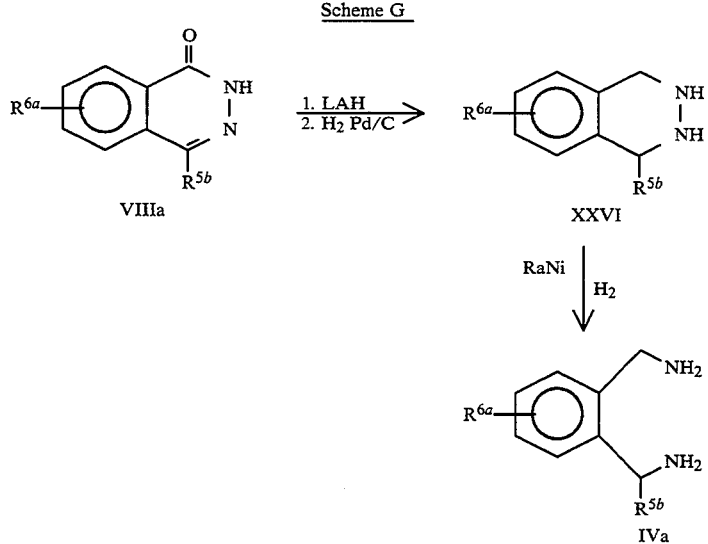

The phthalazinone VIIIa is treated with about two equivalents of an aluminum hydride reducing agent, preferably lithium aluminum hydride, in an inert solvent, preferably THF, at 20° to 120°, preferably about 65°. The resulting dihydrophthalazine is reacted with hydrogen in an inert solvent, preferably a lower alkanol, most preferably ethanol, in the presence of a palladium catalyst at 20° to 60°, preferably 40°–50°, preferably at about 3 atmospheres pressure. The resulting tetrahydrophthalazine (XXVI) is reacted with hydrogen in an inert solvent, preferably methanol, in the presence of a Raney nickel catalyst at 20° to 80°, preferably about 65°, preferably at about 3 atmospheres pressure.

The 1,4,5,6-tetrahydro-2,4-benzodiazocines of formula XXX may be synthesized in an analogous fashion to the benzodiazepines of formula I by the condensation of the appropriate diamines XXXII with orthoesters, iminoesters or esters plus trialkylaluminum reagents. The desired diamines are obtained, as before, by diborane reduction of the corresponding 2,3-benzodiazepin-4-ones XXXIII, which are available by reaction of ketoacids XXXIV with hydrazines. The ketoacids are obtained by Grignard reaction of indenones followed by oxidation with chromium trioxide according to the procedure of de Paulis et al. [*J. Med. Chem.* 24, 1021–1026 (1981)]. The sequence is shown in Scheme H.

synthesized from chiral starting materials or the racemates may be resolved by methods well known in the art, such as chromatography on chiral media or recrystallization of diastereomeric salts.

Simple chemical transformations which are conventional and well known to those skilled in the art of chemistry can be used for effecting change in functional groups in the compounds of the invention. For example, catalytic reduction of arylnitro compounds to afford the corresponding arylamines; dealkylation of aryl ethers to afford the corresponding phenols; and treatment of arylamines with lower-alkylsulfonyl halides to afford the corresponding sulfonamides.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form.

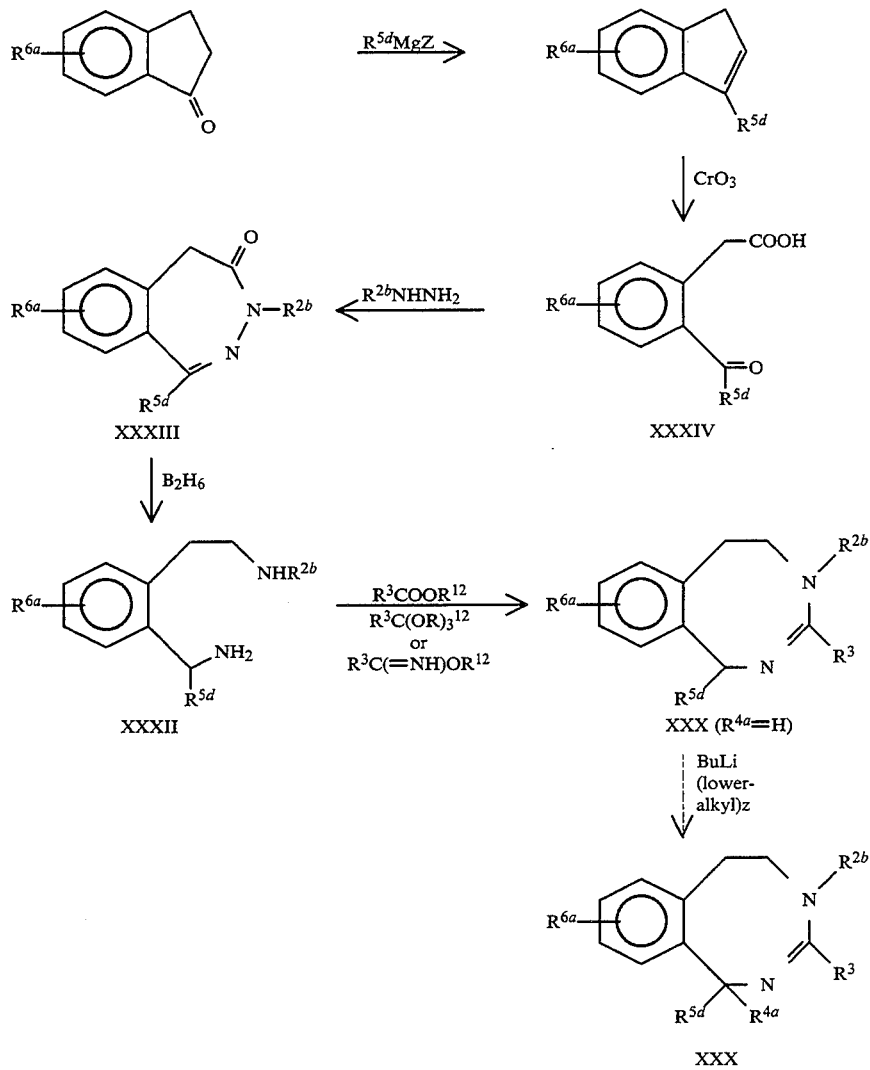

Scheme H

It will be noted that many of the compounds of the invention are asymmetric at C-1 of the benzodiazepine or benzodiazocine. In some cases there may be an advantage to using one or the other enantiomer for the treatment of arrhythmia. Single enantiomers may be The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention, it is convenient to form the hydrochloride, fumarate, toluenesulfonate, hydrogen sulfate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, and mass spectroscopy. The course of the reactions and the identity and homogeneity of the products were assessed by thin layer chromatography (TLC) and high-pressure liquid chromatography (HPLC). The starting materials are either commercially available or may be prepared by procedures well known in the art.

In the following procedures, melting points are given in degrees C. and are uncorrected.

In the examples which follow, Me is methyl, Et is ethyl, Ph is phenyl, Bzl is benzyl, iPr is isopropyl, tBu is t-butyl, OAc is acetyl, THF is tetrahydrofuran, hex is hexane, IPA is isopropylamine, DMF is dimethylformamide, and TMS is trimethylsilyl.

TABLE A

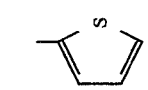

| Example No. | R² | R³ | R⁵ | R⁶ | Method | Yield % | Melting Range | Salt | Recrystallized From |
|---|---|---|---|---|---|---|---|---|---|
| 1 | Me | Ph | Ph | H | A | 63 | 114-115 | free base | hexane |
| 2 | Me | Me | Ph | H | A | 27 | 177-178 | maleate | MeCN |
| 3 | Me | Et | (2-thienyl) | H | B | 26 | 213-215 | HCl | MeCN |
| 4 | iPr | Et | Ph | H | C | 71 | 232-234 | HCl | EtOAc/ether |
| 5 | Bzl | Et | Ph | H | C | 37 | 222-224 | HCl | EtOH/MeCN/ether |
| 6 | Me | —CH₂Cl | Ph | H | D | 30-95 | 129-131 | HCl·1H₂O | tBuOMe/hexane |
| 7 | Me | Et | Me | H | A | 59 | 207-209 | free base | EtOH/tBuOMe |
| 8 | Me | Et | Ph | H | A | 40 | 198-200 | HCl | MeCN/tBuOMe |
| 8A | | | | | | | 163-165 | maleate | acetone |
| 8B | | | | | | | 98-100 | free base | iPrOAc |
| 8C | | | | | | | 201-202 | HCl | acetone |
| 8D | | | | | | | 178-179 | HCl | iPrOH |
| 8E | | | (4-methoxyphenyl) | | | | 172-174 | ½ fumarate toluene-sulfonate methane-sulfonate | EtOAc |
| 9 | Me | H | Ph | 7,8-diOMe | A | 48 | 148-150 | maleate | EtOAc/MeCN |
| 10 | Me | nPr | Ph | H | A | 49 | 218-221 | HCl | MeCN/tBuOMe |
| 11 | Me | nBu | Ph | H | A | 46 | 212-214 | HCl | MeCN/tBuOMe |
| 12 | CH₂CH₂OMe | Et | Ph | H | D | 44 | 186-189 | HCl | iPrOH/tBuOMe |
| 13 | Me | CH₂CH₂—cC₆H₁₁ | Ph | H | D | 80 | 146 | HCl | MeCN/ether |
| 14 | Me | —(CH₂)₄CH₃ | Ph | H | D | 27 | 197-198 | HCl | acetone/ether |
| 15 | H | —CH₂CH₂Ph | Ph | H | A | 90 | 148-149 | free base | CH₂Cl₂/hexane |
| 16 | Me | Et | Ph | 6-F | A | 50* | 152-154 | maleate | MeOH/ether |
| 17 | Me | Et | Ph | 7-F | A | 53* | 185-187 | maleate | MeOH/ether |
| 18 | Me | Et | Ph | 8-F | A | 69 | 158-161 | maleate | MeOH/ether |

*over two steps

TABLE A-continued $$\text{R}^6\underset{\text{NH}_2}{\overset{\text{NHR}^2}{\bigoplus}}\overset{\text{R}^5}{\underset{}{}} + \text{R}^3\text{C(OR}^{12}) \atop \text{R}^3\text{C(NH)OR}^{12} \atop \text{or} \atop \text{R}^3\text{COOR}^{12} \longrightarrow \text{R}^6\underset{}{\overset{\text{R}^2}{\bigoplus}}\overset{\text{R}^3}{\underset{\text{R}^5}{}}$$

| Example No. | R² | R³ | R⁵ | R⁶ | Method | Yield % | Melting Range | Salt | Recrystallized From |
|---|---|---|---|---|---|---|---|---|---|
| 19 | Me | Et | ![naphthyl] | H | A | 48 | 145–148 | — | EtOH |
| 20 | Me | iPr | Ph | H | B | 60 | 79–80 | — | Et₃N/pentane |
| 21 | Me | Bzl | Ph | H | B | 79 | 236–237 | HCl | MeCN |
| 22 | iPr | PhCH₂CH₂ | Ph | H | E | 73 | 150–153 | maleate | acetone/ether |
| 23 | iPr | Me | Ph | H | E | 56 | 165–166 | maleate | acetone/ether |
| | | | | | | 71 | 130–132 | free base | EtOAc/hexane |
| 24 | iPr | nBu | Ph | H | E | 78 | 108–109 | maleate hemihydrate | acetone/ether or MeCN/tBuOMe |
| 25 | Me | PhCH₂CH₂ | Ph | H | D | 50 | 118–123 | HCl | MeCN/ether |
| | | | | | F | 62 | 132–133 | HCl | MeCN |
| 26 | Ph | Me | Me | H | A | 35 | 89–92 | HCl | EtOH/tBuOMe |
| 27 | Ph | Et | Me | H | A | 2 | 207–208 | HCl | MeCN/tBuOMe |
| 28 | Me | Me | 4-F-C₆H₄ | H | A | 53 | 185–187 | maleate | EtOH/tBuOMe |
| 29 | Me | Ph | 4-F-C₆H₄ | H | A | 48 | 146–148 | free base | MeCN |

TABLE A-continued

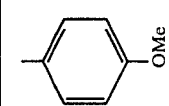

| Example No. | R² | R³ | R⁵ | R⁶ | Method | Yield % | Melting Range | Salt | Recrystallized From |
|---|---|---|---|---|---|---|---|---|---|
| 30 | Me | Me | 4-MeO-C₆H₄ | H | A | 26 | 235–237 | HCl | MeCN/tBuOMe |
| 31 | Me | Me | Me | H | A | 60 | 241–243 | HCl | MeCN/tBuOMe |
| 32 | Me | Et | Ph | 8,9-benzo | A | 40 | 149–151 | free base | florisil EtOAc/IPA Chromatog. |
| 33 | Me | Et | Ph | 9-Me | A | | 49–53 | free base | florisil EtOAc/IPA Chromatog. |
| 34 | Me | —(CH₂)₇CH₃ | Ph | H | D | 28 | 159–161 | HCl | MeCN/ether |
| 35 | Me | 4-MeO-C₆H₄-CH₂CH₂— | Ph | H | D | 53 | 131–133 | HCl | MeOH/ether |
| 37 | Me | Et | 4-F-C₆H₄ | H | A | 58 | 133–135 | maleate | MeCN/tBuOMe |

TABLE A-continued

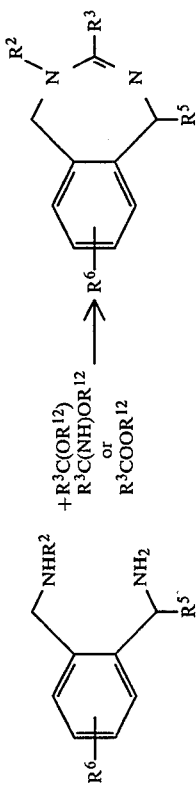

| Example No. | R² | R³ | R⁵ | R⁶ | Method | Yield % | Melting Range | Salt | Recrystallized From |
|---|---|---|---|---|---|---|---|---|---|
| 38 | Me | —CH₂O—(benzodioxole) | Ph | H | D | 33 | 196–198 | HCl | EtOH/ether |
| 39 | Me | —CH₂O—(4-Cl-C₆H₄) | Ph | H | D | 14 | 166–168 | HCl ½H₂O | EtOH/ether |
| 40 | Me | —CH₂O—(4-OMe-C₆H₄) | Ph | H | D | 17 | 225–226 | HCl | EtOH/ether |
| 41 | Me | Et | 2-Cl-5-NH₂-C₆H₃ | H | G | 23 | 249–251 | fumarate | EtOH/ether |
| 42 | Me | —CH₂OPh | Ph | H | G | 74 | 153–155 | HCl | EtOH/ether |
| 43 | Me | —(CH₂)₃Ph | Ph | H | E | 79 | 101–106 | fumarate | EtOH/ether |
| 44 | CH₂CH₂OMe | Ph | Ph | H | A | 70 | 170–172 | maleate | MeCN |
| 45 | CH₂CH₂NEt₂ | Me | Ph | H | A | 24 | 154–156 | 2 maleate | MeCN |
| 46 | CH₂CH₂NEt₂ | H | Ph | H | A | 18 | 145–147 | 2 maleate | acetone tBuOMe |

TABLE A-continued

| Example No. | R² | R³ | R⁵ | R⁶ | Method | Yield % | Melting Range | Salt | Recrystallized From |
|---|---|---|---|---|---|---|---|---|---|
| 47 | CH₂CH₂—N(morpholine) | H | Ph | H | A | 27 | 175–177 | 2 maleate | EtOH |
| 48 | CH₂CH₂N(morpholine) | Me | Ph | H | A | 15 | 167–169 | 2 maleate | MeCN/tBuOMe |
| 49 | Me | H | Ph | H | A | 7 | 149–151 | 2 maleate | EtOH |
| 50 | CH₂CH₂NEt₂ | Et | Ph | H | A | 10 | 224–227 | 2 HCl | MeCN/tBuOMe |
| 51 | Me | cyclopropyl | Ph | H | G | 29 | 113–115 | free base | iPrOH |
| 52 | Me | CH₂CH₂Ph | Bzl | H | D | 47 | 139–141 | fumarate | EtOH |
| 53 | CH₂—cyclopropyl | CH₂CH₂Ph | Ph | H | E | 45 | 173–187 | HCl | acetone/ether |
| 54 | CH₂—cyclopropyl | Et | Ph | H | E | 87 | 189–191 | HCl | acetone/ether |
| 55 | CH₂—cyclopropyl | Me | Ph | H | E | 70 | 226–234 | HCl | acetone/ether |
| 56 | CH₂CH₂Ph | Et | Ph | H | E | 90 | 225–228 | HCl | acetone |
| 57 | CH₂CH₂Ph | Me | Ph | H | E | 95 | 233–235 | HCl | acetone/ether |

TABLE A-continued

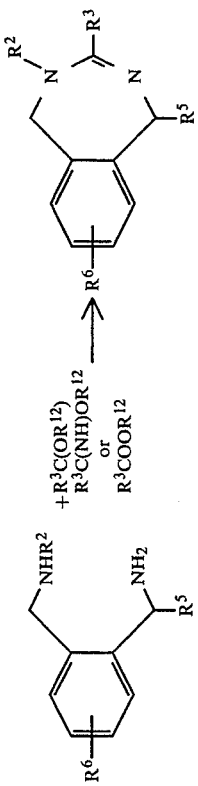

| Example No. | R² | R³ | R⁵ | R⁶ | Method | Yield % | Melting Range | Salt | Recrystallized From |
|---|---|---|---|---|---|---|---|---|---|
| 58 | Me | CH₂CH₂-(4-Cl-C₆H₄) | Ph | H | D | 48 | 185–187 | fumarate | iPrOH/ether |
| 59 | Me | CH₂SO₂Ph | Ph | H | F | 47 | 255–257 | HCl | MeOH/ether |
| 60 | Me | CH₂CH₂Ph | 4-MeO-C₆H₄ | H | D | 35 | 204–206 | HCl | MeOH/ether |
| 61 | Me | CH=CHPh trans | Ph | H | F | 67 | 245–250 | HCl | CHCl₃/ether |
| 62 | Me | Ph | 4-pyridyl | H | C | 30 | 134 (d) | free base | iPrOH/hexane |
| 63 | Me | CH₂CH₂Ph | 4-Cl-C₆H₄ | H | G | 31 | 202–203 | HCl | MeCN/EtOH |
| 210 | Bzl | Me | Ph | H | E | 74 | 126–127 148–149 | free base HCl | EtOAC/hexane MeOH/MeOtBu |
| 211 | Me | CH=CH-(2-furyl) | Ph | H | F | 28 | 237–239 | fumarate | MeOH/EtOH/ether |

TABLE A-continued $$\begin{array}{c}\text{NHR}^2\\\text{NH}_2\\\text{R}^5\\\text{R}^6\end{array} \xrightarrow[\text{or}]{+R^3C(OR^{12})\atop R^3C(NH)OR^{12}\atop R^3COOR^{12}} \begin{array}{c}R^2\\N\\\phantom{N}\\N\\R^5\\R^6\end{array}R^3$$

| Example No. | R² | R³ | R⁵ | R⁶ | Method | Yield % | Melting Range | Salt | Recrystallized From |
|---|---|---|---|---|---|---|---|---|---|
| 212 | Me | CH=CH–(2-thienyl) | Ph | H | F | 22 | 234–236 | fumarate | MeOH/EtOH/ether |
| 213 | Me | CH₂CH₂–(2-furyl) | Ph | H | F | 67 | 184–185 | fumarate | EtOH/ether |
| 214 | Me | CH₂CH₂–(2-thienyl) | Ph | H | F | 48 | 176–177 | fumarate | EtOH/ether |
| 215 | Me | CH=CH–(3-furyl) | Ph | H | F | 22 | 212–213 | fumarate | EtOH/ether |
| 216 | Me | CH=CH–(3-thienyl) | Ph | H | F | 42 | 246–247 | fumarate | MeOH/EtOH/ether |
| 217 | Me | CH₂CH₂Ph | (CH₂)₃CH₃ | H | D | 20 | 152–154 | HCl | MeOH |
| 218 | Me | CH₂CH₂–(3-thienyl) | Ph | H | F | 64 | 179–180 | fumarate | MeOH/EtOH/ether |
| 219 | Me | CH₂CH₂–(3-furyl) | Ph | H | F | 32 | 169–171 | fumarate | MeOH/EtOH/ether |

TABLE A-continued

| Example No. | R² | R³ | R⁵ | R⁶ | Method | Yield % | Melting Range | Salt | Recrystallized From |
|---|---|---|---|---|---|---|---|---|---|
| 220 | Me | CH=CH—(4-Cl-C₆H₄) | Ph | H | F | 32 | 219–222 | fumarate | MeOH/EtOH/ether |
| 221 | Bzl | CH₂CH₂Ph | Ph | H | F | 13 | 137–138 | fumarate | EtOH/EtOAc |
| 222 | Me | CH₂CH₂Ph | 1-naphthyl | H | D | 6 | 268–270 | HCl.¼H₂O | MeOH/THF/ether |
| 223 | Bzl | CH=CH-Ph | Ph | H | F | 39 | 197–199 | HCl | THF/ether |
| 224 | Me | CH=CH—(4-OMe-C₆H₄) | Ph | H | F | 28 | 207–208 | fumarate | EtOH |
| 225 | Me | CH=CH—(4-NO₂-C₆H₄) | Ph | H | F | 30 | 230–232 | fumarate.H₂O | MeOH/EtOH/ether |
| 226 | Me | CH₃—C=C(CH₃)Ph* | Ph | H | F | 14 | 207–209 | fumarate | MeOH/ether |
| 227 | Me | CH₂CH₂Ph | cyclohexyl | H | F | 53 | 215–216 | fumarate | MeOH/ether |
| 228 | Me | CH₂CH₂—(4-Cl-C₆H₄) | (4-Cl-C₆H₄) | H | F | 39 | 155–157 | fumarate | MeOH/ether |
| 229 | Me | CH₂CH₂—(4-OMe-C₆H₄) | (4-OMe-C₆H₄) | H | F | 66 | 154–156 | fumarate | MeOH/EtOH/ether |

TABLE A-continued $$\begin{array}{c} \underset{R^6}{\overset{NHR^2}{\diagup}} \underset{NH_2}{\overset{}{\diagdown}} \xrightarrow{+R^3C(OR^{12})\atop R^3C(NH)OR^{12}\atop \text{or}\atop R^3COOR^{12}} \underset{R^6}{\overset{N\diagdown\underset{R^3}{\overset{R^2}{\diagup}}\diagup N}{\diagup}} \end{array}$$

| Example No. | $R^2$ | $R^3$ | $R^5$ | $R^6$ | Method | Yield % | Melting Range | Salt | Recrystallized From |
|---|---|---|---|---|---|---|---|---|---|
| 230 | Me | cyclohexyl-CH | Ph | H | F | 34 | 217–218 | fumarate | MeOH/ether |
| 231 | Me | C≡C-Ph | Ph | H | F | 5 | 223–225 | HCl.H$_2$O.½EtOH | EtOH/ether |
| 232 | Me | CH=CH-(4-pyridyl) | Ph | H | F | 18 | 243–245 | 2HCl.5/4 H$_2$O | MeOH/THF/ether |
| *mixture of isomers | | | | | | | | | |
| 233 | Me | CH=CH-(4-Cl-Ph) | 4-Cl-Ph | H | F | 54 | 233–234 | fumarate | MeOH/ether |
| 234 | Me | CH=CH-Ph | 4-Cl-Ph | H | F | 64 | 229–231 | fumarate | MeOH/ether |
| 235 | Ph | CH$_2$CH$_2$Ph | Me | H | F | 30 | 207–209 | HCl.¼H$_2$O | THF/ether |
| 236 | Me | cyclopropyl-Ph | Ph | H | F | 86 | 205–207 | fumarate.4/5 H$_2$O | MeOH/ether |
| 237 | Me | 2-thienyl | Ph | H | F | 47 | 137–139 | free base | MeOH |

TABLE A-continued

| Example No. | R² | R³ | R⁵ | R⁶ | Method | Yield % | Melting Range | Salt | Recrystallized From |
|---|---|---|---|---|---|---|---|---|---|
| 238 | Me | 2-furyl | Ph | H | F | 37 | 110–112 | free base | MeOtBu/hexane |
| 239 | Me | 2-MeO-C₆H₄-CH₂CH₂ | 4-MeO-C₆H₄ | H | F | 98 | 196–198 | fumarate | MeOH/MeCN/ether |
| 240 | Me | 2-MeO-C₆H₄-CH=CH | 4-MeO-C₆H₄ | H | F | 16 | 204–205 | fumarate | MeOH/ether |
| 241 | Me | 4-pyridyl-CH₂CH₂ | Ph | H | F | 45 | 241–243 | 2 HCl | MeOH/MeCN/THF |
| 242 | Me | 3-NO₂-C₆H₄-CH=CH | Ph | H | F | 54 | 209–210 | fumarate | EtOH/ether |

TABLE A-continued $$\underset{R^6}{\overset{NHR^2}{\underset{NH_2}{\bigcirc}}}\overset{+R^3C(OR^{12})}{\underset{R^3COOR^{12}}{\xrightarrow{R^3C(NH)OR^{12}}}} R^6\overset{R^2}{\underset{N}{\bigcirc}}\overset{R^3}{\underset{R^5}{N}}$$

| Example No. | R² | R³ | R⁵ | R⁶ | Method | Yield % | Melting Range | Salt | Recrystallized From |
|---|---|---|---|---|---|---|---|---|---|
| 243 | Me | 2-methylpyridin-6-yl-CH₂CH₂— | Ph | H | F | 52 | 235–237 | 2HCl·½H₂O | MeOH/ether |
| 244 | Me | (4-methylphenyl with NO₂) | Ph | H | F | 34 | 145–150 | fumarate | MeOH/ether |
| 245 | Me | 4-NO₂-C₆H₄-CH₂CH₂— | Ph | H | E | 91 | 123–125 | HCl·½EtOH | EtOH/ether |
| 246 | Me | 4-Cl-C₆H₄-CH₂CH₂— | 4-MeO-C₆H₄— | H | F | 71 | 191–193 | fumarate | MeOH/MeCN/ether |
| 247 | Me | 2-NO₂-C₆H₄-CH₂CH₂— | Ph | H | E | 66 | 234–236 | HCl | MeOH/ether |
| 248 | Me | CH₂CH₂Ph | Ph | 8-NO₂ | G | 88 | 241–242 | HCl | MeOH/ether |
| 269 | Me | 4-SO₂NEt₂-C₆H₄-CH₂CH₂— | Ph | H | F | 54 | 171–173 | HCl | EtOH/ether |

TABLE A-continued

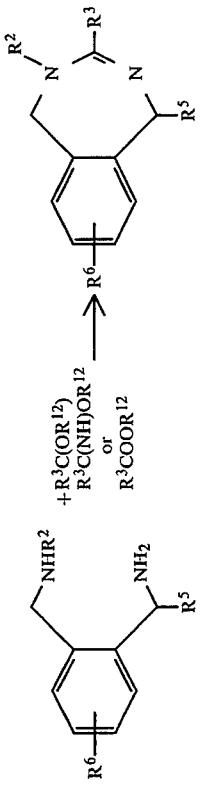

| Example No. | R² | R³ | R⁵ | R⁶ | Method | Yield % | Melting Range | Salt | Recrystallized From |
|---|---|---|---|---|---|---|---|---|---|
| 276 | CH₂CH₂-(4-NO₂-C₆H₄) | Et | Ph | H | E | 64 | 222-224 | HCl | MeCN/THF |
| 288 | Me | CH₂O-(4-NHSO₂Me-C₆H₄) | Ph | H | F1 | 70 | 183-184 | HCl | MeOH/ether |
| 288A | | | | | F2 | — | 234-235 | fumarate (−)-isomer[a] | MeOH |
| 288B | | | | | F2 | 59 | 234-235 | fumarate (+)-isomer[bn] | MeOH/ether |
| 288C | | | | | F3 | 59 | 195-196 | free base (+)-isomer | EtOAc/CH₂Cl₂/EtOH |
| 288D | | | | | | — | 234.5-235 | fumarate (+)-isomer | MeOH |
| 288E | | | | | | — | 171-177 | HCl.1/5EtOH (+)-isomer | EtOH |
| 288F | | | | | | — | 148.5-150 | CH₃SO₃H.½EtOH (+)-isomer | — |
| 288G | | | | | | — | 143-145.5 | CH₃SO₃H.½4/3H₂O (+)-isomer | MeOH |
| 288H | | | | | | — | 174.5-176 | HCl.H₂O (+)-isomer | — |
| 293 | Me | CH₂O-(4-NHSO₂Me-C₆H₄) | 4-Cl-Ph | H | F1 | 54 | 257-258 (dec) | HCl | MeOH/Et₂O |
| 293A | | | | | F2 | 44 | 243-243.5 | HCl (+)-isomer[c] | EtOH/acetone |

TABLE A-continued

[Reaction scheme: structure with NHR² and NH₂/R⁵ groups on benzene ring with R⁶ + R³C(OR¹²), R³C(NH)OR¹², or R³COOR¹² → cyclized product with R², R³, R⁵, R⁶]

| Example No. | R² | R³ | R⁵ | R⁶ | Method | Yield % | Melting Range | Salt | Recrystallized From |
|---|---|---|---|---|---|---|---|---|---|
| 293B | Me | [4-(CH₂O-C₆H₄-NHSO₂Me)] | 4-Cl-Ph | H | F2 | 47 | 244-244.5 | HCl (−)-isomer[d] | EtOH/acetone |
| 295 | Me | Me | 4-MeO-Ph | H | E1 | 58 | 138.5-139 | free base | EtOAc/hexane |
| 298 | Me | [4-(CH₂O-C₆H₄-NHSO₂Me)] | 4-Cl-Ph | H | F2 | 71 | 157-161 | HCl.1/4-5/4 H₂O | MeOH/CH₃CN/Et₂O |
| 302 | Me | [4-(CH₂S-C₆H₄-NHSO₂Me)] | 4-Cl-Ph | H | F2 | 16 | 238-239 | HCl | MeOH/CH₃CN/Et₂O[e] |
| 302A | Me | [4-(CH₂S-C₆H₄-NHSO₂Me)] | 4-Cl-Ph | H | F3 | 15 | 200-202 | HCl (+)-isomer | MeOH |
| 302B | Me | [4-(CH₂S-C₆H₄-NHSO₂Me)] | 4-Cl-Ph | H | F3 | 66 | 203-204 | HCl (−)-isomer | EtOH/CH₂Cl₂ |
| 305 | Me | [4-(CH₂O-C₆H₄-NHSO₂Me)] | 4-SCH₃-Ph | H | F2 | 64 | 206.5-209.5 | HCl.1/4-3/2 H₂O | MeOH/Et₂O |
| 305A | | | | | F3 | 47 | 128-136 | fumarate (+)-isomer | — |
| 305B | | | | | | — | 184-186 | HCl | EtOH/CH₃CN |
| 305C | | | | | F3 | — | 136-138 | fumarate (−)-isomer | — |

TABLE A-continued $$\begin{array}{c}\text{NHR}^2\\\text{[structure]}\\\text{NH}_2\\\text{R}^5\end{array} + \begin{array}{c}\text{R}^3\text{C(OR}^{12})\\\text{R}^3\text{C(NH)OR}^{12}\\\text{or}\\\text{R}^3\text{COOR}^{12}\end{array} \longrightarrow \text{[product structure with R}^2,\text{R}^3,\text{R}^5,\text{R}^6\text{]}$$

| Example No. | R² | R³ | R⁵ | R⁶ | Method | Yield % | Melting Range | Salt | Recrystallized From |
|---|---|---|---|---|---|---|---|---|---|
| 305D | | | | | | — | 221–222.5 | HCl (−)-isomer | EtOH/CH₃CN/Et₂O |
| 306 | Me | CH₃ | 4-SCH₃-Ph | H | E1 | 94 | 122–135 | free base | MeOtBu |
| 312 | Me | ![structure (CH₂)₂-C₆H₄-NHSO₂Me] | 2,4-(F)₂-Ph | H | F3 | 72 | 202–204 | free base.1/5 EtOH | EtOH |
| 312A | | | | | F3 | 41 | 198–200 | HCl | acetone/MeOH |
| 312B | | | | | | — | 114–118 | free base(f) (−)-isomer | EtOH |
| 312C | | | | | | — | 138–148 | HCl (−)-isomer | — |
| 312D | | | | | F3 | 58 | 111–115 | free base(g) (+)-isomer | EtOH |
| 312E | | | | | | — | 134–143 | HCl (+)-isomer | — |
| 313 | Me | Me | 2,4-(F)₂-Ph | H | E2 | 64 | 161–161.5 | free base | MeOtBu/EtOAc |
| 329 | Me | CH₂O–![Ph-NHSO₂Me] | 4-CH₃–SO₂Ph | H | F2 | 18 | 275–277 | HCl | EtOH/MeOH(h) then EtOH/MeOH/Et₂O then MeOH/CH₃CN/Et₂O |
| 330 | Me | CH₂NHSO₂Ph | Ph | H | D1 | 58 | 175–180 | HCl | EtOH/CH₃CN/THF/Et₂O then EtOH/THF/Et₂O then CH₃CN/MeOH |
| 333 | Me | (CH₂)₂–![Ph-NHSO₂CF₃] | Ph | H | F2 | 69 | 287–287.5 | free base | HOAc/MeOH |

TABLE A-continued $$\begin{array}{c}\text{NHR}^2\\\text{NH}_2\\R^5\end{array} \xrightarrow[\substack{\text{or}\\R^3COOR^{12}}]{+R^3C(OR^{12})\\R^3C(NH)OR^{12}} R^6 \longrightarrow \begin{array}{c}R^2\\N\\R^3\\N\\R^5\end{array}$$

| Example No. | $R^2$ | $R^3$ | $R^5$ | $R^6$ | Method | Yield % | Melting Range | Salt | Recrystallized From |
|---|---|---|---|---|---|---|---|---|---|
| 336 | (CH$_2$)$_2$-4-pyridinyl | 4-NHSO$_2$Me-C$_6$H$_4$-OCH$_2$- | 4-Cl-Ph | H | F2 | — | 127–131 | free base[f] | — |
| 339 | Me | 3-CH$_3$,4-NHSO$_2$Me-C$_6$H$_3$-OCH$_2$- | 4-Cl-Ph | H | F4 | 67 | 140–143 | HCl | Et$_2$O then CHCl$_3$/Et$_2$O |
| 340 | Me | 3-CH$_3$,4-NHSO$_2$Me-C$_6$H$_3$-OCH$_2$- | 4-Cl-Ph | H | F4 | 23 | 160–165 | HCl | — |
| 342 | Me | 3-CH$_3$O,4-NHSO$_2$Me-C$_6$H$_3$-OCH$_2$- | 4-Cl-Ph | H | F4 | 59 | 130–134 | HCl | — |
| 345 | Me | 3-Cl,4-NHSO$_2$Me-C$_6$H$_3$-OCH$_2$- | 4-Cl-Ph | H | F5 | 71 | 155–170 (dec) | HCl | EtOAc |
| 346 | Me | 4-NO$_2$-C$_6$H$_4$-CH$_2$CH$_2$- | Ph | H | E3 | 97.5 | amorphous foam | HCl (+)-isomer | EtOH/CH$_2$Cl$_2$/ether |

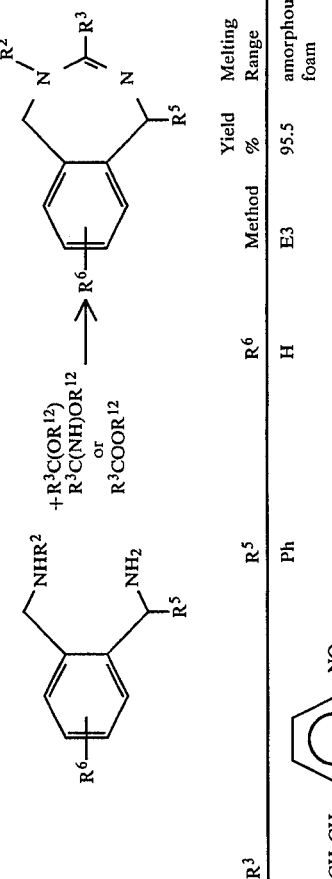

TABLE A-continued $$\underset{R^6}{\overset{NHR^2}{\underset{NH_2}{\bigcirc}}}\overset{+R^3C(OR^{12})}{\underset{R^3COOR^{12}}{\overset{R^3C(NH)OR^{12}}{\longrightarrow}}}\underset{R^6}{\overset{R^2}{\underset{N}{\bigcirc}}\overset{R^3}{\underset{R^5}{N}}}$$

| Example No. | R² | R³ | R⁵ | R⁶ | Method | Yield % | Melting Range | Salt | Recrystallized From |
|---|---|---|---|---|---|---|---|---|---|
| 371 | CH₂CH₂OCH₃ | ![NHSO₂Me-phenyl]—CH₂O— | 4-Cl-Ph | H | F2 | 50 | 125–130 | HCl[k] | — |
| 376 | Me | ![NHSO₂Me-phenyl]—CH₂O— | 4-iPr-Ph | H | F2 | 40 | 246–249 | HCl | MeOH/Et₂O |
| 377 | Me | ![NHSO₂Me-phenyl]—CH₂O— | 4-iPr-Ph | H | F2 | 41 | 267–268 | HCl | CH₃CN |
| 381 | Me | (pyridin-2-yl)—(CH₂)₂— | Ph | H | F7 | 49 | 215–218 | 2 HCl | EtOH/CH₃CN/ Et₂O(2X)[l] then CH₃CN/EtOH/THF/ Et₂O then CH₃CN/MeOH/THF (3X) |
| 383 | Me | (pyridin-3-yl)—(CH₂)₂— | Ph | H | F7 | 71.5 | 145–152 | 2 HCl | CH₃CN/EtOH/THF[m] then MeOH/CH₃CN/THF |
| 385 | Me | (pyridin-4-yl)— | Ph | H | F1 | 65 | 202–205 | fumarate | MeOH/EtOH/Et₂O[n] then MeOH/Et₂O |

TABLE A-continued

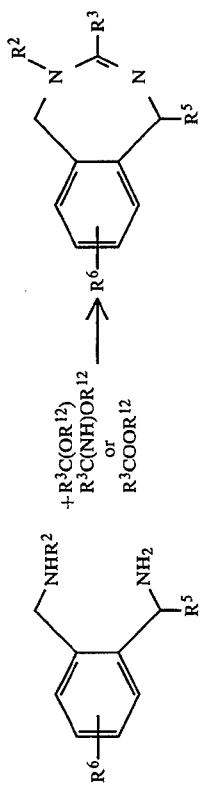

| Example No. | R² | R³ | R⁵ | R⁶ | Method | Yield % | Melting Range | Salt | Recrystallized From |
|---|---|---|---|---|---|---|---|---|---|
| 388 | Me | 4-(NHSO₂Me)-Ph-CH₂O- | 3,4-(Cl)₂-Ph | H | F2 | — | 181–186 | HCl | MeOH/Et₂O (2X) |
| 391 | Me | Ph-(CH₂)₂- | 3-CH₃SO₂-NH-4-Cl-Ph | H | D | 56 | 226–228 | 1/2 fumarate | MeOH/Et₂O(o) |
| 392 | Me | 4-pyridyl- | 4-Cl-Ph | H | F2 | 41 | 202–204 | 3/2 fumarate | MeOH/CH₃CN/Et₂O |
| 393 | Me | 4-(NHSO₂Me)-Ph-CH₂O- | —CH₂-Ph | H | F2 | 48 | 245.5–247 | HCl | MeOH/CH₃CN/Et₂O then MeOH |
| 395 | Me | 4-pyridyl-(CH₂)₂- | 4-Cl-Ph | H | F1 | 64 | 158–160 | 3/2 fumarate | MeOH/EtOH/THF/Et₂O(n) then MeOH/CH₃CN |
| 396 | Me | 4-(NHSO₂Me)-Ph-CH₂O- | 4-F-Ph | H | F8 | 26 | 172–175 | HCl | MeOH/CH₃CN/Et₂O |

TABLE A-continued $$\underset{R^6}{\overset{NHR^2}{\underset{NH_2}{\bigvee}}} \xrightarrow{+ R^3C(OR^{12}) \atop R^3C(NH)OR^{12} \atop \text{or} \atop R^3COOR^{12}} \underset{R^6}{\overset{R^2}{\underset{N}{\bigvee}} \overset{R^3}{\underset{R^5}{\bigvee}}}$$

| Example No. | R² | R³ | R⁵ | R⁶ | Method | Yield % | Melting Range | Salt | Recrystallized From |
|---|---|---|---|---|---|---|---|---|---|
| 397 | Me | (CH₂)₂-[4-pyridyl] | 4-F-Ph | H | F8 | 21 | 174–176.5 | fumarate | — |
| 398 | Me | (CH₂)₂-[4-pyridyl] | 4-CH₃O-Ph | H | F7 | 68 | 136–139 | 3/2 fumarate | EtOH/Et₂O then MeOH/CH₃CN |
| 399 | Me | (CH₂)₂-[4-(NHSO₂Me)-Ph] | 3,4-(Cl)₂-Ph | H | F2 | 53 | 199–201.5 | HCl | MeOH/CH₃CN/Et₂O then EtOH/MeOH then CH₃CN/Et₂O |
| 402 | Me | (CH₂)₂-[4-(NHSO₂Me)-Ph] | 2,4-(Cl)₂-Ph | H | F2 | 57 | 180–183 | HCl | MeOH/EtOH/Et₂O then EtOH/MeOH |
| 403 | Me | CH₂O-[4-(NHSO₂Me)-Ph] | 2,4-(Cl)₂-Ph | H | F2 | 29 | 203.5–206 | free base.¼EtOH | CH₂Cl₂/EtOH |
| 406 | Me | CH₂O-[4-(NHSO₂Me)-Ph] | 3-Cl-4-CH₃O-Ph | H | F2 | — | 207–210 | HCl | EtOH/MeOH(q) then MeOH/CH₃CN/Et₂O (3X) |

TABLE A-continued

[Reaction scheme: benzene ring with CH₂NHR² and CH(NH₂)R⁵ substituents and R⁶ + R³C(OR¹²) or R³C(NH)OR¹² or R³COOR¹² → benzene-fused diazepine ring with R², R³, R⁵, R⁶ substituents]

| Example No. | R² | R³ | R⁵ | R⁶ | Method | Yield % | Melting Range | Salt | Recrystallized From |
|---|---|---|---|---|---|---|---|---|---|
| 409 | Me | (CH₂)₂–C₆H₄–NHSO₂Me | 4-CH₃-Ph | H | F2 | 53 | 247–249 | HCl | MeOH/Et₂O/CH₃CN[r] |
| 410 | Me | CH₂O–C₆H₄–NHSO₂Me | 4-CH₃-Ph | H | F2 | 65.5 | 202–206 | HCl | CH₃CN/EtOH/Et₂O[s] then MeOH/CH₃CN/Et₂O |
| 414 | Me | CH₂O–C₆H₄–NHSO₂Me | 2,4-(Et)₂-Ph | H | F2 | 19 | 162–166 | HCl | CH₃CN/Et₂O[t] |
| 415 | Me | (CH₂)₂–C₆H₄–NHSO₂Me | 2,4-(Et)₂-Ph | H | F2 | 34 | 162–166 | HCl | CH₃CN/Et₂O/THF[u] |
| 422 | Me | (CH₂)₂–C₆H₄–NHSO₂Me | 3-Cl-4-CH₃O-Ph | H | F2 | 36 | 232–234 | HCl | MeOH/CH₃CN/Et₂O[v] then MeOH/EtOH/Et₂O |

TABLE A-continued

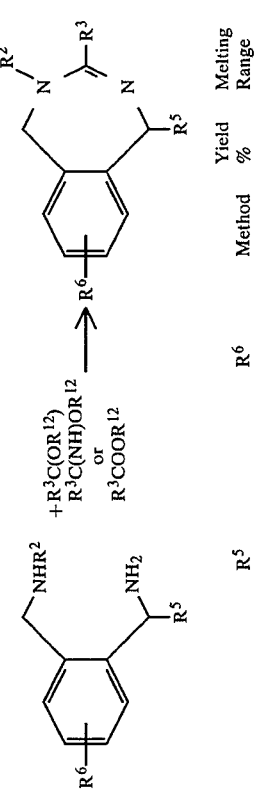

| Example No. | R² | R³ | R⁵ | R⁶ | Method | Yield % | Melting Range | Salt | Recrystallized From |
|---|---|---|---|---|---|---|---|---|---|

(a)[α]_D^25 = −161° (C = 0.73, MeOH).
(b)[α]_D^25 = +169° (C = 1.01, MeOH).
(c)[α]_D^25 = +187° (C = 1.045, EtOH).
(d)[α]_D^25 = −185° (C = 1.04, EtOH).
(e)The HCl salt was purified by column chromatography on silica eluting with CHCl₃/isopropanol/trifluoroacetic acid (82/15/3) prior to being recrystallized.
(f)[α]_D^25 = −89° (C = 0.512, CHCl₃).
(g)[α]_D^25 = +90° (C = 0.5, CHCl₃).
(h)Prior to recrystallization (3X) the product was purified by column chromatography on silica eluting with CHCl₃/10–15% EtOH/3–4% trifluoroacetic acid.
(i)Free base was purified by column chromatography on silica eluting with CHCl₃/MeOH/trifluoroacetic acid (80/17/3) to (74.6/22.4/3).
(j)Free base was purified by column chromatography on silica eluting with CH₂Cl₂/EtOH/CF₃CO₂H (67/30/3) prior to conversion to the hydrochloride salt and recrystallization of the salt from ethanol.
(k)Free base was purified by column chromatography on silica eluting with CHCl₃/iPrOH/CF₃CO₂H (82/15/3) to (77/20/3) prior to conversion of the free base to the hydrochloride salt.
(l)Free base was purified by column chromatography on silica eluting with tBuOMe/1–4% isopropylamine.
(m)Free base was purified by column chromatography on silica eluting with 75% tBuOMe/25% CH₂Cl₂/2% isopropylamine and then a second silica column eluting with tBuOMe/2–4% isopropylamine.
(n)Note: filtrate was acidified with fumaric acid to afford fumarate salt rather then with ethereal HCl to afford HCl salt.
(o)Reaction was worked up by filtering the reaction mixture, concentrating the filtrate in vacuo, extracting with saturated Na₂CO₃/CH₂Cl₂ and collecting the solid thus formed by filtration.
(p)Free base was purified by column chromatography on silica eluting with tBuOMe/2–4% CH₂Cl₂/2–4% isopropylamine.
(q)Free base was purified by column chromatography on silica gel eluting with CHCl₃/10–15% EtOH/3% CF₃CO₂H then CHCl₃/10% MeOH/3% CF₃CO₂H prior to conversion of the free base to the hydrochloride salt.
(r)Note: product precipitated directly out of the organic phase and was collected by filtration.
(s)HCl salt was purified by column chromatography on silica eluting with CHCl₃/10–15% EtOH/2–3% CF₃CO₂H prior to second recrystallization.
(t)Prior to recrystallization, the salt was purified by column chromatography on silica eluting with CHCl₃/10–15% EtOH/2–3% CF₃CO₂H then CHCl₃/5–15% MeOH/2–3% CF₃CO₂H, the salt was then converted into the free base, back into the HCl salt and then purified by column chromatography as above.
(u)Prior to recrystallization the salt was purified by column chromatography on silica eluting with CHCl₃/10–15% EtOH/2–3% CF₃CO₂H, the salt was then converted into the free base and then back into the HCl salt by treatment with ethanolic HCl.
(v)Prior to recrystallization, the HCl salt was purified by column chromatography on silica eluting with CHCl₃/10% MeOH/3% CF₃CO₂H; followed by a second silica column eluting with CHCl₃/10% EtOH/3% CF₃CO₂H; followed by passing the salt through an alumina column eluting with CH₂Cl₂/5% MeOH.

TABLE J

[Reaction scheme: A ring with CH₂NHCH₃ and CH(Ph)NH₂ substituents → cyclized product with N-CH₃ and N-C(R³)= forming ring fused to A, with Ph on the CH]

| Example No. | A | R³ | Method | Yield % | Melting Range | Salt | Recrystallized From |
|---|---|---|---|---|---|---|---|
| 200 | cyclohexane (cis) | CH₂CH₂Ph | E | 32 | 190–192 | fumarate | THF/MeCN |
| 201 | thiophene | CH₂CH₂Ph | E | 67 | 180–181 | fumarate | EtOH/ether |
| 202 | thiophene | CH₂CH₃ | E | 61 | 191–192 | fumarate | EtOH/ether |
| 203 | thiophene | CH=CH-(2-furyl) | F | 20 | 184–185 | fumarate | MeOH/MeCN (after chromatography on S$_i$O$_2$ with 4:49:3 hexane/tBuOMe/IPA) |
| 204 | thiophene | CH₂SO₂Ph | F | 55 | 132–135 | fumarate | EtOH/ether |
| 372 | thiophene | CH₂O-C₆H₄-NHSO₂CH₃ | F2 | 47 | 168–170 | HCl·H₂O | MeOH/ether[a] |
| 373 | thiophene | (CH₂)₂-C₆H₄-NHSO₂CH₃ | F2 | 42 | 232–234 | HCl | EtOH/ether[b] |

[a] A small portion of the HCl salt was obtained directly from the free base by treatment with ethereal HCl and collection of the salt by filtration. The remainder was obtained by concentration of the filtrates in vacuo, purification of the residue by column chromatography on silica eluting with CHCl₃/iPrOH/CF₃CO₂H (67/30/3) to (74/23/3) and treatment of the residue with ethereal HCl and recrystallization of the HCl salt thus obtained from EtOH/ether.

[b] HCl salt was first purified by column chromatography on silica eluting with CHCl₃/EtOH/CF₃CO₂H (82/15/3) to (77/20/3), prior to recrystallization.

TABLE K

| Example No. | R³ | Method | Yield % | Melting Range | Salt | Recrystallized From |
|---|---|---|---|---|---|---|
| 205 | CH₂CH₂Ph | F | 35 | 255–256 | HCl.1/2 H₂O | MeOH/ether |
| 206 | CH=CHPh | F | 17 | amorphous | HCl.1/2 H₂O | EtOAc |

General Method A

The appropriate diamine and five to seven equivalents of the corresponding triethylorthoester were stirred at room temperature while 0.4–0.5 mL of acetic acid per mmol of diamine were added in one portion. The mixture was stirred at reflux for 2–12 hours or stirred at room temperature for 2–72 hours. The reaction was diluted with ethyl acetate, washed with 2N sodium hydroxide and extracted into three portions of 2N HCl. The HCl extracts were combined, washed twice with ether, made basic with excess 35% sodium hydroxide and extracted into three portions of ether. The ether extracts were combined, dried over magnesium sulfate and the solvent removed in vacuo. The free base or the salt was recrystallized as shown in Table A.

General Method B

The diamine was added to two equivalents of potassium acetate or a catalytic amount of potassium acetate in 0.8–1.2 mL of acetic acid per mmol of diamine. The mixture was stirred at room temperature and from two to five equivalents of the appropriate triethylorthoester were added. The reaction was stirred at room temperature for 18–72 hours and stripped in vacuo. The product was worked up as described for General Method A.

General Method C

The dihydrochloride of the diamine was dissolved in 1–3 mL of acetic acid per mmol of diamine and about 2.0 to 2.5 equivalents of sodium acetate were added. The mixture was stirred for about ten minutes at room temperature, and three to five equivalents of the appropriate triethylorthoester were added. The mixture was stirred at room temperature for 2–48 hours and stripped in vacuo. The reaction was worked up as described in General Method A.

General Method D

The diamine dihydrochloride and two to three equivalents of the appropriate methoxyimine hydrochloride were dissolved in 2–6 mL of methanol per mmol of diamine. The mixture was stirred, and two equivalents of sodium acetate were added. After 2–18 hours the solvent was removed in vacuo and the product worked up as described in General Method E.

General Method D1

The procedure was the same as that described hereinabove in General Method D except that the appropriate ethoxyimine hydrochloride was used and the reaction mixture was worked up as follows. The reaction mixture was filtered, washed with methanol, concentrated in vacuo and extracted with aqueous Na₂CO₃/CH₂Cl₂. The organic layer was separated, washed with water, then aqueous Na₂CO₃ and then brine and the solvent was dried over Na₂SO₄ and concentrated in vacuo. The residue was converted into an appropriate salt which was purified as shown in Table A.

General Method E

The diamine dihydrochloride, 1.3–3.0 equivalents of the appropriate trimethyl- or triethylorthoester and 1.0–1.8 equivalents of sodium acetate were combined in about 3 to 6 mL of isopropyl acetate per mmol of the diamine. The mixture was refluxed for 3–18 hours. The reaction was cooled, washed with two portions of 2N sodium hydroxide and dried over sodium sulfate. The solvent was removed in vacuo and either the salt or the free base was purified from the residue as shown in Table A.

General Method E1

The diamine dihydrochloride, methanol, 2.0 equivalents of the appropriate trimethyl or triethylorthoester and 1.75–1.9 equivalents of sodium acetate were combined and stirred at about 25° C. to reflux for 3–24 hours. The solvent was removed in vacuo, and the residue was extracted with CH₂Cl₂ or a mixture of tert-butylmethyl ether/CH₂Cl₂ (1/1) and the extract was washed with 1–2N NaOH. The mixture was dried over Na₂SO₄, filtered and the filtrate was concentrated in vacuo to afford the free base which was purified by recrystallization as shown in Table A.

General Method E2

The procedure was substantially similar to that described in General Method E1 except that the reaction mixture was worked-up as follows. The reaction mixture was cooled, filtered, and the filtrate was concentrated in vacuo. The residue was partitioned between dilute HCl (1N) and ether. The aqueous layer was separated, basified with 35% NaOH and extracted with tert-butylmethyl ether/CH₂Cl₂. The aqueous layer was saturated with brine and again extracted with tert-butylmethyl ether/CH₂Cl₂ and the combined organic extracts were washed with brine, dried over Na₂SO₄ and concentrated in vacuo. The residue thus obtained was then purified by recrystallization as shown in Table A.

General Method E3

The procedure was similar to that described in General Method E except that the reaction mixture was worked up as follows. The reaction mixture was treated with water, a sufficient amount of 2N NaOH or 35% NaOH to basify the solution, ether, and CH₂Cl₂. The organic layer was separated and the aqueous layer was saturated with sodium chloride and extracted with ether. The organic layers were combined, washed with brine and dried over $Na_2SO_4$ and concentrated in vacuo and either the salt or the free base was purified from the residue thus obtained as illustrated in Table A.

General Method F

To the diamine dihydrochloride, slurried in about 3 mL of toluene per mmol of diamine, was added dropwise at 0° under nitrogen 2.1 equivalents of 2M trimethylaluminum in toluene. The reaction was allowed to come to room temperature and stirred for 2 hours, then 1.25 to 1.50 equivalents of the appropriate methyl or ethyl ester were added. The reaction was refluxed 2 hours, cooled and quenched by the sequential addition of ice, methanol, dichloromethane and 2N NaOH. The aluminum salts were filtered off, the layers separated, washed with more dichloromethane, dried over sodium sulfate, stripped and crystallized as shown in Table A. Occasionally flash chromatography on silica gel with MeOtBu, optionally containing up to 2% isopropylamine, was necessary before crystallization.

General Method F1

To a slurry of the diamine dihydrochloride in about 3.5-5 mL of sulfolane per mmol of diamine was added dropwise at room temperature under nitrogen 3.1-4.5 equivalents of 2M trimethylaluminum in toluene. The reaction mixture was stirred at room temperature to 35° C. for 15-60 minutes and then 1.07-1.25 equivalents of the appropriate ethyl ester was added in one portion. The resulting solution was heated at about 95°-110° C. for 50 minutes to 2.5 hours, cooled and was poured into a mixture of water, Rochelle salt, $CH_2Cl_2$, 2N NaOH and ice. The organic layer was separated, and the aqueous layer was extracted with $CH_2Cl_2$. The organic layers were combined, washed with water containing Rochelle salt, and then with a $Na_2CO_3$ solution. The organic layer was dried over $Na_2SO_4$, filtered, and the filtrate was acidified with ethereal.HCl and evaporated to afford the product as the acid salt which was recrystallized as shown in Table A.

General Method F2

The procedure was the same as that described hereinabove in General Method F1 except that the reaction mixture was worked up by diluting the cooled reaction mixture with $CH_2Cl_2$ and then quenching with a saturated Rochelle salt solution, water and a saturated $Na_2CO_3$ solution. After filtering the mixture through solka Flok, if necessary, the organic phase was separated, dried over $Na_2SO_4$ and concentrated in vacuo. The residue was then purified as such, or was converted into an appropriate salt by standard procedures which are well known in the art, and the salt was purified by recrystallization as shown in Table A.

General Method F3

The diamine dihydrochloride was stirred with about 6-12 mL of toluene per mmol of diamine under nitrogen, and 3.0-3.5 equivalents of 1M trisobutyl aluminum in toluene was added while maintaining the reaction temperature at about room temperature. The mixture was heated from about 60° C. to reflux for 15-20 minutes and then 1.0-1.2 equivalents of the appropriate ethyl ester was added. The mixture was heated to reflux for 1-4 hours and then was allowed to stand at room temperature overnight or was worked-up directly. The reaction mixture was poured into a mixture of a saturated Rochelle salt solution, ethyl acetate, $CH_2Cl_2$ (optional), saturated $Na_2C_{O3}$ solution and ice-water and the organic layer was separated. The aqueous layer was extracted with $CH_2Cl_2$ or ethyl acetate and the combined organic layers were washed with brine (optional), and dried over $Na_2SO_4$. The solvent was concentrated in vacuo and either the appropriate salt or the free base was purified from the residue as shown in Table A.

General Method F4

The diamine hydrochloride was stirred with about 5-6 mL of toluene per mmol of the diamine, optionally in the presence of about 2 mL of sulfolane per mmol of the diamine and 2.5-2.6 equivalents of 1M triisobutyl aluminum in toluene was added. The mixture was heated to reflux for 10-15 minutes and then about 1.3 equivalents of the appropriate ethyl ester was added. The reaction mixture was refluxed for 3-4 hours and then was cooled and diluted with $CH_2Cl_2$. The mixture was poured into a Rochelle salt solution, water was added and the mixture was stirred for 15-30 minutes. The mixture was filtered and the filtrate was concentrated in vacuo to afford the free base of the product which was purified by recrystallization as shown in Table A, or which was converted into an appropriate salt which was purified, where applicable, as shown in Table A.

General Method F5

The procedure was similar to that described in General Method F3, except that the reaction mixture was worked up by pouring the reaction mixture into a saturated Rochelle salt solution, adding water and ethyl acetate and then separating the organic layer. The organic layer was then washed with a saturated Rochelle salt solution ($2\times$), dried over $Na_2SO_4$ and concentrated in vacuo. The residue thus obtained was then purified, where necessary, as shown in Table A or it was converted into an appropriate salt by standard procedures which are well known in the art, and the salt was purified, where necessary, by recrystallization as shown in Table A.

General Method F6

The procedure was similar to that described in General Method F1, except the reaction was washed up as follows. The reaction mixture was quenched with a saturated Rochelle salt solution, then $CH_2Cl_2$ and finally saturated $Na_2CO_3$ was added. The phases were separated, the aqueous phase was extracted with $CH_2Cl_2$ and the organic layers were combined and dried over $Na_2SO_4$. The solvent was removed in vacuo and the residue was then purified as the free as shown in Table A or was converted into an appropriate salt by standard procedures and the salt was purified as shown in Table A.

General Method F7

To the diamine dihydrochloride in about 3-5 mL of toluene per mmol of diamine, was added dropwise at 0° C. under nitrogen 2.1 equivalents of 2M trimethylaluminum in toluene. The reaction mixture was brought to room temperature, stirred for about 2 hours and then 1.5 equivalents of the appropriate methyl ester was added. The reaction mixture was refluxed for about 45 minutes to 2.5 hours, cooled in an ice bath and then treated with 2N NaOH and Et₂O/CH₂Cl₂/MeOH (2/1/1) to (3.5/1.5/1). The mixture was stirred for about ½–1 hour, and was filtered through solka floc. The organic layer was separated, washed with brine and then 2N NaOH (optional) and the solvent was dried over Na₂SO₄ and concentrated in vacuo. The residue was purified by column chromatography on silica if necessary, and the residue was converted into an appropriate salt and recrystallized as illustrated in Table A.

General Method F8

The procedure was similar to that described in General Method F1 except that the reaction was worked up as follows. The reaction mixture was poured into a water/Rochelle salt/CH₂Cl₂ solution, and the mixture was filtered through solka floc. The filtrate layers were separated, the aqueous layer was extracted with CH₂Cl₂ and the combined organic layers were washed with water, a Rochelle salt solution and saturated Na₂CO₃. The solvent was dried over Na₂SO₄ and the solvent was removed in vacuo. The residue was passed through a plug of neutral alumina eluting with tBuO-Me/CH₂Cl₂ (1/1) and the residue thus obtained was converted into an appropriate salt by standard procedures which are well known in the art and the salt was purified by recrystallization as shown in Table A.

General Method G

The free base of the diamine, three equivalents of acetic acid and three equivalents of either the appropriate triethylorthoester or the hydrochloride of the appropriate ethoxyimine in 2–4 mL of methanol per mmol of diamine were stirred at room temperature for 18 hours. The solvent was removed in vacuo and the product treated as described in General Method A.

TABLE B

| Example No. | R² | R³ | Method | Yield % | Melting Range | Salt | Recrystallized From |
|---|---|---|---|---|---|---|---|
| 64 | Me | Et | C | 92 | 205–207 | HCl | MeOH/ether |
| 65 | Me | Me | C | 27 | 261–264 | HCl | MeOH/ether |
| 66 | Me | H | C | 32 | 244–245 | HCl | MeOH/ether |
| 67 | Me | nPr | C | 62 | 223–226 | HCl | MeOH/ether |
| 68 | Bzl | Et | C | 49 | 209–210 | HCl | EtOAc/HCl in ether |
| 69 | Bzl | H | H | 52 | 149–151 | H₂O | |
| 70 | Bzl | nPr | I | 20 | 211–212 | HCl | EtOAc/ether |
| 249 | Me | CH₂CH₂Ph | E | 78 | amorphous | HCl.3/5 H₂O | ether |

General Method H

The diamine dihydrochloride, 2.2 equivalents of sodium acetate and 1.5 equivalents of triethylorthoester were combined in 1.2 mL of isopropyl acetate per mmol of diamine and refluxed for four days. The solvent was removed in vacuo, the residue taken up in dichloromethane, the dichloromethane was washed two times with 2N sodium hydroxide and dried over magnesium sulfate. The solvent was removed in vacuo and the product chromatographed on silica gel eluting with 49:49:2 ethyl acetate/dichloromethane/diethylamine. The hydrochloride of the purified free base was formed by dissolving the free base in ethyl acetate and adding HCl in ether.

General Method I

The diamine dihydrochloride, 2.1 equivalents of sodium acetate, 3 equivalents of trimethylorthoester, and 5 equivalents of acetic acid were stirred together for seven days at room temperature. The workup was the same as that described for General Method H.

TABLE C

| Example No. | Nucleophile | R³ | Method | Yield* % | Melting Range | Salt | Recrystallized From |
|---|---|---|---|---|---|---|---|
| 71 | EtSH | —CH₂SEt | J | 35 | 267–269 | HCl | EtOH/ether |
| 59 | PhSO₂Na | —CH₂S(O)(O)—Ph | K | 31 | 246–248 | HCl | MeOH/ether |

TABLE C-continued

Reaction scheme: 3-(chloromethyl)benzodiazepine (with N-Me, CH₂Cl, N, Ph substituents) + Nucleophile → corresponding 3-R³ benzodiazepine

| Example No. | Nucleophile | R³ | Method | Yield* % | Melting Range | Salt | Recrystallized From |
|---|---|---|---|---|---|---|---|
| 72 | Me₂NH | —CH₂NMe₂ | K | 41 | 184–186 | fumarate | EtOH/ether |
| 73 | PhSH | —CH₂SPh | J | 12 | 196–197 | fumarate | MeOH/ether |
| 74 | piperidine (NH) | CH₂–N(piperidine) | K | 43 | 194–196 | fumarate | EtOH/ether |
| 75 | BzlNHCH₃ | CH₂N(Bzl)(Me) | K | 23 | 102–104 | fumarate | EtOH/ether |
| 76 | HN(piperazine)N—Me | CH₂–N(piperazine)N—Me | K | 52 | 233–235 | 2 fumarate | MeOH/ether |
| 77 | HN(morpholine)O | CH₂N(morpholine)O | K | 28 | 206–208 | fumarate | MeOH/ether |
| 78 | Et₂NH | CH₂NEt₂ | K | 24 | 133–135 | 1.5 fumarate 0.25 EtOH | EtOH/ether |
| 79 | CH₃O—C₆H₄—SH | CH₂S—C₆H₄—OCH₃ | J | 16 | 208–210 | HCl | MeCN/ether |
| 80 | CH₃—C₆H₄—SO₂Na | CH₂SO₂—C₆H₄—CH₃ | K | 30 | 247–249 | HCl | EtOH/MeCN |
| 81 | Cl—C₆H₄—SO₂Na | CH₂SO₂—C₆H₄—Cl | K | 10 | 214–217 | HCl | MeOH/MeCN |

*yield calculated over two steps from the diamine.

General Method J

The 3-chloromethylbenzodiazepine was dissolved in three mL of acetonitrile per mmol of benzodiazepine and added to 1.0–1.7 equivalents of the thiol plus 2.3 equivalents of milled potassium carbonate in three mL of acetonitrile per mmol of benzodiazepine. The reaction was stirred at room temperature for 18 hours and filtered. The acetonitrile was removed in vacuo and the product worked up as described in General Method A.

General Method K

The 3-chloromethylbenzodiazepine and three equivalents of the appropriate amine or sodium sulfinate were combined in 1–5 mL of solvent per mmol of benzodiazepine and refluxed for 3–5 hours. The reactions with amines were run in chloroform; the reactions with sulfinate were run in methanol. The product was worked up as described in General Method A.

TABLE D

| Example No. | R2 | R3 | R4 | Electrophile | Method | Yield % | Melting Range | Salt | Recrystallized From |
|---|---|---|---|---|---|---|---|---|---|
| 82 | Me | Et | —CH$_2$COOEt | BrCH$_2$COOEt | L | 22 | 166–167 | fumarate | EtOH/ether |
| 83 | Me | Et | —CH(OH)CH$_2$CH$_3$ | CH$_3$CH$_2$CHO | M | 21 | 155 (d) | fumarate | EtOH/ether |
| 84 | Me | Et | —COOEt | ClCOOEt | L | 57 | 162 (d) | fumarate | EtOH |
| 85 | Me | Et | —C(O)Me | CH$_3$COCl | L | 22 | 184–185 | fumarate | EtOH |
| 86 | Me | Et | —CH$_2$CH=CH$_2$ | BrCH$_2$CH=CH$_2$ | L | 25 | 180–187 | fumarate | EtOH/ether |
| 87 | Me | Et | iPr | iPrI | L | 25 | 208–210 | fumarate | iPrOH |
| 88 | Me | Et | Et | EtI | L | 45 | 234–235 | fumarate | EtOH |
| 89 | CH$_2$-cyclopropyl | Me | Me | MeI | L | 56 | 107–108 | free base | ether/hexane |
| 90 | Me | Ph | Et | EtI | L | 80 | 126–127 | free base | tBuOMe/hexane |
| 91 | Me | Et | n-Pr | n-PrI | L | 50 | 199–202 | fumarate | EtOH/ether |
| 92 | iPr | Me | Me | MeI | L | 93 | 150–151<br>103–104 | maleate<br>free base | acetone/ether<br>hexane |
| 93 | iPr | Me | Et | EtI | L | 79 | 158–159<br>unrecorded | maleate<br>free base | acetone/ether<br>hexane |
| 94 | Me | Ph | Me | MeI | L | 40 | 130–132 | free base | hexane/CH$_2$Cl$_2$ |
| 95 | Me | Et | Me | MeI | L | 66 | 244–246 | fumarate | EtOH |
| 96 | Me | Me | Me | MeI | L | 61 | 228–230<br>115–116 | fumarate<br>free base | trit. iPrOH<br>hexane |
| 97 | Me | Me | CH$_2$OMe | ClCH$_2$OMe | L | 17 | 155–156 | free base | EtOAc/hexane |
| 299 | Me | Me | Me | MeI | L1 | 90 | 174–176 | free base | toluene/ethyl acetate/hexane |

TABLE E

Reaction scheme (header):

Structure showing ArCH2-N(R2)-C(=CH2R14)-N(R4)(CHPh-Ar) → (via 1) nBuLi, 2) Electrophile) → ArCH2-N(R2)-C(=CHR3)-N(R4)(CHPh-Ar)

| Example No. | R² | R³ | R⁴ | Electrophile | R¹⁴ | Method | Yield % | Melting Range | Salt | Recrystallized From |
|---|---|---|---|---|---|---|---|---|---|---|
| 98 | Me | —CH₂Cl | Me | C₂Cl₆ | H | L | 18 | 118–120 | free base | CH₂Cl₂/hex |
| 99 | Me | CH₂NMe₂ | Me | C₂Cl₃/Me₂NH | H | N | 51* | 89–90 | free base | Chromatog 9:1 hex/Et₂NH |
| 100 | Me | CH₂—N(imidazole) | Me | C₂Cl₆/HN(imidazole) | H | N | 17* | 144–145 | free base | CH₂Cl₂/hex |
| 101 | Me | —CH₂COOEt | Me | ClCOOEt | H | O | 12* | 100–102 | free base | CH₂Cl₂/hex |
| 102 | Me | —CH(COOEt)₂ | Me | ClCOOEt | H | L | 17* | 146–147 | free base | CH₂Cl₂/hex |
| 103 | Me | —CH₂-(4-Cl-C₆H₄) | Me | ClCH₂-(4-Cl-C₆H₄) | H | L | 48* | 149–151 | maleate hemihydrate | acetone |
| 103A | Me | —CH₂CH₂Ph | Me | BzlBr | H | L | 78 | 143–147 | HCl(+)isomer | H₂O |
| 103B | Me | —CH₂CH₂Ph | Me | BzlBr | H | L | 66 | 143–146 | HCl(−)isomer | H₂O |
| 104 | iPr | —CH₂CH₂-(4-Cl-C₆H₄) | Me | ClCH₂-(4-Cl-C₆H₄) | H | L | 86 | 173–175 | maleate | acetone/ether |
| 105 | CH₂-cyclopropyl | —CH₂CH₂-(4-Cl-C₆H₄) | Me | ClCH₂-(4-Cl-C₆H₄) | H | L | 70 | 189–191 | HCl | MeCN/acetone/ether |
| 106 | iPr | —CH₂CH(Ph) | Et | BzlBr | H | L | 88 | 160–162 | maleate | acetone/ether |
| 107 | Me | iPr | Me | MeI | Me | P | 40 | 223–225 | fumarate | EtOH |
| 108 | Me | CH₂NEt₂ | Me | C₂Cl₆/Et₂NH | H | N | 65 | 200–206 | 2HCl | MeCN/ether |

*over two steps

TABLE E-continued $$\text{R}^2\text{N-C(R}^3\text{)=N-C(R}^4\text{)(Ph)(C}_6\text{H}_4\text{)CH}_2\text{R}^{14} \xrightarrow{\text{1) nBuLi} \atop \text{2) Electrophile}}$$

(cyclic benzofused amidine structure with $R^2N$, $R^3$, $R^4$, Ph substituents)

| Example No. | R² | R³ | R⁴ | Electrophile | R¹⁴ | Method | Yield % | Melting Range | Salt | Recrystallized From |
|---|---|---|---|---|---|---|---|---|---|---|
| 109 | Me | CH₂N(morpholino) | Me | C₂Cl₆/HN(morpholino) | H | N | 15 | 137–140 | 2H₂SO₄ | MeOH/acetone |
| 110 | Me | —CH₂COPh | Me | PhCOOMe | H | L | 18 | 160–161 | free base | EtOAc/hex |
| 111* | Me | —CH(CH₃)CH₂Ph | Me | BzlBr | Me | L | 6 | 168–169 | maleate | MeCN/ether |
| 112* | Me | —CH(CH₃)CH₂Ph | Me | BzlBr | Me | L | 30 | 177–180 | maleate | MeCN |
| 113 | Me | —CH(NH₂)CH₂CHPh | Me | PhCH=NTMS | H | L | 80 | 222–256 | 2HCl | MeOH/ether |
| *diastereomeric pair | | | | | | | | | | |
| 114 | Me | —CH(OH)CH₂(4-pyridyl) | Me | 4-pyridine-CHO | H | M | 45* | 189–190 | fumarate | EtOH/ether |
| 115 | Me | —CH(OH)CH₂Ph | Me | PhCHO | H | M | 44* | 169–171 | maleate | EtOH/ether |
| 116 | Me | —CH₂CH₂(4-MeO-C₆H₄) | Me | 4-MeO-C₆H₄-CH₂Cl | H | L | 84* | 171–172 | maleate | acetone/ether |
| 117 | Me | CH₂SEt | Me | EtSSEt | H | L | 69* | 235–236 | HCl | Al₂O₃ Chromatog then ether |

*over two steps

TABLE E-continued
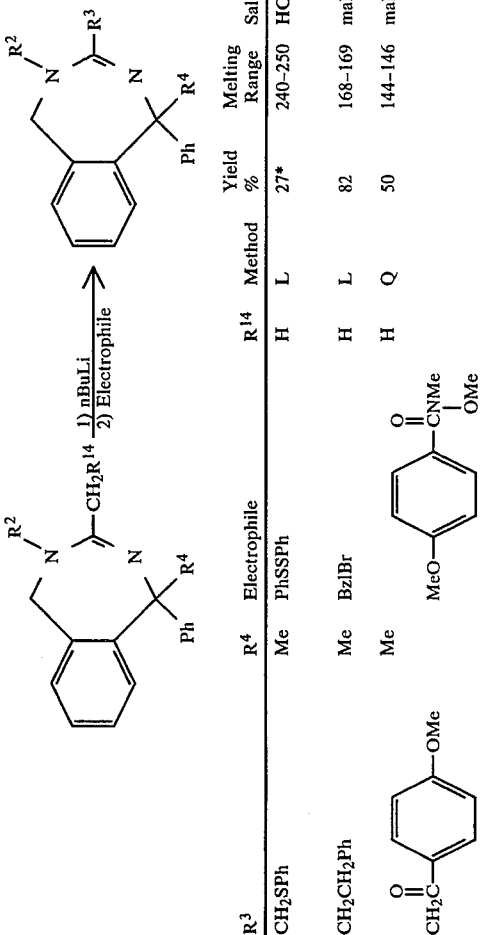
| Example No. | $R^2$ | $R^3$ | $R^4$ | Electrophile | $R^{14}$ | Method | Yield % | Melting Range | Salt | Recrystallized From |
|---|---|---|---|---|---|---|---|---|---|---|
| 118 | Me | CH$_2$SPh | Me | PhSSPh | H | L | 27* | 240-250 | HCl | SiO$_2$ EtOAc/MeOH/IPA then ether |
| 119 | Me | CH$_2$CH$_2$Ph | Me | BzlBr | H | L | 82 | 168-169 | maleate | MeCN/ether |
| 120 | Me | (4-MeO-C$_6$H$_4$-CO-CH$_2$-) | Me | (4-MeO-C$_6$H$_4$-C(=O)-N(Me)OMe) | H | Q | 50 | 144-146 | maleate | acetone/ether |
*over two steps

General Method L

The benzodiazepine in 3–7 mL of THF per mmol of benzodiazepine was stirred at −78° C. to −42° C. while 1.1 equivalent of N-butyllithium was added under nitrogen. The solution was stirred for one hour at −78° C., 1.1–1.3 equivalents of the appropriate electrophile were added, and the reaction was allowed to come to room temperature. The reaction was poured into 1N HCl, washed with ether, made basic, and extracted into ether. The combined ether layers were dried over potassium carbonate, filtered and the solvent removed in vacuo. The free base was recrystallized or a salt was prepared as shown in Table D.

General Method L1

The benzodiazepine in about 5.2 mL of THF per mmol of benzodiazepine was stirred at −78° C. while 1.05 equivalents of n-butyllithium was added under nitrogen. The mixture was stirred for 30 minutes at −78° C., then 1.25 equivalents of the appropriate electrophile was added and the reaction mixture was stirred at −78° C. for 30 minutes. The reaction was quenched at −78° C. with saturated ammonium chloride, warmed to room temperature and poured into a separatory funnel containing $CH_2Cl_2$/tert-butylmethyl ether (2/1), brine and 2N NaOH. The organic layer was removed, washed with brine, dried over $Na_2SO_4$, filtered and concentrated in vacuo. The free base was purified by recrystallization as shown in Table D.

EXAMPLE 265

1-(4-Chlorophenyl)-3-[2-(4-chlorophenyl)ethyl]-4,5-dihydro-1,4-dimethyl-1H-2,4-benzodiazepine (Formula Ia: $R^1$, $R^6$=H; $R^{2a}$, $R^{4b}$=Me;

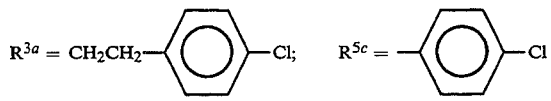

According to General Method L, 14.5 g of 1-(4-chlorophenyl)-3-[2-(4-chlorophenyl)ethyl]-4,5-dihydro-1,4-dimethyl-1H-2,4-benzodiazepine as its fumarate salt was prepared from 17.3 g of the compound of Example 228 and 7.6 g of methyl iodide. The salt was recrystallized from EtOH/ether, mp 173–175.

General Method M

The procedure described under General Method L was followed except that two equivalents of N-butyllithium and two equivalents of aldehyde were used.

General Method N

The benzodiazepine in 3–7 mL of THF per mmol of benzodiazepine was stirred at −78° C. while 1.1 equivalents of butyllithium was added under nitrogen. The solution was stirred for one hour at −78° C. 1.1–1.3 equivalents of hexachloroethane were added, and the reaction was stirred for one-half hour at −78° C. The reaction was poured into 1N HCl, washed three times with ether, made basic with 35% sodium hydroxide, extracted into ether, dried over potassium carbonate, filtered and stripped. The resulting brown oil was filtered through silica with ethyl acetate, stripped and taken directly to the next step. The 3-chloromethyl benzodiazepine was either dissolved in chloroform and treated with 3–5 equivalents of the appropriate amine or it was dissolved directly in a large excess of the amine. The solution was refluxed from 1–20 hours. The solvent was removed and the product was crystallized as shown in Table E.

General Method O

The procedure was substantially similar to General Method L except that inverse addition of the lithium salt of the benzodiazepine was made to 1.5 equivalents of the chloroester.

General Method P

The procedure was substantially similar to General Method L except that lithium diisopropylamide, generated from butyllithium and diisopropylamine, was used as the base and the reaction was run at 0°.

General Method Q

The procedure was substantially similar to General Method L except that the reaction was quenched after stirring one hour at −55° by adding a slight excess of acetic acid in THF.

General Method R

The benzodiazepine-3-one was dissolved in 13–14 equivalents of phosphorus oxychloride and one-quarter equivalent of phosphorus pentoxide was added. The mixture was stirred at room temperature under nitrogen briefly, then heated at 90° C. for 18 hours. The solution was stripped in vacuo, and the residue treated with 4–9 equivalents of the appropriate amine and stirred for two hours at room temperature. The excess amine was stripped in vacuo, and the residue was crystallized as shown in Table F.

TABLE F

| Example No. | R³ | Method | Yield % | Melting Range | Salt | Recrystallized From |
|---|---|---|---|---|---|---|
| 121 | —N(morpholino) | R | 20 | 245–246 | HCl | CH₂Cl₂/hexane |
| 122 | N(Me)₂ | R | 33 | 124–125 | free base | not rex; from column 9:1 EtOAc Et₂N |
| 123 | —N(piperidino) | R | 53 | 159–161 | 2-naphthalenesulfonate (SO₃H) | 2-butanone |

TABLE G

[Structures: starting material VIII (phthalazinone with R², R⁵, R⁶) or IX (benzyl hydrazone with R², R⁵, R⁶) → product (benzene ring with CH₂NHR² and CH(NH₂)R⁵ substituents and R⁶)]

| Example No. | Starting Material | R² | R⁵ | R⁶ | Method | Yield % | Melting Range | Salt | Recrystallization From |
|---|---|---|---|---|---|---|---|---|---|
| 124 | VIII | CH₂CH₂N(morpholine) | Ph | H | S | 100 | oil | — | — |
| 125 | VIII | Ph | Me | H | T | 88 | 71–72 | free base | ether/hexane |
| 126A | IX | Me | (4-OMe-C₆H₄) | H | S | 48 | — | — | — |
| 126B | VIII | Me | CH₃O— | H | S1 | 70 | 245–247 | 2HCl | MeOH/ether |
| 126C | VIII | CH₂CH₂OMe | | H | | 67 | — | 2HCl | THF/ether |
| 127 | VIII | Me | Me | H | S | 100 | oil | — | — |
| 128 | VIII | Me | Ph | 7,8-diOMe | S | — | oil | — | — |
| 129 | VIII | CH₂CH₂OMe | Ph | H | S | 42 | 252–254 | 2HCl | — |
| 130 | VIII | Me | (1-naphthyl) | H | T | 72 | 244–246 | 2HCl·1/2H₂O | EtOH/ether |
| 131 | VIII | iPr | Ph | H | S | 94 | 264–266 | 2HCl | MeOH/ether |
| 132 | VIII | Me | Ph | H | S | 94 | 163–168 | 2HCl | EtOH/ether |

TABLE G-continued

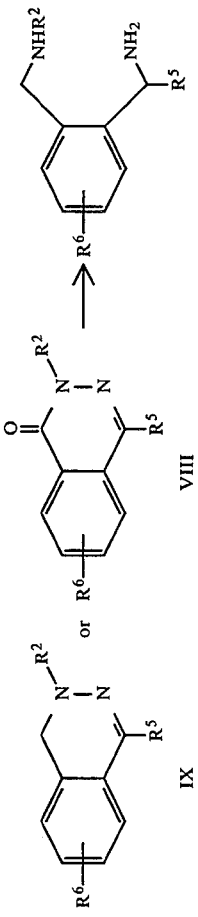

| Example No. | Starting Material | R² | R⁵ | R⁶ | Method | Yield % | Melting Range | Salt | Recrystallization From |
|---|---|---|---|---|---|---|---|---|---|
| 133 | VIII | Me | (2-thienyl) | H | T | 48 | 201–203 | 2HCl | MeOH/EtOH |
| 134 | VIII | Bzl | Ph | H | S | 70 | >260 | 2HCl | MeOH/ether |
|  |  |  |  |  | T | 83 | 275–276 | 2HCl | MeOH/ether |
| 135 | VIII | Me | (5-amino-2-chlorophenyl) | H | T | 57 | — | free base | — |
| 136 | VIII | Me | (4-F-phenyl) | H | S | 100 | — | free base | — |
| 136A | VIII | Me | 4-F-Ph | H | SI | 45 | 198–200 | 2HCl | MeOH/CH₃CN/Et₂O |
| 137 | IX | Me | Ph | 6-F | S | 89 | oil | free base | — |
| 138 | IX | Me | Ph | 7-F | S | 92 | oil | free base | — |
| 139 | IX | Me | Ph | 8-F | S | 61 | oil | free base | — |
| 140 | IX | Me | Ph | (2-methylphenyl) | T | 56 | oil | free base | — |

TABLE G-continued

| Example No. | Starting Material | R² | R⁵ | R⁶ | Method | Yield % | Melting Range | Salt | Recrystallization From |
|---|---|---|---|---|---|---|---|---|---|
| 141 | IX | Me | Ph | 8,9 fused 9-Me | S | 29-61 | oil | free base | — |
| 142 | VIII | CH₂CH₂NEt₂ | Ph | H | S | 89 | oil | free base | — |
| 143 | VIII | Et | Ph | H | S | 91 | 241-243 | 2 HCl·1/4H₂O | MeOH/THF |
| 144 | VIII | Me | 4-Cl-C₆H₄ | H | T | 61 | 259-261 | 2HCl | EtOH/ether |
| 145 | VIII | cyclopropyl-CH₂ | Ph | H | T | 90 | amorphous | 2HCl | ether |
| 146 | VIII | Me | 4-pyridyl | H | S | 72 | | | |
| 146A | VIII | Me | 4-pyridyl | H | S1 | 71 | 140-149 | 3HCl | — |
| 147 | VIII | CH₂CH₂Ph | Ph | H | T | 96 | 156-160 | 2HCl | MeOH/THF/ether |
| 148 | VIII | Me | Bzl | H | T | 87 | 267 | 2HCl | MeOH/ether |
| 207 | VIII | Me | cyclohexyl | H | S | 98 | 275-277 | 2HCl | MeOH/ether |
| 287 | VIII | Me | Ph | NO₂ | S | 24 | 80-81 | free base | MeOtBu/hexane |
| 277 | VIII | 4-NO₂-C₆H₄-CH₂ | Ph | H | S | 82 | amorphous | 2HCl | MeOH/ether |
| 294 | VIII | Me | 4-Cl-Ph | H | S1 | 90 | 261-263 | 2HCl | MeOH/ether |
| 304 | VIII | Me | 4-CH₃S-Ph | H | T2 | 74 | 240-243 | 2HCl | — |
| 311 | VIII | Me | 2,4-(F)₂-Ph | H | T2 | 88 | — | 2HCl | — |

TABLE G-continued

| Example No. | Starting Material | R² | R⁵ | R⁶ | Method | Yield % | Melting Range | Salt | Recrystallization From |
|---|---|---|---|---|---|---|---|---|---|
| 328 | VIII | Me | 4-$CH_3SO_2$-Ph | H | S1 | 89 | 227–234 | 2HCl | MeOH/THF |
| 335 | VIII | —$(CH_2)_2$-4-pyridinyl | 4-Cl-Ph | H | T2 | 70 | 218–220 | 3HCl | MeOH |
| 357 | VIII | Me | 4-Br-Ph | H | S1 | 86 | 255 (dec.) | 2HCl | — |
| 362 | VIII | Me | 4-$CH_3SO_2$—NH-Ph | H | S1 | 62 | — | 2HCl | — |
| 370 | VIII | $CH_2CH_2OCH_3$ | 4-Cl-Ph | H | T3 | 87 | — | 2HCl | EtOH/$CH_3CN$/$Et_2O$ |
| 375 | VIII | Me | 4-iPr-Ph | H | T3 | 88 | 230–235 | 2HCl | —(a) |
| 387 | VIII | Me | 3,4-$(Cl)_2$-Ph | H | S1 | 72 | 190–195 | 2HCl | —(b) |
| 390 | VIII | Me | 3-$MeSO_2NH$-4-Cl-Ph | H | T2 | 28 | amorphous | 2HCl | — |
| 401 | VIII | Me | 2,4-$(Cl)_2$-Ph | H | T2 | 89 | >280 | 2HCl | — |
| 405 | VIII | Me | 3-Cl-4-$CH_3O$-Ph | H | T2 | 65 | 239.5–242 | 2HCl | MeOH/THF(a) |
| 408 | VIII | Me | 4-$CH_3$-Ph | H | S1 | 57 | 267–269 | 2HCl | MeOH/THF |
| 413 | VIII | Me | 2,4-$(Et)_2$-Ph | H | T2 | 91 | 271–174 | 2HCl | — |
| 420 | VIII | Me | Ph | 8-$CH_3SO_2NH$ | T2 | 13 | 114–117.5 | free base(c) | — |

(a)The crude dihydrochloride salt was purified by converting the salt to the free base by treatment with 2N NaOH and then reconverting the free base back to the dihydrochloride salt.
(b)The crude dihydrochloride salt was purified by converting the salt to the free base by treatment with saturated $Na_2CO_3$ and then reconverting the free base back into the dihydrochloride salt.
(c)The crude dihydrochloride salt was converted into the free base by treatment with $Na_2CO_3$ and the free base was purified by column chromatography on silica eluting with $CH_2Cl_2$/MeOH/isopropylamine (90/5/5).

General Method S

The appropriate phthalazine or phthalazinone was treated with 4–8 equivalents of diborane in THF and the mixture was refluxed for 2–5 days under nitrogen. Usually the 4–8 equivalents of diborane were added in two or three portions over the course of the reaction. The reaction was allowed to cool to room temperature and excess aqueous or alcoholic hydrochloric acid was added carefully under nitrogen. The reaction was refluxed, the THF was removed in vacuo and the residue was made basic with 35% aqueous sodium hydroxide. The product was extracted into ethyl acetate, dried over sodium sulfate, concentrated in vacuo, and either purified as the hydrochloride salt as shown in Table G or, more commonly, used without further purification as the free base. In Table G, the Roman numeral IX indicates that the starting material was the corresponding phthalazine; the Roman numeral VIII indicates that the starting material was the corresponding phthalazinone.

General Method S1

The appropriate phthalazinone in THF under $N_2$ was treated with 4–7.5 equivalents of a 1M borane THF solution and the mixture was refluxed for 2–9 days. Usually the 4–7.5 equivalents of borane were added in two portions over the course of the reaction. The reaction mixture was cooled to room temperature, quenched with methanol and refluxed for about 0–4 hours. The mixture was again cooled and saturated methanolic. HCl was added and the mixture was brought back to reflux for about 0–1.5 hours. The mixture was filtered and filtrate was concentrated in vacuo to afford the dihydrochloride salt which was purified by recrystallization as shown in Table G.

General Method T

The procedure was substantially similar to General Method S except that 0.1–0.5 equivalent of sodium borohydride and 0.7 to 1.5 mL of diglyme per mmol of phthalazinone were added.

General Method T2

The procedure was substantially similar to that described in General Method S1 except that 0.1–0.7 equivalents of sodium borohydride and 0.2–7 mL of diglyme per mmol of phthalazinone were added.

General Method T3

The procedure was similar to that described in General Method S1 except that 0.05–0.08 equivalents of sodium borohydride and 0.5–0.6 mL of diglyme per mmol of phthalazinone were added, and the mixture was refluxed for 0–4 hours after the addition of the methanolic.HCl.

EXAMPLE 149

4,5-Dihydro-3-ethyl-4-methyl-1-phenylmethyl-1H-2,4-benzodiazepine (Formula I: $R^1$, $R^4$, $R^6$=H; $R^2$=Me; $R^3$=Et; $R^5$=Bzl)

A solution of 12.5 g (50 mmol) of 2-[(1-amino-2-phenyl)-ethyl]-N-methylbenzenemethanamine in 150 mL of isopropyl acetate was treated with 4.1 g (50 mmol) of sodium acetate and 30 mL (150 mmol) of triethylorthopropionate and 5 mL (87 mmol) of acetic acid. The mixture was refluxed for three hours and poured into 1.5 L of ice water containing 200 mL of 2N sodium hydroxide. The product was extracted into ethyl acetate, dried over sodium sulfate and stripped. The residue was recrystallized from isopropyl alcohol/ether to yield 7.5 g of the free base. The free base in ethanol was treated with 4.6 g of cyclohexane sulfamic acid and the solvent removed in vacuo. The residue was recrystallized from isopropyl alcohol/ether to provide 5.8 g of product as the cyclohexane sulfamic acid salt, mp 137–138.

EXAMPLE 150

4,5-Dihydro 3-ethyl-1-phenyl-1H-2,4-benzodiazepine (Formula I: $R^1$, $R^2$, $R^4$, $R^6$=H; $R^3$=Et; $R^5$=Ph)

A mixture of 1.36 g (3.6 mmol) of 4-benzyl-4,5-dihydro-3-ethyl-1-phenyl-1H-2,4-benzodiazepine, 136 mg of 10% palladium on carbon, and 257 mg (4.0 mmol) of ammonium formate in 50 mL of methanol was refluxed under nitrogen for three hours. Four more 230-mg portions of ammonium acetate were added every two hours during reflux until TLC on silica gel with 5% diethylamine in ethyl acetate showed a complete conversion. The reaction was cooled, filtered and stripped. The residue was distributed between aqueous sodium hydroxide and ether. The ether extract was dried over sodium sulfate, treated with decolorizing carbon, filtered and stripped. The residue was taken up in 60:40 ethyl acetate/ether and acidified with dilute ethereal HCl. The resulting precipitate was filtered off and recrystallized from isopropanol/ether to yield 0.61 g (61%) of the hydrochloride salt of the product, mp 203–204.

EXAMPLE 151

4,5-Dihydro-4-methyl-1-phenyl-1H-2,4-benzodiazepin-3-amine monohydrochloride (Formula I: $R^1$, $R^4$, $R^6$=H; $R^2$=Me; $R^3$=NH_2; $R^5$=Ph)

A solution of 15 g (66 mmol) of 2-[(methylamino)methyl]-α-phenylbenzenemethanamine in 85 mL of methanol was treated with 7.2 g (68 mmol) of cyanogen bromide at room temperature. The solution was stirred at room temperature for 18 hours and stripped. The residue was dissolved in ethanol and the ethanol stripped off. The residue was recrystallized from methanol/isopropyl acetate to yield 4.55 g of the free base, mp 156–159. The mother liquors were dissolved in ethanol, treated with a slight excess of ethanolic HCl and recrystallized from ethanol to yield 1.3 g of the hydrochloride salt, mp 259–261.

EXAMPLE 152

1,2,4,5-Tetrahydro-4-methyl-1-phenyl-3H-2,4-benzodiazepin-3-thione

To a suspension of 15 g (50 mmol) of 2-[(methylamino)methyl]-α-phenylbenzenemethanamine dihydrochloride in 100 mL of isopropyl alcohol was added 10 g (100 mmol) of potassium acetate followed by 3.3 mL (55 mmol) of carbon disulfide in 35 mL of isopropyl alcohol. The suspension was stirred at room temperature for one and one-half hours and then refluxed for 30 minutes. The reaction was chilled in ice and the internal salt of the carbamodithioic acid, contaminated with two equivalents of potassium chloride, was filtered off. The carbamodithioic acid was suspended in 125 mL of 95% ethanol, and 1.3 mL of 12N hydrochloric acid was added. The suspension was refluxed for three days, cooled, and 15.3 g (114%) of the crude benzodiazepin-3-thione was filtered off. A 6-g portion of the crude product was recrystallized from 2-ethoxy ethanol to yield 2.0 g (38%) of product, mp 208–209.

EXAMPLE 153

3-[[2-(Diethylamino)ethyl]amino]-4,5-dihydro-4-methyl-1-phenyl-1H-2,4-benzodiazepine

[Formula I: $R^1$, $R^4$, $R^6$=H; $R^2$=Me; $R^3$=NH(CH$_2$)$_2$N(C$_2$H$_5$)$_2$]

A slurry of 11.7 g (44 mmol) of 4-methyl 1-phenyl-1,2,4,5-tetrahydro-3H-2,4-benzodiazepin-3-thione of Example 152 in 146 mL ethanol was treated with 4.2 mL (67 mmol) of iodomethane in 30 mL ethanol added dropwise at 50°. The reaction was stirred at ambient temperature for 18 hours and 13.48 g (75%) of 4-methyl-1-phenyl-3-methylthio-4,5-dihydro-1H-2,4-benzodiazepine was collected, mp 201–205, as the hydriodide salt.

A solution of 22.7 g (55 mmol) of the 3-methylthiobenzodiazepine in 285 mL of methanol was refluxed with 7.8 mL (55 mmol) of N,N-diethylethylenediamine for 18 hours. The reaction was filtered hot to remove a small amount of insoluble impurity, cooled, stripped, and distributed between methylene chloride and aqueous sodium hydroxide. The organic extracts were dried over magnesium sulfate and stripped. The residue was recrystallized with great difficulty as the fumarate salt from isopropanol. After multiple recrystallizations 1.5 g of the product was obtained as the difumarate hemihydrate, mp 160–162.

EXAMPLE 154

4,5-Dihydro-4-methyl-1-phenyl-1H-2,4-benzodiazepin-3-sulfonic acid (Formula I: $R^1$, $R^4$, $R^6$=H; $R^2$=Me; $R^3$=SO$_3$H; $R^5$=Ph)

Twenty-nine grams (108 mmol) of 1,2,4,5-tetrahydro-4-methyl-1-phenyl-3H-2,4-benzodiazepin-3-thione of Example 152 was treated with 2.4 g of sodium chloride, 420 mg of sodium molybdate dihydrate and 35 mL of 30% hydrogen peroxide in 50 mL of water and 10 mL of t-butanol according to the procedure of Maryanoff et al., J.O.C. 51, 1882 (1986). The reaction remained a suspension at all times, and after heating at 70°–80° for two hours, the product was filtered off from the chilled suspension to yield 30.6 g (90%) of the sulfonic acid requiring no further purification, mp 188–190.

EXAMPLE 155

4,5-Dihydro-4-methyl-1-phenyl-3(1-pyrrolidino)-1H-2,4-benzodiazepine (Formula I: $R^1$ $R^4$ $R^6$=H; $R^2$=Me; $R^3$=C$_4$H$_8$N; $R^5$=Ph)

A mixture of 4.75 g (15 mmol) of the sulfonic acid of Example 154 and 20 mL of pyrrolidine was refluxed for 18 hours. The pyrrolidine was stripped off and the residue was chromatographed on 340 g of silica gel, eluting with 95:5 ethyl acetate/diethylamine to yield 3.12 g of residue which was recrystallized from 40 mL of hexane to yield 2.14 g (47%) of product, mp 118–119.

EXAMPLE 156

3-[(4,5-Dihydro-4-methyl-1-phenyl-1H-2,4-benzodiazepin-3-yl)thio]-N,N-diethylpropaneamine (Formula I: $R^1$, $R^4$, $R^6$=H; $R^2$=Me; $R^3$=S(CH$_2$)$_3$N(C$_2$H$_5$)$_2$; $R^5$=Ph)

A solution of 12 g (45 mmol) of 1,2,4,5-tetrahydro-4-methyl-1-phenyl-3H-2,4-benzodiazepin-3-thione of Example 152 in 100 mL of DMF was treated with 1.24 g (50 mmol) of sodium hydride at 70° and 7.5 g (50 mmol) of 3-diethylaminopropyl chloride was added dropwise at 70°. The reaction was stirred at 70° for five hours and then at room temperature for two days. The reaction was poured into 250 mL of ice water and extracted twice into ethyl acetate. The product was extracted into 150 mL of 2N HCl, washed with ethyl acetate, made basic, and extracted back into ethyl acetate. The ethyl acetate solution was dried over magnesium sulfate, stripped, and the residue was dissolved in acetone. Two equivalents of maleic acid in 40 mL of acetone was added, followed by a small amount of ether. The resulting precipitate was recrystallized from acetone/ether to provide 13.2 g of product as the dimaleate salt, mp 95–97.

EXAMPLE 157

4,5-Dihydro-4-methyl-3-methylthio-1-phenyl-1H-2,4-benzodiazepine (Formula I: $R^1$, $R^4$, $R^6$=H; $R^2$=Me; $R^3$=SMe; $R^5$=Ph)

A solution of 8 g (30 mmol) of the thione of Example 152 and 2.7 mL (44 mmol) of methyl iodide in 100 mL of ethanol was refluxed two hours, cooled, and the hydriodide of the product filtered off. The salt was partitioned between methylene chloride and aqueous sodium bicarbonate, the organic layer dried over magnesium sulfate, and stripped. The residue was dissolved in ethanol and 2.7 g of methanesulfonic acid was added followed by ether. The resulting precipitate was filtered off and recrystallized from ethanol to yield 5.2 g of product as the methanesulfonate salt, mp 195–196.

EXAMPLE 158

1,2,4,5-Tetrahydro-4-methyl-1-phenyl-3H-2,4-benzodiazepin-3-one

A solution of 32.8 g (145 mmol) of 2-[(methylamino)methyl]-α-phenylbenzenemethanamine in 215 mL of chloroform was treated with 25.9 g (159 mmol) of carbonyldiimidazole. The reaction was stirred at room temperature for 19 hours, washed four times with water, dried over sodium sulfate and stripped in vacuo. The gummy residue was triturated in and recrystallized from ethyl acetate to yield 26 g (71%) of product, mp 198–199.

EXAMPLE 159

5-Butyl-4,5-dihydro-3-ethyl-4-methyl-1-phenyl-1H-2,4-benzodiazepine (Formula I: $R^1$=nBu; $R^2$=Me; $R^3$=Et; $R^4$ and $R^6$=H, $R^5$=Ph)

A suspension of 14.16 g (60 mmol) of 2-methyl-4-phenyl-1 (2H)-phthalazinone in 340 mL of THF was cooled to −65° under nitrogen and treated with 24.8 mL (62 mmol) of 2.5N n-butyllithium in hexane. The mixture was stirred for 20 minutes at −65°, and 240 mL (240 mmol) of 1N borane-THF complex was added. The solution was allowed come to room temperature and 340 mg (9 mmol) of sodium borohydride were added. The reaction was refluxed for 20 hours, another 340 mg of sodium borohydride was added, the reaction refluxed another 24 hours. The reaction was cooled and quenched with 100 mL of methanol. Eighty milliliters of 3.5N HCl in methanol was added, the reaction was refluxed two hours and 19.9 g (93%) of the dihydrochloride of 2-[1-(methylamino) pentyl]-α-phenyl-benzenemethanamine was isolated by filtration. The benzene-methanamine was treated with triethylorthopropionate and sodium acetate in isopropyl acetate according to General Method E to yield 9.48 g of the free base of the product, mp 102-114 after recrystallization from methyl t-butyl ether/hexane. Seven grams of the free base was converted to the hydrochloride salt and recrystallized from acetone ether to yield 5.08 g of product as the monohydrochloride salt, mp 209-211.

EXAMPLE 160

4,5-Dihydro-1,5-diphenyl-3-ethyl-4-methyl-1H-2,4-benzodiazepine (Formula I: $R^1$, $R^5$=Ph; $R^2$=Me; $R^3$=Et; $R^4$, $R^6$=H)

The procedure of Example 159 was used, substituting phenyllithium for butyllithium. The intermediate 2-[(methylamino)phenylmethyl]-α-phenylbenzenemethanamine was crystallized as the dihydrochloride salt containing 0.6 moles water of hydration, mp 202-216. It was cyclized with triethyl-orthopropionate as in Example 158 to yield 32% of the product as the hydrochloride salt, mp 275-276, from acetone/ether.

EXAMPLE 266

4,5-Dihydro-1-(4-hydroxyphenyl)-4-methyl-3-(2-phenylethyl)-1H-2,4-benzodiazepine (Formula I: $R^1$, $R^4$, $R^6$=H; $R^2$=Me; $R^3$=CH_2CH_2PH; $R^5$=

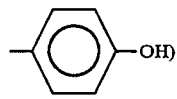

A solution of 6.78 g (17 mmol) of the methoxy compound of example 60 in 70 mL of methylene chloride was treated with 32 mL of 1M boron tribromide in methylene chloride (32 mmol) at 0° under nitrogen for 2 hours. The reaction was poured into 2N aqueous HCl, stirred 1 hour, filtered free of boron salts and extracted into methylene chloride with a trace of methanol after making basic with Na_2CO_3. The organic layer was dried, stripped and the residue taken up in methanol. Methanolic HCl was added and the salt crystallized by the addition of ether. The hydrochloride was recrystallized from methanol, mp 245-247, yield 90%.

EXAMPLE 267

4,5-Dihydro-3-[2-(4-hydroxyphenyl)ethyl]-4-methyl-1-phenyl-1H-2,4-benzodiazepine (Formula I: $R^1$, $R^4$, $R^6$=H; $R^2$=Me, $R^3$=

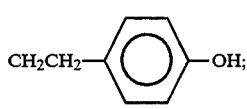

$R^5$=Ph)

By a process analogous to that of Example 266, 1.14 g of 4,5-dihydro-3-[2-(4-hydroxyphenyl)ethyl]-4-methyl-1-phenyl-1H-2,4-benzodiazepine was obtained as the hydrochloride salt from 2.47 g (6.1 mmol) of the methoxy compound of Example 35, mp 160-162 from methanol/ether.

EXAMPLE 268

4,5-Dihydro-1-(4-hydroxyphenyl)-3-[2-(4-hydroxyphenyl)-ethyl]-4-methyl-1H-2,4-benzodiazepine (Formula I: $R^1$, $R^4$, $R^6$=H; $R^2$=Me; $R^3$=

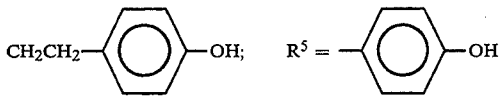

By a process analogous to that of Example 266, 1.80 g of 4,5-dihydro-1-(4-hydroxyphenyl)-3-[2-(4-hydroxyphenyl)ethyl]-4-methyl-1H-2,4-benzodiazepine was obtained from 4.5 g (8.7 mmol) of the dimethoxy compound of example 229 using 3.5 equivalents of boron tribromide. The free base was insoluble in methylene chloride. The hydrochloride hemihydrate was obtained by recrystallization from MeCN/MeOH, mp 266-228.

EXAMPLE 161

1,2,3,5-Tetrahydro-10-phenylpyrrolo[1,2-b][2,4]benzodiazepine (Formula II: $R^1$=Ph; q=1; $R^{4a}$, $R^{5b}$, $R^6$, $R^{15}$, $R^{16}$=H)

A. A mixture of 18.95 g (66.5 mmol) of 2-(aminomethyl)-α-phenylbenzenemethanamine dihydrochloride, 24.74 g (133 mmol) of ethyl 4-chlorobutanimidate hydrochloride, and 10.91 g (133 mmol) of sodium acetate was reacted in methanol according to General Method D. The residue after extraction and stripping was chromatographed on 400 g of silica gel, eluting with a gradient from 5-6% isopropylamine in methyl t-butyl ether. The two products resulting from cyclization toward and away from the phenyl substituent were isolated. The first to emerge was the isomer resulting from cyclization away from the phenyl group, i.e. the compound of Example 162 (see below). The second to emerge was the compound resulting from cyclization towards the phenyl group. It eluted primarily between 500 and 625 mL and yielded 5.8 g of residue on stripping. The residue was converted to the fumarate salt with 3.48 of fumaric acid in 60 mL of ethanol and recrystallized twice from ethanol/ether to yield 5.65 g of pure product as the fumarate salt, mp 205-207.

B. The free base of the product was dissolved in a minimum of hot acetonitrile and one equivalent of D-α-bromocamphorsulfonic acid was added. The diastereomeric salt with the (−) enantiomer of the diazepine crystallized out. The free base of the single enantiomer was regenerated and the fumarate salt again formed; mp 145°-147°; $[\alpha]_d^{25}$ (c=1, MeOH) −230°.

C. The free base of the mother liquors from part B was treated as before with one equivalent of L-α-bromocamphorsulfonic acid to obtain the fumarate salt of the (+)enantiomer, mp 145-147; $[\alpha]_d^{25}$ (C=1; MeOH) +249°.

EXAMPLE 280

10-Methyl-10-phenyl-1,2,3,
5-tetrahydro-10H-pyrrolo[1,2-b][2,4]benzodiazepine (Formula II: $R^1$=Ph; q=1; $R^{4a}$, $R^{5b}$, $R^6$, $R^{16}$=H; $R^{15}$=Me)

Following General Method L, 2.1 g (8 mmol) of 10-phenyl-1,2,3,5-tetrahydropyrrolo[1,2-b][2,4]benzodiazepine of Example 161 was reacted with 1.37 g (9.6 mmol) of methyl iodide to produce 10-methyl-10-phenyl-1,2,3,5-tetrahydro- 10H-pyrrolo[1,2-b][2,4]benzodiazepine, obtained by chromatography on silica gel with 3% isopropylamine in MeOtBu and recrystallization of the fumarate salt from ethanol-ether, mp 198–200, yield 1.37 g (62%).

EXAMPLE 162

1,2,3,5-Tetrahydro-5-phenylpyrrolo[1,2-b][2,4]benzodiazepine (Formula II: $R^1$, $R^{4a}$, $R^6$, $R^{15}$, $R^{16}$=H; q=1; $R^{5b}$=Ph)

In the synthesis described in Example 161, the earlier fractions, which eluted between 125 and 250 mL in the isopropylamine/t-butylmethyl ether chromatography, were combined and stripped to yield 7.9 grams of residue which was converted to the fumarate salt with 4.6 grams of fumaric acid in 120 mL of ethanol. The fumarate was recrystallized from ethanol/ether to yield 8.9 g of the fumarate salt, mp 217–218. The fumarate salt was reconverted to the free base with 2N aqueous sodium hydroxide and the free base recrystallized from methylene chloride/hexane to yield 5.58 g of pure product as the free base, mp 152–153.

EXAMPLE 163

1,2,3,
5-Tetrahydro-5-methyl-5-phenylpyrrolo[1,2-b][2,4]benzodiazepine (Formula II: $R^1$, $R^6$, $R^{15}$, $R^{16}$=H; q=1; $R^{4a}$=Me; $R^{5b}$=Ph)

A solution of 2.10 g (8 mmol) of the benzodiazepine of Example 162 in 32 mL of THF was treated with 3.5 mL of 2.5N n-butyllithium in hexane and 1.31 g of methyl iodide according to General Method L. The residue was recrystallized from acetone to yield 0.9 g of product, mp 166–168, as the free base. A further 1.07 g were obtained by chromatography of the mother liquors using the same system as Example 161. The combined residues were treated with one equivalent of maleic acid in acetone and recrystallized from acetone/ether to provide 2.24 g of product as the maleate salt, mp 209–210.

EXAMPLE 164

1,2,3,4-Tetrahydro-11-phenyl-6H-pyrido[1,2-b][2,4]benzodiazepine (Formula II: $R^1$=Ph, q=2; $R^{4a}$=$R^{5b}$=$R^6$=$R^{15}$=$R^{16}$=H)

By a procedure analogous to that of Example 161, using ethyl 5-chloropentanimidate hydrochloride in place of ethyl 4-chlorobutanimidate hydrochloride, 17.1 g (60 mmol) of 2-(aminomethyl)-a-phenylbenzenemethanamine was converted to a mixture of two isomers resulting from cyclization towards and away from the phenyl group. The mixture was separated as before using isopropylamine in methyl t-butyl ether. Once again the slower fraction was the isomer resulting from cyclization towards the phenyl group. The residue from chromatography, which weighed 6.6 g, was converted to the hydrochloride salt and recrystallized from methanol/ether to give 2.95 g of the hydrochloride salt of the product, mp 310–311.

EXAMPLE 165

1,2,3,
4-Tetrahydro-6-phenyl-6H-pyrido[1,2-b][2,4]benzodiazepine (Formula II: $R^1$, $R^{4a}$, $R^6$, $R^{15}$, $R^{16}$=H; q=2; $R^{5b}$=Ph)

The chromatography as in Example 161 of the reaction mixture from Example 164 yielded 10.35 g of impure benzodiazepine. It was converted to the HCl salt, recrystallized from methanol/ether, and the free base was liberated with aqueous sodium hydroxide and recrystallized from methylene chloride/hexane to provide 4.6 g of free base, mp 113–114. The free base was reconverted to the HCl salt and recrystallized from methanol/ether to provide 3.0 g of product as the monohydrochloride, mp 296–297.

EXAMPLE 166

1,2,3,4-Tetrahydro-6-methyl-6-phenylpyrido[1,2-b][2,4]benzodiazepine (Formula II: $R^1$, $R^6$, $R^{15}$, $R^{16}$=H; q=2; $R^{4a}$=Me; $R^{5b}$=Ph)

By a process analogous to Example 163, 2.9 g of benzodiazepine of Example 165 was converted to 2.75 grams of the maleate salt of the product. The maleate salt was recrystallized twice from methanol/ether to yield 2.42 grams of product, mp 190–192.

EXAMPLE 281

10a-Phenyl-4-(2-phenylethyl)-5-phenylethyl-1,2,3,10a-tetrahydro-6H-pyrrolo[2,1-a][2,4]benzodiazepinium chloride (Formula XXXIV: $R^{2c}$=Bzl; $R^{3a}$=CH$_2$CH$_2$PH; $R^{5c}$=Ph)

A solution of 16.4 g (39 mmol) of 4,5-dihydro-1-phenyl-3-(2-phenylethyl)-4-phenylmethyl-1H-2,4-benzodiazepine of Example 221 in 100 mL of THF was stirred at −78° under nitrogen and 17.3 mL (43 mmol) of 2.5 N butyllithium in hexane was added. The mixture was stirred 1 hour and 4.9 mL (49 mmol) of 1-bromo-3-chloropropane was added The reaction was stirred 1 hour at −78°, 1 hour at −45° and 18 hours at room temperature, then poured into saturated brine and extracted into about 300 mL of 6:1:1 ether-ethyl acetate-dichloromethane. The organic layer was dried over sodium sulfate and stripped. The residue was recrystallized from methanol-acetone-ether to yield 2.99 g of product as the monohydrate, mp 190–192.

EXAMPLE 282

4-Methyl-10a-phenyl-5-phenylmethyl-1,2,3,10a-tetrahydro-6H-pyrrolo[2,1-a][2,4]benzodiazepinium bromide (Formula XXXIV: $R^{2c}$=Bzl; $R^{3a}$=Me; $R^{5c}$=Ph)

Following the procedure of Example 281, 5.7 g of 4-methyl-10a-phenyl-5-phenylmethyl-1,2,3, 10a-tetrahydro-6H-pyrrolo[2,1-a][2,4]benzodiazepinium bromide was obtained from 12 g (37 mmol) of 4,5-dihydro-3-methyl-1-phenyl-4-phenylmethyl-1H-2,4-benzodiazepine of Example 210. It was recrystallized from methanol-ether, mp 249°–250°.

EXAMPLE 283

10a-Phenyl-4-(2-phenylethyl)-1,2,3,10a-tetrahydro-6H-pyrrolo[2,1-a][2,4]benzodiazepine (Formula XXXV: $R^{3a}$=CH$_2$CH$_2$PH, $R^{5c}$=Ph)

A solution of 5.0 g (10 mmol) of the 5-benzyldiazepinium chloride of Example 281 in 130 mL of methanol was reduced with 3.3 g (50 mmol) of ammonium formate and 1.25 g of 10% Pd on carbon at reflux for 1 hour. The product was recrystallized from ether-hexane as the free base, mp 134–136, yield 3.23 g (87%). Some of the free base was converted to the hydrochloride salt and recrystallized from THF-EtOAc-ether with a few drops of methanol, mp 195–197.

EXAMPLE 284

4-Methyl-10a-phenyl-1,2,3,10a-tetrahydro-6H-pyrrolo[2,1-a][2,4]benzodiazepine (Formula XXXV: $R^{3a}$=Me; $R^{5c}$=Ph)

Following the procedure of Example 283, 3 g (7.5 mmol) of the 5-benzyl benzazepinium compound of Example 282 was reduced to provide 1.80 g of 4-methyl-10a-phenyl-1,2,3,10a-tetrahydro-6H-pyrrolo[2,1-a][2,4]benzodiazepine hydrochloride, mp 231–235, from methanol-THF-ether.

EXAMPLE 285

10-Methyl-10-phenyl-3-phenylmethyl-1,2,3,5-tetrahydro-10H-pyrrolo[1,2-b][2,4]benzodiazepine (Formula II: $R^1$=Ph, $R^{4a}$=$R^{5b}$=$R^6$=H; $R^{15}$=Me; $R^{16}$=Bzl; q=1)

Following General Method L, 5 g (18 mmol) of 10-methyl-1-phenyl-1,2,3,5-tetrahydro-10H-pyrrolo[1,2-b][2,4]benzodiazepine of Example 280 was reacted with 3.72 g of benzyl bromide to provide 1.96 g of the fumarate salt of 10-methyl-10-phenyl-3-phenylmethyl-1,2,3,5-tetrahydro-10H-pyrrolo-[1,2-b][2,4]benzodiazepine, mp 125–150, (mixture of diastereomers) from ethanol-ether. In this case the reaction was worked up by pouring into water made slightly basic with NaOH and extracting into methylene chloride, then flash chromatographing on silica gel with MeOtBu-methylene chloride then MeOtBu.

EXAMPLE 286

3,10-Dimethyl-1-phenyl-1,2,3,5-tetrahydro-10H-pyrrolo[1,2-b][2,4]benzodiazepine (Formula II: $R_1$=Ph, $R^{4a}$=$R^{5b}$=$R^6$=H; $R^{15}$=$R^{16}$=Me; q=1)

By a procedure analogous to that of Example 285, the benzodiazepine of Example 280 was reacted with methyl iodide to provide 1.58 g of the fumarate salt of 3,10-dimethyl-1-phenyl-1,2,3,5-tetrahydro-10H-pyrrolo[1,2-b][2,4]benzodiazepine, mp 210–211, from ethanol-ether. The chromatography was with 0.5% isopropylamine in MeOtBu.

Resolution of Enantiomers

EXAMPLE 167

(R)-(+)-4,5-Dihydro-4-methyl-1-phenyl-3-(2-phenylethyl)-1H-2,4-benzodiazepine

To a 1 L Erlenmeyer flask was added 100 mL of methanol, 200 mL of water and 49.8 g (0.133 mol) of the racemic hydrochloride salt of Example 25. The solution was stirred for ten minutes, then 200 mL of t-butylmethyl ether (TBME) added to the homogeneous solution followed by 220 mL (0.66 mol, 5.0 eq) of 3N sodium hydroxide. The mixture was stirred for 10 minutes. The layers were separated and the aqueous layer extracted with 100 mL of saturated sodium chloride. The organic layer was dried over magnesium sulfate, filtered and the solvent removed under reduced pressure at 30° C. to give a quantitative yield of free base. The viscous golden-brown oil was placed on a vacuum pump at 0.5 mmHg for 1 hour.

The free base was dissolved into 40 mL of methanol with slight warming. The solution was transferred to a 500 mL 3 neck flask equipped with mechanical stirrer and condenser. The transfer was completed by rinsing with an additional 20 mL of methanol. The methanol solution was warmed to 45° C. with an external temperature-controlled water bath.

To a 250 mL beaker was added 40.4 g (0.113 mol, 0.85 eq) of D-O,O'-dibenzoyltartaric acid and 40 mL of methanol. (Slight warming may be necessary to get chiral acid into solution.) The methanol solution of the chiral acid was added slowly with constant stirring to the solution of free base. The resulting mixture became a very light green color. An additional 20 mL of methanol was used for rinsing to complete the transfer. After stirring 5 minutes, the solution was seeded. The product began to precipitate immediately. The solution was stirred overnight at 45° C. The granular, white precipitate was collected on a Buchner funnel, washed 3×25 mL with cold methanol (5° C.) and dried overnight at 60° C. under reduced pressure.

The dried dibenzoyltartrate salt weighed 40.9 g (88%) after correcting for the quantity of seed crystal; $[\alpha]_D^{25}$ = +192. (c=1, methanol); mp 143°–145° C. dec.

The hydrochloride salt may be made by the following procedure:

The free base from 100 g (0.143 mol) of dibenzoyltartrate salt was prepared as above. The free base was dissolved into 300 mL of ethyl acetate. The solution was transferred to a 2-liter 3-neck flask equipped with mechanical stirrer, condenser and additional funnel. The transfer was completed by rinsing with an additional 300 mL of ethyl acetate. The ethyl acetate solution was warmed to 45° C. with a temperature-controlled water bath.

To the warmed ethyl acetate solution of the free base was slowly added 69 mL of a 2.3N hydrogen chloride/ethyl acetate solution. The addition of the acid was completed over a 0.5 h period, followed by stirring at 45° C. for 1 hour. The ethyl acetate suspension of the resulting hydrochloride salt was refluxed for 1 hour to eliminate the excess hydrogen chloride present in the solvent and cooled to ambient temperature. The flocculent white precipitate was collected on a Buchner funnel and washed 3×150 mL with ethyl acetate. The product was dried overnight at 80° C. under reduced pressure.

The dried hydrochloride salt weighed 50.9 g, $[\alpha]_D^{25}$ = +234° (c=1, methanol); mp 197°–199° C.

EXAMPLE 168

(S)-(−)-4,5-Dihydro-4-methyl-1-phenyl-3-(2-phenylethyl)-1H-2,4-benzodiazepine

The mother liquors from crystallization in Example 167 were stripped and the free base liberated as before using tBuOMe and aqueous NaOH. The free base was dissolved in 100 mL of methanol, treated with 34.3 g of dibenzoyl-L-tartaric acid and seeded. There was obtained 37.2 g of the diastereomeric salt of the (−)-isomer, mp 160–170, $[\alpha]_D^{25}$−198° (C=1, MeOH). The free base was generated as above, and the HCl salt was formed and recrystallized from acetonitrile/ether, mp 198–199, $[\alpha]_D^{25}$=−249° (C=1, CHCl$_3$).

EXAMPLE 169

(+)-4,5-Dihydro-1-phenyl-1,3,4-trimethyl-1H-2,4-benzodiazepine

By a process analogous to that of Example 167 involving multiple recrystallizations, 1.4 g of (+)-4,5-dihydro-1-phenyl-1,3,4-trimethyl-1H-2,4-benzodiazepine was obtained from 8.9 g (33.7 mmol) of the racemic product of Example 96 and 12.7 g (33.7 mmol) of dibenzoyl-L-tartaric acid hydrate. The free base was obtained, without recrystallization, by stripping the tBuOMe, mp 115–116, $[\alpha]_D^{25}$=+101° (C=1, MeOH).

EXAMPLE 170

(−)-4,5-Dihydro-1-phenyl-1,3,4-trimethyl-1H-2,4-benzodiazepine

By a process analogous to that of Example 168, 1.9 g of (−)-4,5-dihydro-1-phenyl-1,3,4-trimethyl-1H-2,4-benzodiazepine was obtained from the mother liquors of Example 169, mp 116–117, $[\alpha]_D^{25}$=−93° (C=1, MeOH).

EXAMPLE 171

(R)-(+)-4,5-Dihydro-3-ethyl-4-methyl-1-phenyl-1H-2,4-benzodiazepine

By a process analogous to that of Example 167, 7.5 g of R-(+)-4,5-dihydro-3-ethyl-4-methyl-1-phenyl-1H-2,4-benzodiazepine was obtained from 92 g of the free base of the racemic product of Example 8, after repeated crystallization. The hydrochloride salt was obtained from ethanol/ether, mp 244–247, $[\alpha]_D^{25}$=+347° (C=1, CHCl$_3$).

The d-10-camphorsulfonic acid salt was obtained from acetonitrile, mp 215–218, $[\alpha]_D^{25}$=+203° (C=1, MeOH), $[\alpha]_D^{25}$=+242° (C=1, CHCl$_3$).

EXAMPLE 172

(S-)(−)-4,5-Dihydro-3-ethyl-4-methyl-1-phenyl-1H-2,4-benzodiazepine

By a process analogous to that of Example 168, 15 g of the levo enantiomer was obtained from the mother liquors of Example 171. The product was crystallized as the hydrochloride from ethanol/ether, mp 247–249, $[\alpha]_D^{25}$=−343° (C=1, CHCl$_3$).

EXAMPLE 173

(S)-(−)4,5-Dihydro-3-ethyl-4-methyl-1-phenyl-1H-2,4-benzodiazepine

The following procedure describes an alternate synthesis of the compound of Example 172:

Two grams (6.3 mmol) of the monohydrochloride of (S)-N-[[[2-(methylamino)methyl]phenyl]phenylmethyl]propanamide (Example 181) was stirred in 15 mL of toluene under nitrogen and 3.45 mL of 2M trimethyl aluminum in toluene was added at 0°. The mixture was stirred two hours at room temperature, then 1.5 hours at reflux. The reaction was cooled and quenched with 0.31 mL of water followed by 0.93 mL of 30% aqueous NaOH. Methylene chloride, a small amount of methanol and some sodium sulfate were added, the mixture was filtered, stripped and the residue recrystallized from MeOH/ether as the hydrochloride, mp 247–248.

EXAMPLE 296

(+)-4,5-Dihydro-4-methyl-3-(4-chlorophenyl)-3-methyl-1H-2,4-benzodiazepine

A solution of the racemic free base of Example 295 (14.007 g) in ethanol was heated on a steam bath and a solution of dibenzoyl-L-tartaric acid (17.80 g) in hot ethanol (500 mL) was added. The mixture was cooled to room temperature and the crystals that formed were collected by filtration (mother liquor used in Example 297) and dried at 80° C. in vacuo. The salt was recrystallized from methanol and dried at 60° C. in vacuo to afford 13.53 g of the dibenzoyl-L-tartaric acid salt, m.p. 160.5°–161.5° C., $[\alpha]_D^{25}$=94.7° (C=0.61, MeOH). The salt was then converted into the free base of the (+)-isomer by dissolving the salt in a mixture of 1N NaOH, ether, CH$_2$Cl$_2$ and methanol, separating the organic layer, washing the organic layer with brine, drying the organic layer over Na$_2$SO$_4$ and removing the solvent in vacuo. The free base was purified by Kugelrohr distillation, followed by recrystallization from ethyl acetate/hexane to afford 5.35 g of the free base of the (+)-isomer, m.p. 138°–139° C., $[\alpha]_D^{25}$=+341° (C=1.0, EtOH).

EXAMPLE 297

(−)-4,5-Dihydro-4-methyl-1-(4-chlorophenyl)-3-methyl-1H-2,4-benzodiazepine

The mother liquor from the initial crystallization of the dibenzoyl-L-tartaric acid salt of Example 296 was concentrated in vacuo and the residue was taken up in ethanol/tert-butylmethyl ether and treated with 1N NaOH. The organic layer was separated, washed with brine, dried over Na$_2$SO$_4$ and concentrated in vacuo to regenerate the free base. The free base was dissolved in ethanol (300 mL), heated on a steam bath, and treated with dibenzoyl-D-tartaric acid monohydrate (12.75 g) in hot ethanol (200 mL). The crystals which formed were collected by filtration and dried at 60° C. in vacuo to afford 15.03 g of the dibenzoyl-D-tartaric acid salt, m.p. 162°–163° C., $[\alpha]_D^{25}$=−87.3° (C=0.565, MeOH). The dibenzoyl-D-tartaric acid salt was then converted to the free base of the (−)-isomer as described hereinabove in Example 296 to afford 6.085 g of the free base of the (−)-isomer, m.p. 137°–138.5° C., $[\alpha]_D^{25}$=−335° (C=1.00, EtOH).

EXAMPLE 307

(+)-4,5-Dihydro-3,4-dimethyl-1-(4-methylthiophenyl)-1H-2,4-benzodiazepine

The racemic free base of Example 306 (7.45 g, 25 mmol) was dissolved in ethanol (50 mL) and treated with a solution of dibenzoyl-L-tartaric acid (9.28 g, 25.9 mmol) in hot ethanol (100 mL). The precipitate which formed was collected by filtration, washed with ethanol and then tert-butylmethyl ether (combined filtrates used in Example 308) and the salt was recrystallized from methanol to afford 4.60 g of the dibenzoyl-L-tartaric acid salt, m.p. 164.5°–165.5° C., $[\alpha]_D^{25}$=+101° (C=0.385, MeOH). The dibenzoyl-L-tartaric acid salt (3.92 g, 6 mmol) was then mixed with 2N NaOH (7 mL, 14 mmol), water (10 mL) and CH$_2$Cl$_2$ (20 mL) to afford a two-phase mixture. The organic phase was separated, the aqueous phase was extracted with CH$_2$Cl$_2$ and the combined organic extracts were washed with water containing a small amount of a saturated $Na_2CO_3$ solution. The organic layer was dried over $Na_2SO_4$ and the solvent was removed in vacuo to afford an oil which was crystallized from tert-butylmethyl ether to afford 1.57 g of (+)-4,5-dihydro- 3,4-dimethyl-1-(4-methylthiophenyl)-1H-2,4-benzodiazepine, m.p. 133°–134° C., $[\alpha]_D^{25} = +352.3°$ (C=0.01095, EtOH).

EXAMPLE 308

(−)-4,5-Dihydro-3,4-dimethyl-1-(4-methylthiophenyl)-1H-2,4-benzodiazepine

The mother liquors from the initial crystallization of the dibenzoyl-L-tartaric acid salt were concentrated in vacuo, dissolved in $CH_2Cl_2$, and basified with 1N NaOH (50 mL). The aqueous phase was extracted with $CH_2Cl_2$ and the combined organic layers were washed with water containing 2N NaOH (1 mL) and dried over $Na_2SO_4$. The solvent was removed in vacuo to afford 4.1 g of the free base. The free base (3.4 g, 11.5 mmol) was dissolved in ethanol (25 mL), and added to a solution of dibenzoyl-D-tartaric acid in hot ethanol (25 mL). The precipitate which formed was collected by filtration, washed with ethanol and then tert-butylmethyl ether and dried in vacuo at 80° C. The salt was then recrystallized from methanol to afford 3.13 g of the dibenzoyl-D-tartaric acid salt, m.p. 169.5°–170° C., $[\alpha]_D^{25} = -100.5°$ (C=0.0439, MeOH) . The dibenzoyl-D-tartaric acid salt was then converted into the free base as described hereinabove in Example 307 to afford (−)-4,5-dihydro-3,4-dimethyl-1-(4-methylthiophenyl)-1H-2,4-benzodiazepine, m.p. 134°–135.5° C., $[\alpha]_D^{25} = -341.1°$ (C=0.00455, EtOH).

EXAMPLE 314

(+)-4,5-Dihydro-3,4-dimethyl-1-(2,4-difluorophenyl)-1H-2,4-benzodiazepine

Following a procedure substantially similar to that described in Example 307 except that methanol was used as the solvent rather than ethanol, there was obtained 26.5 g of the dibenzoyl-L-tartaric acid salt, $[\alpha]_D^{25} = +32.8°$ (C=0.119, MeOH), after recrystallization of the salt from methanol, from the racemic free base of Example 313 (25.70 g, 0.0898 mol) and dibenzoyl-L-tartaric acid (33.46 g, 0.0924 mol). The benzoyl-L-tartaric acid salt (18.0 g) was converted into the free base as described in Example 307 to afford 7.94 g of (+)-4,5-dihydro-3,4-dimethyl-1-(2,4-difluorophenyl)-1H-2,4-benzodiazepine, m.p. 137°–138° C., $[\alpha]_D^{25} = +236°$ (C=1.025, EtOH).

EXAMPLE 315

(−)-4,5-Dihydro-3,4-dimethyl-1-(2,4-difluorophenyl)-1H-2,4-benzodiazepine

The mother liquors from Example 314 were concentrated in vacuo and the residue was treated with $CH_2Cl_2$ (400 mL), $H_2O$ (300 mL) and 2N NaOH (45 mL). The organic layer was separated, washed with water and dried over $Na_2SO_4$. Removal of the solvent in vacuo and purification of the residue by recrystallization from ethyl acetate, dissolving the solid in ether and washing with 0.5N HCl, and recrystallization from tert-butylmethyl ether (3×) affords the free base (10.5 g) of racemic 4,5-dihydro-3,4-dimethyl-1-(2,4-difluorophenyl)-1H-2,4-benzodiazepine. The racemic free base (10.5 g, 39.1 mmol) was mixed with dibenzoyl-D-tartaric acid (14.4 g, 40.3 mmol) and hot methanol (2.5 L). The precipitate which formed was collected by filtration and was recrystallized from methanol (6×) to afford 5.45 g of the dibenzoyl-D-tartaric acid salt, $[\alpha]_D^{25} = -25°$ (C=0.138, MeOH). An additional 2.90 g of the dibenzoyl-D-tartaric acid salt was also obtained from the methanol filtrate by repeated recrystallization from methanol to afford a total of 8.35 g of the salt. The salt (8.0 g) was suspended in $CH_2Cl_2$ (200 mL)/water (200 mL), cooled to 0° C. and treated with 2N NaOH (12.4 mL, 24.8 mmol). After stirring for 15 minutes the aqueous phase was separated, extracted with $CH_2Cl_2$ and the combined organic layers were dried over $Na_2SO_4$. Removal of the solvent in vacuo and azeotroping the residue with toluene (2×200 mL) afforded 3.8 g of (−)-4,5-dihydro-3,4-dimethyl-1-(2,4-difluorophenyl)-1H-2,4-benzodizepine.

EXAMPLE 174

2-[[(1,1-Dimethylethyl)amino]methyl]-α-phenylbenzenemethanamine (Formula XXXVII: $R^{1a}$=H, $R^{2a}$=tBu, $R^{5a}$=Ph, A =Phenyl)

A solution of 15.9 g (90 mmol) of N-t-butylbenzamide in 390 mL of THF was cooled to −15° under nitrogen and 77 mL (193 mmol) of 2.5N n-butyllithium in hexane was added. The mixture was stirred at −5°±3° for one hour and 17.5 g (99 mmol) of the trimethylsilylimine of benzaldehyde [prepared according to the procedure of Hart et al., *J. Org. Chem.* 48, 289–294 (1983)] was added over ten minutes at −10°. The reaction was stirred at 0° for one hour, then 5° for 45 minutes. It was poured into 400 mL of ice water containing 225 mL of 2N HCl and washed twice with ether. The aqueous layer was made basic with sodium hydroxide and extracted into ether. The ether extracts were dried over sodium sulfate and stripped to yield 25.4 g of 2-[(amino)(phenyl)methyl]-N-(1,1-dimethyl-ethyl)benzamide.

The entire portion of aminoamide in 50 mL of THF was combined with 450 mL (450 mmol) of 1N borane-THF complex and the mixture stirred at reflux for 18 hours. The reaction was cooled, 225 mL of methanol was added, and the solution was refluxed for one hour. It was recooled and 200 mL of half-saturated methanolic HCl was added. The solution was again refluxed for one hour, evaporated in vacuo and the residue recrystallized from chloroform/ether to yield 21.3 g (70%) of product as the dihydrochloride, mp 222–231.

EXAMPLE 175

2-(Aminomethyl)-N-methyl-α-phenylbenzenemethanamine (Formula XXXVII: $R^{1a}$=Ph; $R^{2a}$=Me; $R^{5a}$=H; A =phenyl)

Seventy-five grams (0.36 mole) of 2-benzoylbenzaldehyde was dissolved in 70 mL of THF and 18.5 g (0.39 moles) of methylhydrazine was added over 30 minutes at 0°. The suspension became a homogeneous solution which was allowed to stand for four days. A first portion comprising 8.5 g of product was obtained by addition of hexane and filtration. A second portion of 27.5 g of product was obtained by chromatography on silica gel with 85:15 methylene chloride/ethyl acetate. The mp of the hydrazone after recrystallization from methylene chloride-hexane was 164–165.

A solution of 44.5 g of the methylhydrazone in 80 mL of THF was treated with 374 mL of 1M borane-THF and stirred at reflux. After 24 hours and 72 hours, additional 187 mL portions of 1M borane were added. After six days the reaction was worked up as described in Example 164 and the dihydrochloride recrystallized from methanol ether, mp 224–226.

EXAMPLE 176

2-(Aminomethyl)-α-phenyl-N-(phenylmethyl)benzenemethanamine (Formula XXXVII: $R^{1a}$=Ph; $R^{2a}$=Bzl; $R^{5a}$=H; A=phenyl)

Sixty-two grams (0.30 mole) of 2-benzoylbenzaldehyde in 140 mL of THF was treated with 81.5 g (0.59 mole) of potassium carbonate and 64 g (0.32 mole) of benzylhydrazine dihydrochloride. The mixture was stirred 30 minutes at 0° and 40 mL of methylene dichloride was added. The mixture was stirred at room temperature for one day, filtered and stripped in vacuo to provide 131 g of 2-benzyl-1-phenyl phthalazinium chloride.

The crude phthalazinium chloride in 175 mL of THF was treated with 1.325 L of 1M borane-THF at reflux under nitrogen. After 24 hours the reaction was worked up as described in Example 175 and the dihydrochloride salt was formed by precipitation from ether with ethereal HCl to provide 36.8 g of dihydrochloride of the product, mp 175–178.

EXAMPLE 270

N-Methyl-α'-phenyl-2,3-thiophenedimethanamine (Formula XXXVII: $R^{1a}$=H; $R^{2a}$=Me; $R^{5a}$=Ph; A=thiophene)

Following the procedure of General Method T, 19 g of N-methyl-α'-phenyl-2,3-thiophenedimethanamine was prepared from 32.6 g (0.135 mol) of 6,7-dihydro-6-methyl-7-oxo-4-phenylthieno[2,3-d]pyridazine. The product was recrystallized as its dihydrochloride from ethanol-water, mp 290–292.

EXAMPLE 279

2-(Amino)phenylmethyl-N-methylbenzeneethanamine (Formula XXXII: $R^{2b}$=Me, $R^{5d}$=Ph, $R^{6a}$=H)

By General Method T, 25.8 g (0.103 mol) of 4,5-dihydro-3-methyl-1-phenyl-2,3-benzodiazepin-4-one was reduced to yield 18.6 g of 2-(amino)phenylmethyl-N-methylbenzeneethanamine as its dihydrochloride salt, mp 257–258 from methanol-ether.

TABLE H

Structure: benzene ring with two ortho substituents: -CH2-NH-R9 and -CH(R5a)-NHCOR11

| Example No. | R9 | R11* | R5a | Source | Yield % | Melting Range | Salt/Solvate | Recrystallization From |
|---|---|---|---|---|---|---|---|---|
| 177 | Me | CH2CH2Ph | Ph | General Method U benzodiazepine from Ex. 25 | 96 | 110-123 | HCl (amorphous) | CH2Cl2/ether |
| 178 | Me | CH2CH2Ph | 4-Cl-C6H4 | alumina chromatography of Ex. 63 hexane/CH2CH2 80:20 | 15 | 274-275 | HCl | EtOH/ether |
| 179 | Me | CH2-(4-(N-Me)piperazinyl) | Ph | silica gel chromatography of Ex. 76 MeOtBu/hexane/iPrNH2 85:10:5 | 2 | 134-136 | 1.5 fumarate | MeOH/ether |
| 180 | Me | CH2O-(4-Cl-C6H4) | Ph | silica gel chromatography of Ex. 39 toluene/hexane/iPrNH2 50:49:1 | 26 | 178-179 | HCl | EtOH/ether |
| 181 | Me | Et | Ph | General Method U benzodiazepine of Ex. 8 | 89 | 206-208 | HCl | MeOH/ether |
| 182 | Me | Ph | Ph | silica gel chromatography of Ex. 1 0.75% iPrNH2 in tBuOMe from recrystallization EtOAc/hexane of Ex. 23 | 8 | 132-133 | free base | CH2Cl2/tBuOMe/hexane |
| 183 | iPr | Me | Ph | silica gel chromatography of Ex. 50 CHCl3/Et3N 96:4 | 4 | 116-117 | free base | EtOAc/hexane |
| 184 | CH2CH2NEt2 | Et | Ph | | 2 | viscous liquid | free base | — |
| 208 | Ph | CH2CH2Ph | Me | silica gel chromatography of Ex. 235 MeOBu/hexane 1:1 | 34 | 137-138 | free base | MeOtBu/hexane |
| 209 | Me | CH2CH2-(4-NHSO2CH3-C6H4) | Ph | crystallized from free base of Ex. in toluene | 34 | 224-228 | HCl | EtOH/ether |

TABLE H-continued

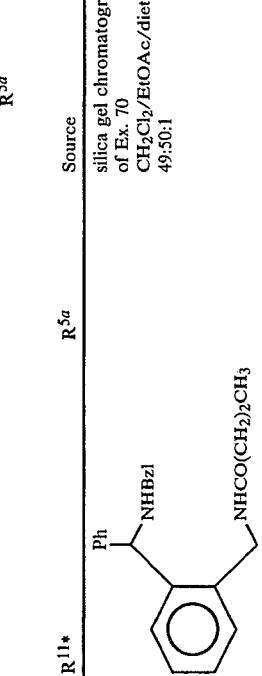

| Example No. | R⁹ | R¹¹* | R⁵ᵃ | Source | Yield % | Melting Range | Salt/Solvate | Recrystallization From |
|---|---|---|---|---|---|---|---|---|
| 273 | | | | silica gel chromatography of Ex. 70 CH₂Cl₂/EtOAc/diethylamine 49:50:1 | | 116–119 | HCl | |
| 289 | Me | Et | Ph | General Method U1 benzodiazepine from Ex. 172 | 89 | 206–208 | HCl (−)-isomer$^{(a)}$ | |
| 291 | Me | Et | Ph | General Method U1 benzodiazepine from Ex. 171 | 81 | 207.5–208.5 | HCl (+)-isomer$^{(b)}$ | — |

*R¹¹ is (CH₂)nR¹⁰
$^{(a)}[\alpha]_D^{25} = -42.4°$ (C = 0.1, MeOH)
$^{(b)}[\alpha]_D^{25} = +46.6°$ (C = 0.1, MeOH)

EXAMPLES 177-184, 208, 209, 273

Aminoamides of formula III

III 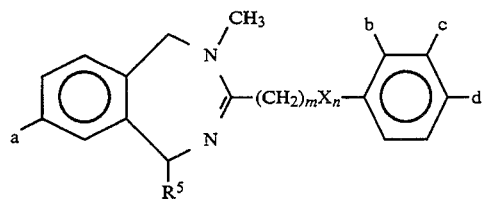

TABLE L

Reduction of NO₂ to NH₂ in compound of formula:

| Example No. | R⁵ | X | n | Position of NO₂→NH₂ | m | Method | Yield % | Melting Range | Salt | Recrystallized From |
|---|---|---|---|---|---|---|---|---|---|---|
| 250 | Ph | CH=CH | 1 | c | 0 | V | 58 | 234-237 | 2 HCl | MeOH/ether |
| 251 | Ph | — | 0 | d | 0 | V | 81 | 314-315 | 2 HCl | MeOH/ether |
| 252 | Ph | — | 0 | a | 2 | V | 77 | 209-211 | 2 HCl | MeOH/ether |
| 253 | Ph | — | 0 | b | 2 | W | 92 | 215-228 | 2 HCl | MeOH/ether |
| 254 | -⟨O⟩-Cl | — | 0 | d | 2 | W | 80 | 290-291 | 2 HCl | MeOH/ether |
| 255 | Ph | — | 0 | d | 2 | W | 88 | 173-175 | HCl.1/4 EtOH | EtOH/ether |
| 256 | Ph | CH=CH | 1 | d | 0 | V |  | 212-215* | 2 HCl | MeCN/ether |
| 347 | Ph | — | 0 | d | 2 | W1 | 57 | 123-124.5 | free base (+)-isomer⁽ᵃ⁾ | EtOAc/Et₂O/hexane⁽ᵇ⁾ |
| 350 | Ph | — | 0 | d | 2 | W1 | 64.5 | 124-125.5 | free base (−)-isomer⁽ᶜ⁾ | EtOAc/tBuOMe/hexane |

*4.1 trans/cis
⁽ᵃ⁾$[\alpha]_D^{22} = +267°$ (C = 1.0, MeOH).
⁽ᵇ⁾free base was purified by column chromatography on silica eluting with 1% isopropylamine in tert-butylmethylether/CH₂Cl₂ (1/3) prior to recrystallization.
⁽ᶜ⁾$[\alpha]_D^{22} = -261°$ (C = 1.0, MeOH).
⁽ᵈ⁾free base was purified by column chromatography on silica eluting with ½% isopropylamine in CH₂Cl₂/t-BuOMe (3/1) prior to recrystallization.

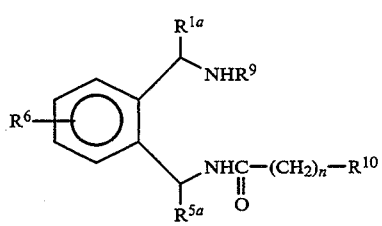

were obtained as by-products of the synthesis of the corresponding benzodiazepines and were usually isolated via chromatography on silica gel using basic elution solvents. They were also obtained by hydrolysis of the corresponding benzodiazepines as described in General Method U. Examples are given in Table H

General Method U

A solution of the appropriate benzodiazepine in 3 to 5 mL of methanol per millimole of diazepine was stirred at room temperature for 1 to 4 days with 3 to 5 equivalents of potassium hydroxide in 1 to 2 mL of water per millimole of diazepine. Aqueous sodium chloride was added and the aminoamide was extracted into ether. The ether layer was dried over MgSO₄, filtered, stripped and the residue was treated as shown in Table H. It is anticipated that any species described in Tables A through E could be converted to the corresponding aminoamide by this procedure.

General Method U1

The procedure described under General Method U was followed except that 5.6-5.7 equivalents of potassium hydroxide was used and the aminoamide was extracted with a CH₂Cl₂/ether mixture.

General Method V

The appropriate nitro compound, as its salt, usually the fumarate salt, was dissolved in about 10 mL of dry methanol per millimole of nitro compound and 0.1 to 0.15 g of 10% Pd on carbon was added per millimole of nitro compound. The reaction was stirred at 18°-24° and 7.5 to 8.0 equivalents of ammonium formate was added. After 1-2 hours the reaction was filtered, stripped, distributed between methylene chloride and 2N NaOH, separated, dried and stripped. The residue was crystallized as shown in Table L.

General Method W

The appropriate nitro compound, as its hydrochloride salt or the free base plus one equivalent of methanolic HCl, was dissolved in about 20 mL of methanol or ethanol per millimole of nitro compound and about 0.05 to 0.1 g of 10% Pd on carbon was added per millimole of nitro compound. The mixture was hydrogenated at 3.5 to 1.4 atm on a Parr shaker. When the calculated amount of hydrogen had been consumed, the reaction was filtered, excess ethereal HCl was added, and the solution was stripped. The residue was crystallized as shown in Table L.

General Method W1

The procedure was similar to that described in General method W, except that about 4 mL of methanol rather than 20 mL of methanol or ethanol per mmol of nitro compound was used and the reaction mixture was worked up as follows. The catalyst was removed by filtration, the filtrate was concentrated in vacuo and the residue was dissolved in CH₂Cl₂ and basified with 1N-2N NaOH. The CH₂Cl₂ layer was separated dried over Na₂SO₄, and concentrated in vacuo and the residue thus obtained was purified as the free base as illustrated in Table L.

EXAMPLE 274

4-[2-(4,5-Dihydro-3-ethyl-1H-2,4-benzodiazepin-4-yl)ethyl]benzeneamine (Formula I: R$^1$, R$^4$, R$^6$=H; R$^2$=

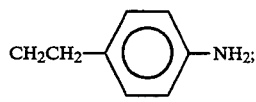

R$^3$=Et; R$^5$=Ph

By General Method W, 4.50 g (10.3 mmol) of 4,5-dihydro-3-ethyl-4-[2-(4-nitrophenyl)ethyl]-1H-2,4-benzodiazepine hydrochloride of Example 276 was reduced to 3.33 g of 4[2-(4,5-dihydro-3-ethyl-1H-2,4-benzodiazepin-4-yl)ethyl]benzeneamine as its monohydrochloride, mp 149-151 from EtOH-ether.

gel eluting with MeOH/MeOtBu/isopropylamine 49:49:2. The product was recrystallized as shown in Table M.

EXAMPLE 275

N-[4-[2-(4,5-Dihydro-3-ethyl-1H-2,4-benzodiazepin-4-yl)ethyl]phenyl]methanesulfonamide (Formula I: R$^1$, R$^4$, R$^6$=H; R$^2$=

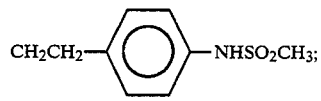

R$^3$=Et; R$^5$=Ph)

By General Method X, 3.25 g of 4-[2-(4,5-dihydro-3-ethyl-1H-2,4-benzodiazepin-4-yl)ethyl]benzeneamine of Example 274 was converted to 3.49 g of N-[4-[2-(4,5-dihydro-3-ethyl-1H-2,4-benzodiazepin-4-yl)ethyl]phenyl]methanesulfonamide, mp 129-142 as the free base from EtOH-ether-methylene chloride.

STARTING MATERIALS

The phthalazinones, which are the starting materials for the synthesis of diamines described in Table G, are generally available by methods known in the literature. They are most commonly synthesized by condensation of the corresponding γ-ketoacids with the appropriate hydrazine. For example,

EXAMPLE 185

2-Methyl-4-phenyl-1 (2 H)-phthalazinone

A 100 gallon stainless steel unit was charged with 40.0 kg of 2-benzoylbenzoic acid and 87.5 kg of toluene. Methylhydrazine was added over about 45 minutes with the internal temperature rising to 34°.

The resulting thin slurry was warmed at reflux (95°-18°) for 4 ½ hours while collecting about 7.5 L of water.

The reaction mixture was cooled slowly with initial precipitation evident at 88°. The resulting slurry was

TABLE M

Acylation and Sulfonylation of Amines of Formula:

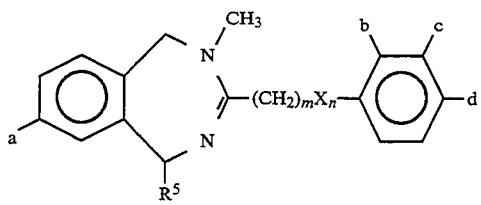

| Example No. | R$^5$ | m | x | n | Position of NH₂ | Product | Method | Yield % | Melting Range | Salt | Recrystallized From |
|---|---|---|---|---|---|---|---|---|---|---|---|
| 257 | Ph | 0 | CH=CH | 1 | d | NHSO₂CH₃ | X | 82 | 274-276 | HCl | EtOH/ether |
| 258 | Ph | 0 | CH=CH | 1 | c | NHSO₂CH₃ | X | 60 | 297-298 | HCl | MeOH/ether |
| 259 | Ph | 0 | CH=CH | 1 | d | NHCOCH₃ | X | 62 | 174-190 | HCl.2H₂O | EtOH/H₂O |
| 260 | Ph | 0 | — | 0 | d | NHSO₂CH₃ | X | 53 | 283-284 | HCl | MeOH/ether |
| 261 | Ph | 0 | — | 0 | d | NHCOCH₃ | X | 76 | >300 | HCl | MeOH/ether |
| 262 | Ph | 2 | — | 0 | d | NHSO₂CH₃ | X | 87 | 153-159 | HCl.EtOH | EtOH/ether |
| 263 | Ph | 2 | — | 0 | a | NHSO₂CH₃ | X | 75 | 170-182 | HCl | MeCN/ether |
| 264 | 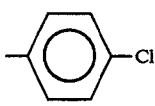 | 2 | — | 0 | d | NHSO₂CH₃ | X | 93 | 168-172 | HCl | MeOH/ether |

General Method X

A solution of the appropriate amine as its dihydrochloride and from 3 equivalents of pyridine to 30 equivalents of pyridine were stirred at 0° in about 10 mL of methylene chloride per millimole of amine under a nitrogen atmosphere while 1.1 to 1.5 equivalents of methanesulfonyl chloride or acetyl chloride was added dropwise. The reaction was stirred at 0° for 1-2 hours and one volume of saturated aqueous Na₂CO₃ was added. In a few cases where TLC showed incomplete reaction, an additional 1 to 3 equivalents of chloride was added before the Na₂CO₃ solution. The layers were separated and the organic layer was stripped. The residue was flash chromatographed, if necessary, on silica cooled to 0 to −5° before collecting the beige colored crystals. The cake was washed with 2×20 L of cold toluene and dried in vacuo at 45°-50° overnight to afford 38.0 kg (91.0% yield) 2-methyl-4-phenyl-1 (2H)-phthalazinone, mp 166–168.

EXAMPLE 271

6,7-Dihydro-6-methyl-7-oxo-4-phenylthieno[2,3-d]pyridazine

A solution of 31.2 g (0.134 mol) of 3-benzoyl-2-thiophenecarboxylic acid in 400 mL of ethanol was treated with 9.3 (0.2 mol) of methylhydrazine at room temperature for 18 hours, refluxed 3 hours, cooled and 30.7 g of the product filtered off, mp 174–175.

The 3-benzoyl-2-thiophene carboxylic acid was obtained from 3-bromothiophene by the method of MacDowell and Ballas [*J. Org. Chem.* 42, 3717 (1977).]

In the cases where the appropriate alkylhydrazine for the condensation to the phthalazinone is not readily available, the γ-ketoacid is condensed with hydrazine and the resulting 2-unsubstituted 1-phthalazinone is alkylated. For example,

EXAMPLE 186

4-Phenyl-2-(2-phenylethyl)-1 (2H)-phthalazinone
Eighty-five grams (0.38 moles) of 4-phenyl-1(2H)-phthalazinone was added to 18.4 g (0.47 moles) of sodium hydride in 1 L of DMSO in four portions. The mixture was stirred for two hours at room temperature until evolution of hydrogen had ceased, and 95.5 g (0.52 moles) of 2-bromoethylbenzene was added. The mixture was stirred 1.5 hours at room temperature, 1 L of 2N NaOH was added and the slurry was poured into 1 L of water. The product was filtered off and dried to yield 118 g (95%) of 4-phenyl-2-(2-phenylethyl)-1(2H)-phthalazinone, mp 135–138.

EXAMPLE 278

2-[2-(4-Nitrophenyl)ethyl]-4-phenyl-1(2H)-phthalazinone (Formula VIII: $R^2=$

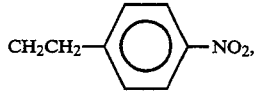

$R^5=Ph, R^6=H$)

By a procedure analogous to that of Example 186, 11.8 g of 2-[2-(4-nitrophenyl)ethyl]-4-phenyl-1(2H)-phthalazinone was prepared from 10.0 g (45 mmol) of 4-phenyl-1(2H)-phthalazinone and 11.6 g (50 mmol) of 4-nitrophenethyl bromide. The product was recrystallized from EtOAc-ether-hexane, mp 152°–155°.

Synthesis of Esters of the formula
$R^8CH=CH—COOEt$ and $R^8CH_2CH_2COOEt$ wherein $R^8$ is heteroaryl In those cases where the appropriate propanoate and propenoate esters were not commercially available, the propenoate was synthesized by condensation of ethyl acetate with the appropriate aldehyde in the presence of one equivalent of sodium metal. The unsaturated esters were reduced with a large excess of magnesium metal in methanol to provide the propanoates.

Miscellaneous syntheses of diamines, phthalazines, and precursors are shown below:

EXAMPLE 187

4-Benzyl-2-methyl-1(2H)-phthalazinone

A solution of 30 g of potassium hydroxide and 31.3 g (140 mmol) of benzylidenephthalide in 100 mL of water was heated to homogeneity and poured into a solution of 40 mL of $H_2SO_4$ in 250 mL of water. After cooling, the resulting solid was collected and dissolved in aqueous sodium bicarbonate. 2N HCl was added until the first signs of precipitation, the aqueous solution was washed four times with chloroform and then acidified with excess 2N HCl. A white precipitate of 20.3 g of 2-(1-oxo-2-phenylethyl)benzoic acid was filtered off and dried, mp 74–75, after recrystallization from ethanol water. This γ-ketoacid was treated with methylhydrazine according to the method of Example 185 to yield 17.3 g of the phthalazinone product, mp 144–146.

EXAMPLE 188

2-Methyl-4-(2-thienyl-1(2H)-phthalazinone

A solution of 74.1 g (0.5 mole) of phthalic anhydride in 300 mL of nitrobenzene was treated with 147 g (1.1 mole) of aluminum chloride. The solution was stirred for two hours and 42.1 g (0.5 mole) of thiophene was added dropwise over 80 minutes at 40°-45°. The reaction was stirred at 50°-55° for two hours and then let sit at room temperature overnight. The reaction was poured into 2.8 L of cold water, stirred, separated, and the nitrobenzene was removed from the nitrobenzene layer by steam distillation. The residue was recrystallized from toluene to provide 31.1 g (27%) of 2-thienoylbenzoic acid, mp 141–143. The thienoylbenzoic acid was treated with methylhydrazine as described in Example 185 to provide 24.4 g (75%) of the phthalazinone product, mp 143–144, after recrystallization from ethyl acetate.

EXAMPLE 189

5-Fluoro-3,4-dihydro-3-methyl-1-phenylphthalazine

To a solution of 20 g (0.14 mole) of 2-fluoro-6-chlorotoluene in 125 mL of THF was added 6.9 g (0.28 mole) of magnesium turnings. The mixture was refluxed while 12 mL of 1,2-dibromoethane in 50 mL of benzene was added dropwise over three hours. The reaction was refluxed a further hour and 15 mL of benzonitrile was added. The reaction was refluxed a further two hours, cooled and quenched with 50 mL of water added dropwise. The mixture was extracted into ethyl acetate, dried over sodium sulfate and stripped. The residue was dissolved in 50 mL of ethanol, 25 mL of 1N HCl was added, and the mixture was refluxed for three hours. The ethanol was stripped, the product was extracted into ethyl acetate, the ethyl acetate dried over sodium sulfate and stripped. The residue of 3-fluoro-2-methylbenzophenone was chromatographed on silica gel with 20% ether in hexane.

A solution of 1.69 g (7.89 mmol) of the benzophenone in 40 mL of carbon tetrachloride was treated with 100 mg of benzoyl peroxide and 1.5 g (8.43 mmol) of N-bromosuccinimide. The reaction was stirred at room temperature for two hours and then refluxed an additional four hours during which a second portion of 50 mg of benzoyl peroxide and 400 mg of N-bromosuccinimide were added. The reaction was cooled, a small amount of impurity filtered off, and the filtrate concentrated in vacuo to provide 2.5 g of 2-bromomethyl-3-fluorobenzophenone, presumably containing trapped carbon tetrachloride.

The residue of α-bromomethylketone was dissolved in 40 mL of chloroform and a mixture of 1.5 mL of triethylamine and one equivalent of methylhydrazine was added dropwise. The reaction was stirred one hour, washed with 20 mL of aqueous sodium bicarbonate and filtered directly through silica gel eluting with 25% ethyl acetate in hexane. Concentration in vacuo gave 1.86 g (98%) of product which was reduced immediately as shown in Table G.

EXAMPLE 190

2-Benzoyl-5-fluorobenzoic acid

Following the procedure of Example 189, 4.0 g (21.2 mmol) of 2-bromo-5-fluoro toluene was treated with 2.4 mL (23.5 mmol) of benzonitrile. The imine resulting from the condensation was not hydrolyzed. Instead 28.6 g (0.13 mole) of 4-fluoro-2-methyl-benzophenoneimine in 200 mL of water and 100 mL of pyridine was refluxed for eight hours and treated with four portions of potassium permanganate at roughly two-hour intervals. The portions were 53 g, 28 g, 20 g, and 10 g. The reaction was cooled, filtered through diatomaceous earth and concentrated in vacuo. The residue was distributed between aqueous acetic acid and ethyl acetate, the ethyl acetate was dried over magnesium sulfate, and the ethyl acetate was removed in vacuo to provide 16.2 g (51%) of a yellow gum which was used as is.

EXAMPLE 191

2-Benzoyl-4-fluorobenzoic acid

The procedure of Example 190 was used to provide 14.2 g (53%) of product from 21.3 g of 2-bromo-4-fluorotoluene.

EXAMPLE 192

3,4-dihydro-3-methyl-1-phenylbenzo[f]phthalazine

A solution of 10 g (45 mmol) of 1-bromo-2-methylnaphthalene in 75 mL of THF was refluxed with 1.2 g (50 mmol) of magnesium turnings for three hours. The reaction was cooled on ice and 4.8 mL (43 mmol) of benzaldehyde was added. The ice was removed, the reaction was stirred 45 minutes and quenched with 5 mL of 1N HCl followed by 50 mL of water. The reaction was extracted into ethyl acetate, dried over sodium sulfate and flash chromatographed through silica gel with 5–10% ethyl acetate in hexane to provide 8.4 g (75%) of 2-methyl-a-phenyl-1-naphthalenemethanol as a pale yellow gum.

A solution of 10.0 g (40 mmol) of the secondary alcohol in dichloromethane was treated with 12.4 g (58 mmol) of pyridine chlorochromate, refluxed briefly, and stirred at room temperature for one hour. The reaction was diluted with 150 mL of ether and filtered through florisil. Concentration of the filtrate in vacuo afforded 7.92 g (80%) of 1-benzoyl-2-methylnaphthalene as a bright orange gum which slowly crystallized on standing.

By the procedure described in Example 189, 4.4 g (18 mmol) of the benzoylnaphthalene was converted to 1.73 g of the phthalazine product, which was reduced immediately as shown in Table G.

EXAMPLE 193

3,4-Dihydro-3,8-dimethyl-1-phenylphthalazine

By a procedure exactly analagous to that of Example 192, the phthalazine was synthesized from 2-bromo-m-xylene.

EXAMPLE 194

2-Aminomethyl-α-phenylbenzenemethanamine

To a slurry of 3.8 g (100 mmol) of lithium aluminium hydride in 120 mL of THF was added 11.1 g (50 mmol) of 4-phenyl-1(2H)phthalazinone. The mixture was refluxed one hour, cooled, diluted with 100 mL of ether and sequentially treated with 3.8 mL of water, 3.8 mL of 15% aqueous sodium hydroxide and 11.4 mL of water. The mixture was stirred for 30 minutes and the granular precipitate filtered off. The filtrate was diluted with a little toluene, dried over sodium sulfate and stripped to provide 14.1 g of an oil which was dissolved in 180 mL of ethanol and hydrogenated at 50 psi in the presence of 20 mL of ethanolic HCl and 1.5 g of 10% palladium on carbon. After 24 hours a precipitate had formed. The reaction was filtered, the precipitate was slurried in 250 mL of hot methanol and filtered again. The combined filtrates were stripped to about 100 mL and diluted with ether. On cooling, 7.3 g of 1,2,3,4-tetrahydro-1-phenylphthalazine as the monohydrochloride salt was filtered off. It was recrystallized from methanol/ether to provide 6.93 g (56%) of product, mp 251–253.

The tetrahydrophthalazine was redissolved in 200 mL of methanol by warming and hydrogenated at 50 psi at 66° for 20 hours in the presence of 3.5 g of Raney nickel catalyst. The catalyst was filtered off and the filtrate stripped. The residue was recrystallized from methanol/ether to provide 99% yield of the diamine dihydrochloride salt, mp 270–273.

EXAMPLE 195

2-(4-Methoxybenzoyl)benzoic acid

A mixture of 57 g (0.4 mole) of phthalic anhydride and 43 mL (0.4 mole) of anisole in 400 mL of benzene was treated with 105 g (0.8 mole) of aluminum chloride at 5°. The reaction was kept for five days at 5° poured into 600 mL of 2N aqueous HCl and ice and filtered. The residue was triturated in aqueous sodium carbonate and filtered repeatedly until the solid no longer contained product. The sodium carbonate extracts were combined, washed with ether, and acidified with 2N aqueous HCl. The product was extracted into ether, dried over sodium sulfate and stripped. It was recrystallized from toluene to provide 80% yield of product, mp 145–147.

EXAMPLE 196

2-(2-Methoxyethyl)-4-phenyl-1(2H)-phthalazinone

Eighty-five grams (0.38 mole) of 2-benzoylbenzoic acid and 28.6 g (0.38 mole) of hydroxyethylhydrazine were reacted according to the procedure of Example 185. The resulting hydroxyethyl-phthalazinone was suspended in 300 mL of DMF and 200 mL THF and 12.3 g of 60% sodium hydride in oil was added in portions over 40 minutes under nitrogen. The reaction was stirred an additional 45 minutes at room temperature and the evolution of hydrogen ceased. Thirty-one milliliters of methyl iodide was added over 1.5 hours and the reaction was stirred at gentle reflux for 16 hours. It was poured into water and extracted into ether. The ether layers were dried over sodium sulfate and stripped. The residue was chromatographed on silica with 5% ethylamine in ethyl acetate to provide 39 g (47%) of product, mp 115–118 after recrystallization from cyclohexane.

EXAMPLE 197

2-Benzoyl-4,5-dimethoxybenzoic acid

Five hundred milliliters of 37% formalin solution was saturated with hydrogen chloride gas at 15°–20° C. and 70 g (0.38 mole) of veratric acid was added in one portion. The mixture was heated at 60°–70° for seven hours and allowed to sit at room temperature for 14 hours. The solution was concentrated in vacuo, dissolved in about 300 mL of water, cooled and made basic with ammonium hydroxide. The resulting solid was collected by filtration and dried to provide a 65% yield of dimethoxyphthalide.

One hundred eight grams (0.56 mole) of the phthalide was oxidized with 258 grams (1.64 moles) of potassium permanganate according to the procedure of Example 190.

Eighty-one grams of the dimethoxyphthalic acid was converted to 72 g of the corresponding dimethoxyphthalic anhydride by heating briefly in 200 mL of acetic anhydride.

Thirty grams (0.14 mole) of 4,5-dimethoxyphthalic anhydride was suspended in 300 mL of THF and 87 mL (0.17 mole) of phenylmagnesium chloride in THF was added over two hours. The reaction was stirred at room temperature for 14 hours, refluxed for two hours, cooled and poured into saturated ammonium chloride. The mixture was made acidic with 6N HCl, extracted into chloroform, dried over magnesium sulfate, concentrated to provide 30 g of 2-benzoyl-4,5-dimethoxybenzoic acid.

EXAMPLE 272

Methyl 4-(Diethylaminosulfonyl)benzenepropanoate

To 14.5 g of N,N-diethyl-4-bromobenzenesulfonamide (50 mmol) (prepared by reaction of 4-bromobenzenesulfonyl chloride with diethylamine) was added 13.8 g of tetrabutylammonium chloride (50 mmol), 10.3 g of NaHCO$_3$ (124 mmol), 266 mg of palladium (II) acetate (1.07 mmol) and 100 mL of DMF in the order given. To this suspension was added 8.8 ml of methyl acrylate (98 mmol) and the reaction was stirred 1 hour at 80°. The reaction was cooled, 500 mL of water and 900 mL of ether were added, the layers were separated and the ether layer was filtered to remove Pd (0) and combined with 2 further ether washes of the aqueous phase. The combined ether solutions were dried over MgSO$_4$, filtered, stripped and recrystallized from methanol/ether to yield 9.4 g of methyl 4-(diethylaminosulfonyl) benzene-2-propenoate. Six grams of the propenoate was reduced in ethanol at 3.5 atm over 10% Pd on carbon in a Parr Shaker to produce 5.9 g of product as a yellow oil. It was used in that form in Example 269.

EXAMPLE 198

1[4-(Diethylamino)phenyl]-3-ethyl-4-methyl-1H-2,4-benzodiazepine (Formula I: R$^1$, R$^4$, R$^6$=H; R$^2$=Me; R$^3$=Et; R$^5$=

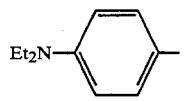

By a procedure analogous to that of Example 41, it is contemplated that 1-[4-(diethylamino)phenyl]-3-ethyl-4-methyl-1H-2,4-benzodiazepine can be synthesized from 2-[4-(diethylamino)benzoyl]benzoic acid (see U.S. Pat. No. 4,106,174), methylhydrazine, and triethylorthopropionate.

EXAMPLE 199

3-Methyl-1-[2-[(1-oxopropyl)amino]phenyl]-4-(3-phenylpropyl)-1H-2,4-benzodiazepine (Formula I: R$^1$, R$^4$, R$^6$=H; R$^2$=(CH$_2$)3Ph; R$^3$=Me; R$^5$=

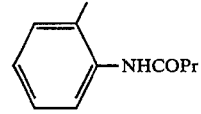

By a procedure analogous to that of Example 41, it is contemplated that 1-(2-aminophenyl)-4-(3-phenylpropyl)-3-methyl-1H-2,4-benzodiazepine can be synthesized from 2-(2-aminobenzoyl)-benzoic acid, hydrazine, bromobenzenepropane and triethyl-orthoacetate. It is further contemplated that this product may be acylated by treatment with propionic anhydride at room temperature to produce 3-methyl-1-[2-[(1-oxopropyl)amino]phenyl]-4-(3-phenylpropyl)-1H-2,4-benzodiazepine.

EXAMPLE 290

(−)-2-[[(1-Methyl)amino]methyl]-α-phenylbenzenemethanamine dihydrochloride (Formula VI: R$^1$=R$^6$=H, R$^2$=Me, R$^5$=Ph)

A mixture of the aminoamide of Example 288 (41.35 g, 0.1297 mol) in concentrated hydrochloric acid (500 mL) was heated to reflux and concentrated sulfuric acid (5 mL) was added and the mixture was refluxed for 23 hours. Additional concentrated sulfuric acid (5 mL) was added and the mixture was refluxed for 13 hours. The reaction mixture was cooled, neutralized with concentrated ammonium hydroxide, poured into a mixture of ether/CH$_2$Cl$_2$ (500 mL), and basified with 35% NaOH until the aqueous layer was at a Ph ≧10. The organic layer was separated, and the aqueous layer was extracted with ether. The organic layers were combined, washed with saturated sodium chloride, dried over Na$_2$SO$_4$ and the solvent was concentrated in vacuo. The residue was purified by column chromatography on silica eluting with MeOtBu and 1–5% isopropylamine to afford 18.76 g of the product as the free base which converted into 23.95 g of the dihydrochloride salt after recrystallization of the salt from Et20/acetone/methanol.

EXAMPLE 292

(a)

(+)-2-[[(1-Methyl)amino]methyl]-α-phenylbenzenemethanamine dihydrochloride (Formula VI: R$^1$=R$^6$=H, R$^2$=Me, R$^5$=Ph)

A mixture of the aminoamide of Example 291 (128.07 g) and a 50% by weight solution of H$_2$SO$_4$/water was heated to reflux for 4 days. The reaction mixture was cooled, neutralized with ammonium hydroxide and treated with 35% NaOH. The mixture was extracted with an ether/CH$_2$Cl$_2$ mixture, and the organic layer was washed with brine, and a small amount of concentrated NaOH. The organic layer was dried over Na$_2$SO$_4$, the solvent was removed in vacuo, and the residue was purified by column chromatography on silica eluting with MeOtBu/1-5% isopropylamine to afford 39.0 g of the product as the free base. The free base was then converted into 42.26 g of the dihydrochloride salt, m.p. 180°-200° C., after recrystallization from MeOH/acetone.

(b)

Alternatively, the desired product may be prepared by treatment of the free base of (R)-(+)-4,5-dihydro-3-ethyl-4-methyl-1-phenyl-1H-2,4-benzodiazepine of Example 171 (3.26 g, 1.2 mol) in toluene (2.75 L) under N$_2$ with ethylene diamine and heating the reaction mixture to reflux for 65 hours. The solvent was removed in vacuo, and the residue was diluted with tert-butylmethyl ether and washed with 0.1 N NaOH. The aqueous layer was separated, extracted with tert-butylmethyl ether and the combined organic layers were washed with brine and dried over Na$_2$SO$_4$. The solvent was removed in vacuo to afford 270.1 g (99.4%) of the product as the free base. The free base (268 g) was dissolved in tert-butylmethyl ether and treated with ethereal.HCl to afford 335 g of the dihydrochloride salt as a blue solid.

Following a procedure substantially similar to that described in Example 292(b) but substituting an appropriately substituted benzodiazepine for (R)-(+)-4,5-dihydro-3-ethyl-4-methyl-1-phenyl-1H-2,4-benzodiazepine, there was prepared the following compounds illustrated in Table AA.

EXAMPLE 301

N-[4-[1-(4,5-Dihydro-1-(4-chlorophenyl)-1,4-dimethyl-1H-2,4-benzodiazepin-3-yl)methoxy]phenyl]methanesulfonamide hydrochloride (Formula I: $R^1=R^6=H$; $R^2=Me$; $R^3=$

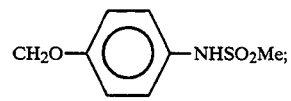

$R^4=Me$; $R^5=4$-Cl-Ph

Following a procedure substantially similar to that described in General Method F2, there was obtained 3.15 g (84%) of N—[4-[1-(4,5-dihydro-1-(4-chlorophenyl)-1,4-dimethyl-1H-2,4-benzodiazepin-3-yl)methoxy]phenyl]methanesulfonamide hydrochloride, m.p. 263–264.5 when recrystallized from ethanol/tert-butylmethyl ether, from 2-[[(1-methyl)amino]methyl]-α-phenyl-α-methylbenzenemethanamine dihydrochloride (2.5 g, 7.18 mmol), trimethylaluminum (12.58 mL, 25.16 mmol), sulfolane (36 mL) and N-[4-(ethoxycarbonylmethoxy)phenyl]methanesulfonamide (2.16 g, 7.91 mmol).

EXAMPLE 303

N-[4-[(4,5-Dihydro-1-(4-chlorophenyl)-4-methyl-1H-2,4-benzodiazepin-3-yl)methyl sulfonyl]phenyl]methanesulfonamide hydrochloride The sulfide of Example 302 (1.88 g, 3.6 mmol) was dissolved in hot acetic acid (42 mL), the solution was cooled to room temperature and 30% hydrogen peroxide (1.0 mL) was added. The mixture was heated to 55° C. for 20 hours, additional 30% H$_2$O$_2$ (0.3 mL) was added and the mixture was heated for another 7 hours. Cyclohexane (1.2 g) was added and the reaction mixture was allowed to stand overnight at room temperature. The solvent was removed in vacuo, and the residue was treated with ethanol, and diluted with ether. A precipitate formed, which was collected and purified by column chromatography on silica eluting with CHCl$_3$/ethanol/trifluoroacetic acid (87/10/3). The residue thus

TABLE AA

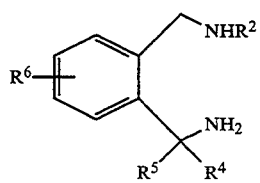

| Example No. | R$^2$ | R$^4$ | R$^5$ | R$^6$ | Yield % | Melting Point (°C.) | Salt | Recrystallized From |
|---|---|---|---|---|---|---|---|---|
| 294A | Me | H | 4-Cl-Ph | H | 98 | — | free base$^{(a)}$ (+)-isomer | — |
| 294B | | | | | — | — | 2 HCL (+)-isomer | MeOH/CH$_2$Cl$_2$/Et$_2$O |
| 294C | | | | | 99 | — | free base$^{(b)}$ (−)-isomer | — |
| 294D | | | | | — | — | 2 HCl (−)-isomer | MeOH/CH$_2$Cl$_2$/Et$_2$O |
| 300 | Me | Me | 4-Cl-Ph | H | 95 | 250–255 | 2 HCl | MeOH/ether |
| 316 | Me | H | 2,4-F$_2$-Ph | H | 79 | — | 2 HCl (−)-isomer | — |
| 317 | Me | H | 2,4-F$_2$-Ph | H | 96 | — | 2 HCl (+)-isomer | — |

$^{(a)}[\alpha]_D^{25} = +78.3°$ (C = 0.78, EtOH).
$^{(b)}[\alpha]_D^{25} = -72.6°$ (C = 0.78, EtOH).

obtained was treated with ethanolic.HCl and the hydrochloride salt was recrystallized from isopropanol to afford 0.78 g of N-[4-[[(4,5-dihydro-1-(4-chlorophenyl)-4-methyl-1H-2,4-benzodiazepin-3-yl) methylsulfonyl]phenyl]methanesulfonamide hydrochloride, m.p. 185°–220° C.

EXAMPLE 303A (+)-N-[4,5-Dihydro-1-(4-chlorophenyl)-4-methyl-1H-2,4-benzodiazepin-3-yl)methylsulfonyl]phenyl]methanesulfonamide hydrochloride Following a procedure substantially similar to that described in Example 303, there was obtained 0.31 g (56%) of (+)-N-[4,5-dihydro-1-(4-chlorophenyl)-4-methyl-1H-2,4-benzodiazepin-3-yl)methyl sulfonyl]phenyl]methane sulfonamide hydrochloride, m.p. 270°–272° C. when recrystallized from acetonitrile, $[\alpha]_D^{25} = +180.6°$ (C=0.615, EtOH); from the sulfide of Example 302A (0.5 g, 1 mmol), acetic acid (12 mL) and 30% $H_2O_2$ (0.37 mL), followed by conversion of the free base thus obtained into the hydrochloride salt and purification of the salt by column chromatography on silica eluting with $CHCl_3$/10% EtOH/3% trifluoroacetic acid.

EXAMPLE 303B (−)-N-[4,5-Dihydro-1-(4-chlorophenyl)-4-methyl-1H-2,4-benzodiazepin-3-yl)methylsulfonyl]phenyl]methanesulfonamide hydrochloride.½ ethanol Following a procedure substantially similar to that described in Example 303, there was obtained 0.213 g (38%) of (−)-N-[4,5-dihydro-1-(4-chlorophenyl)-4-methyl-1H-2,4-benzodiazepin-3-yl)methyl sulfonyl]phenyl]methane sulfonamide hydrochloride.½ ethanol, m.p. <160° C., $[\alpha]_D^{25} = -123.2°$ (C=0.615, EtOH); from the sulfide of Example 302B (0.5 g, 1 mmol), acetic acid (12 mL) and 30% $H_2O_2$ (0.37 mL), followed by conversion of the free base into the hydrochloride salt and purification of the salt by column chromatography on silica (1×) eluting with $CHCl_3$/10% ethanol/3% trifluoroacetic acid and then a second silica column eluting with $CHCl_3$/10% isopropanol/3% trifluoroacetic acid.

EXAMPLE 309

(+)-2-[[(Methyl)amino]methyl]-α-(4-methylthiophenyl) benzenemethanamine dihydrochloride (Formula VI: $R^1=R^6=H$, $R^2=CH_3$, $R^5=4-CH_3S-Ph$, (+)-isomer)

A mixture of (+)-4,5-dihydro-3,4-dimethyl-1-(4-methylthiophenyl)-1H-2,4-benzodiazepine of Example 307 (1.18 g, 4 mmol), ethylene diamine (0.24 g, 4.04 mmol) and toluene (2 mL) was refluxed for 18 hours. The reaction mixture was cooled in an ice-bath, diluted with tert-butylmethyl ether (7 mL) and the precipitate which formed was collected by filtration and washed with tert-butylmethyl ether. The filtrate was washed with water containing a small amount of 2N NaOH, then brine, and finally 1N HCl (2×). The aqueous acidic solution was washed with tert-butylmethyl ether and then was basified with 2N NaOH and extracted with tert-butylmethyl ether. The ether extracts were combined, washed with brine, dried over $Na_2SO_4$ and the solvent was removed in vacuo. The residue was dissolved in ethanol and treated with ethanolic.HCl to afford 0.92 g (67%) of the product as the dihydrochloride salt, m.p. 256°–257° C.

EXAMPLE 310

(−)-2-[[(Methyl)amino]methyl]-α-(4-methylthiophenyl) benzenemethanamine dihydrochloride (Formula VI: $R^1=R^6=H$, $R^2=CH_3$, $R^5=4-CH_3S-Ph$, (−)-isomer)

Following a procedure substantially similar to that described in Example 309, there was obtained (−)-2-[[(methyl)amino]methyl]-α-(4-methylthiophenyl)benzenemethanamine dihydrochloride, from (−)-4,5-dihydro-3,4-dimethyl-1-(4-methylthiophenyl)-1H-2,4-benzodiazepine of Example 308 (2.96 g, 10 mmol), ethylene diamine (0.69 mL, 10.3 mmol) and toluene (6 mL), followed by treatment of the free base with ethanolic.HCl.

EXAMPLE 318

2-(4-Methylthiobenzoyl)benzoic acid

A mixture of phthalic anhydride (37 g, 0.25 mol), thioanisole (31 g, 0.25 mol) and tetrachloroethane (300 mL) was cooled to 3° C. and anhydrous $AlCl_3$ (66.5 g, 0.5 mol) was added while maintaining the reaction temperature at 3°–5° C. After stirring for 10 minutes, the mixture was warmed to room temperature and stirred for 3 hours, then the mixture was stirred at 35°–42° C. for 3 hours and then at room temperature overnight. The mixture was poured into ice water/concentrated HCl, and the aqueous layer was separated and extracted with $CHCl_3$. The organic layers were combined, washed with dilute HCl and filtered through solka Floc. The filtrate was extracted with 1N NaOH and the basic solution was washed with $CH_2Cl_2$ and then was acidified with concentrated HCl. A crystalline product formed, which was collected by filtration, washed with water and recrystallized from ethanol/water to afford 38.3 g (56.3%) of 2-(4-methylthiobenzoyl)benzoic acid, m.p. 151°–155 ° C.

EXAMPLE 319

2-(2,4-Difluorobenzoyl)benzoic acid

To a mixture of phthalic anhydride (64.8 g, 438 mmol), tetrachloroethane (600 mL) and 1,3-difluorobenzene (100 g, 877 mmol) was added anhydrous $AlC1_3$ (141 g, 964 mmol) over 20 minutes while maintaining the reaction temperature below 40° C. The temperature was increased to 90° C. for 2 hours, the reaction mixture was cooled and poured into ice/6N HCl. The mixture was extracted with ether (2×1.2 L) and the combined ether extracts were dried over $Na_2SO_4$. The solvent was removed in vacuo and the residue was recrystallized from hot ethyl acetate to afford 86.5 g (75%) of 2-(2,4-difluorobenzoyl)benzoic acid, m.p. 129°–131 ° C.

EXAMPLE 320

2-Methyl-4-(4-chlorophenyl)-1-(2H)-phthalazinone

Following a procedure substantially similar to that described in Example 185, there was obtained 92.22 g (87.4%) of 2-methyl-4-(4-chlorophenyl)-1-(2H)-phthalazinone, m.p. 151°–152.5° C., from methylhydrazine (19.95 g, 0.4287 mol), toluene (260 mL) and 2-(4chlorobenzoyl)benzoic acid (103.66 g, 0.3897 mol).

EXAMPLE 321

2-Methyl-4-(4-methoxyphenyl)-1-(2H)-phthalazinone

Following a procedure substantially similar to that described in Example 185, there was obtained 39.65 g (78%) of 2-methyl-4-(4-methoxyphenyl)-1-(2H)-phthalazinone, from 2-(4-methoxybenzoyl)benzoic acid (49.65 g, 0.19 mol) methylhydrazine (10.3 mL) and toluene (150 mL).

EXAMPLE 322

2-Methyl-4-(4-methylthiophenyl)-1-(2H)-phthalazinone

Following a procedure substantially similar to that described in Example 185, there was obtained 37.42 g (78%) of 2-methyl-4-(4-methylthiophenyl)-1-(2H)-phthalazinone, m.p. 166.5°–168.5° C., from 2-(4-methylthiobenzoyl)benzoic acid (46.2 g, 0.17 mol), methyl hydrazine (9.2 g, 0.2 mol) and toluene (400 mL).

EXAMPLE 323

2-Methyl-4-(2,4-difluorophenyl)-1-(2H)-phthalazinone

Following a procedure substantially similar to that described in Example 185, there was obtained 20.0 g of 2-methyl-4-(2,4-difluorophenyl)-1-(2H)-phthalazinone, as a yellow solid, from 2-(2,4-difluorobenzoyl)benzoic acid (52.4 g, 0.2 mol), methyl hydrazine (11.2 mL, 0.21 mol) and toluene (500 mL).

EXAMPLE 324

N-[4-(Ethoxycarbonylmethoxy)phenyl]methanesulfonamide (Formula $R^3COOR^{12}$: $R^3=$

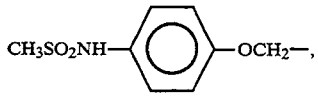

$R^{12}=$ethyl)

The product was made by procedures which are well known in the art, that is, by alkylation of 4-nitrophenol (29.2 g, 0.21 mol) with ethyl chloroacetate (24.5 g, 0.20 mole) in the presence of potassium carbonate (30.4 g, 0.22 mol), potassium iodide (0.5 g) and acetonitrile (150 mL) to afford ethyl 4-nitrophenoxyacetate (33 g, 73.3%), m.p. 75°–76° C. after recrystallization from tert-butylmethyl ether; hydrogenation of the latter (22.5 g) at 50 psi in ethyl acetate (200 mL) in the presence of 10% palladium on Carbon (0.3 g) to afford 22.5 g (97%) of ethyl 4-aminophenoxyacetate, m.p. 157°–158° C.; and treatment of the latter (18.52 g, 0.08 mol) with methanesulfonyl chloride (12.6 g, 0.11 mol) in CH$_2$Cl$_2$ (250 mL) in the presence of pyridine (35 mL) to afford N-[4-(ethoxycarbonylmethoxy)phenyl]methanesulfonamide, 20.06 g (92%), m.p. 77.3°–78.5° C. after recrystallization from ethanol.

EXAMPLE 325

N-[4-(Ethoxycarbonylmethylthio)phenyl]methane sulfonamide (Formula $R^3COOR^{12}$: $R^3=$

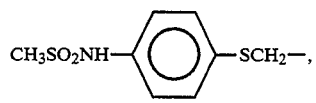

$R^{12}=$ethyl)

The product was made by procedures which are well known in the art, that is, by esterification of 4-aminothiophenoxy acetic acid (5.49 g, 0.03 mol) with ethanol (50 mL) in sulfuric acid (2 mL) to afford 6.95 g (93.5%) of ethyl 4-aminophenylthioacetate hydrochloride, m.p. 154°–155.5° C., after formation of the hydrochloride salt by treatment of the free base with ethanolic.HCl; and treatment of the latter (6.43 g, 0.026 mol) with methanesulfonyl chloride (3.44 g, 0.03 mol) in CH$_2$Cl$_2$ (60 mL) in the presence of pyridine (6 mL) to afford 6.9 g (95.4%) of N-[4-(ethoxycarbonylmethylthio)phenyl]methanesulfonamide, m.p. 46°–48° C. after recrystallization from tert-butylmethyl ether/hexane.

EXAMPLE 326

N-[4-(Ethoxycarbonylethyl)phenyl]methanesulfonamide (Formula $R^3COOR^{12}$: $R^3=$

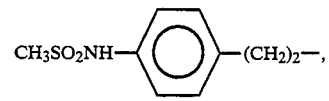

$R^{12}=$ethyl)

The product was made by reducing ethyl 4-nitrocinnamate (110.6 g, 0.5 mol) with 10% palladium on Carbon (4.0 g) in 95% ethanol (2L) in the presence of ammonium formate (126 g) to afford ethyl 3-(4-aminophenyl)propionate which was sulfonated with methanesulfonyl chloride in CH$_2$Cl$_2$ in the presence of pyridine to produce 102 g (75.2%) of N-[4-(ethoxycarbonylethyl)phenyl]methanesulfonamide.

EXAMPLE 327

2-Methyl-4-(4-methylsulfonylphenyl)-1-(2H)-phthalazinone

To a solution of 2-methyl-4-(4-methylthiophenyl)-1-(2H)-phthalazinone (14.15 g, 0.05 mol) in acetic acid (330 mL) was added 30% H$_2$O$_2$ (22 mL). The mixture was heated to 35° C. overnight, additional 30% H$_2$O$_2$ (10 mL) was added and the mixture was stirred at 35° C. for 2 hours and finally one final portion of 30% H$_2$O$_2$ (10 mL) was added and the mixture was stirred for another 2 hours at 35° C. The reaction mixture was poured into water (1 L)/ice and the solid thus obtained was collected by filtration, washed with water, then ether, and then was dried to afford 14.6 g (93%) of 2-methyl-4-(4-methylsulfonylphenyl)-1-(2H)-phthalazinone as a pale yellow solid, m.p. 218°–220° C. when recrystallized from ethanol/chloroform (2×).

EXAMPLE 331

(a)

N-Methyl-4-bromophenyl sulfonamide

A mixture of 4-bromophenylsulfonyl chloride (25.5 g, 100 mmol), CH$_2$Cl$_2$ (400 mL) and pyridine (1.6 g, 110 mol) was cooled to 0° C. and methylamine gas was added over 45 minutes. The mixture was warmed to room temperature, the solvent was removed in vacuo and the residue was dissolved in $CH_2Cl_2$ and washed with 2N HCl (2×100 mL), water (1×200 mL), saturated $NaHCO_3$ (1×200 mL) and then brine (1×200 mL). The solvent was dried over $MgSO_4$ and the solvent was removed in vacuo to afford 23 g of N-methyl-4-bromophenylsulfonamide.

(b)

N-Methyl-N-(4-methoxybenzyl)-4-bromophenylsulfonamide

To a solution of N-methyl-4-bromophenylsulfonamide (2.5 g, 10 mmol) in DMF (20 mL) at room temperature was added in portions NaH (264 rag, 11 mmol). The mixture was stirred for 45 minutes and then p-methoxybenzylchloride (1.49 mL, 11 mmol) was added dropwise. The mixture was stirred for 1 hour, quenched with water and the precipitate which formed was collected by filtration and dried in vacuo at 60° C. to afford 3.6 g (97%) of N-methyl-N-(4-methoxybenzyl)-4-bromophenylsulfonamide.

(c)

N-Methyl-N-(4-methoxybenzyl)-4-(2-(methoxycarbonyl)ethenyl)phenylsulfonamide

A mixture of N-methyl-N-(4-methoxybenzyl)-4-bromophenylsulfonamide (1.68 g, 4.54 mmol), $Pd(OAc)_2$ (20 mg, 0.091 mmol), tri-o-tolylphosphine (55 mg, 0.18 mmol), triethylamine (1.25 mL), acetonitrile (2.5 mL) and methyl acrylate (0.83 mL, 9.08 mmol) were placed in a stainless steel bomb and heated to about 120° C. for 4 hours. The mixture was cooled to 0° C., the bomb was vented, and the solid reaction mixture was collected, washed with ether and dried to afford 2.1 g of crude product which was used directly in the next step without further purification.

(d)

N-Methyl-N-(4-methoxybenzyl)-4-(2-(methoxycarbonyl)ethyl)phenylsulfonamide

To a suspension of the sulfonamide of Example 331 (c) (2.1 g, 4.54 mmol) in ethanol (125 mL) under nitrogen was added 10% Pd/C (0.6 g). The mixture was placed on a Parr hydrogenator at 50 psi of hydrogen for 2 hours, the catalyst was removed by filtration and the solvent was removed in vacuo. The residue was recrystallized from $Et_2O$/MeOH, extracted with $CH_2Cl_2$, washed with water, then brine and was dried over $MgSO_4$. The solvent was removed in vacuo to afford 1.41 g (82%) of N-methyl-N-(4-methoxybenzyl)-4-(2-(methoxycarbonyl)ethyl)phenylsulfonamide as a colorless oil.

(e)

4,5-Dihydro-4-methyl-1-phenyl-3-[2-(4-(N-methyl-N-4-methoxybenzylaminosulfonyl)phenyl)ethyl]-1H-2,4-benzodiazepine To a suspension of 2-[[(1-Methyl)amino]methyl]-α-phenylbenzenemethanamine dihydrochloride (2.59 g, 8.59 mmol) in toluene (75 mL) at 0° C. under nitrogen was added 2M trimethylaluminum (9.0 mL, 18 mmol) over 10 minutes. The mixture was warmed to room temperature and after 2 hours N-methyl-N-(4-methoxybenzyl)-4-(2-(methoxycarbonyl)ethyl)phenylsulfonamide (3.4 g, 9.02 mmol) was added in one portion. The reaction mixture was heated to reflux for 2 hours, cooled to room temperature, partitioned between saturated $Na_2CO_3/CH_2Cl_2$ and filtered through solka floc. The organic layer was separated, dried over $Na_2SO_4$ and the solvent was removed in vacuo. The residue was azeotroped with ethanol (2×), decolorized with charcoal and the solvent was removed in vacuo to afford 3.6 g of 4,5-dihydro- 4-methyl-1-phenyl-3-[2-(4-(N-methyl-N-4-methoxybenzylaminosulfonyl)phenyl)ethyl]-1H-2,4-benzodiazepine.

(f)

4,5-Dihydro-4-methyl-1-phenyl-3-[2-(4-(N-methylaminosulfonyl)phenyl)ethyl]-1H-2,4-benzodiazepine To a solution of the benzodiazepine of Example 331E (2.0 g, 3.67 mmol) in $CH_2Cl_2$ (14.6 mL) was added trifluoroacetic acid (5.84 mL, 77 mmol) dropwise over 10 minutes. The mixture was stirred for 4 hours, and then was added to a solution of saturated $Na_2CO_3$ (75 mL) at 0° C. The mixture was extracted with $CH_2Cl_2$, the aqueous layer was back extracted with additional $CH_2Cl_2$ and the organic layers were combined, dried over $MgSO_4$ and the solvent was removed in vacuo to afford 2.5 g of 4,5-dihydro-4-methyl-1-phenyl-3-[2-(4-(N-methylaminosulfonyl)phenyl)ethyl]-1H-2,4-benzodiazepine. The free base was treated with ethanolic.HCl to afford the hydrochloride salt, and the salt was purified by column chromatography on neutral $Al_2O_3$ eluting with 5% MeOH/$CH_2Cl_2$. The residue was recrystallized from $CH_2Cl_2$/ether to afford 1.16 g (68%) of the product as the hydrochloride salt, m.p. 101(dec.).

EXAMPLE 332

N-[4-(Ethoxycarbonylethyl)phenyl]trifluoromethane sulfonamide

To a solution of ethyl 3-(4-aminophenyl)propionate (7.87 g, 40.7 mmol) in $CH_2Cl_2$ (75 mL) under $N_2$ was added triethylamine (5.96 mL, 42.76 mmol). The mixture was cooled to −78° C. and trifluoromethanesulfonic anhydride (7.19 mL, 42.76 mmol) in $CH_2Cl_2$ (20 mL) was added via syringe. The reaction mixture was stirred at −78° C. for 15 minutes, then at room temperature for 15 minutes and was then shaken with water (100 mL) and 2N HCl (5 drops). The organic layer was separated, dried over $MgSO_4$ and concentrated in vacuo. The residue was dissolved in $Et_2O$ (100 mL), washed with water/2N HCl (5 drops) (3×), then brine, and was dried over MgSO4 and concentrated in vacuo. The residue was taken back up in ether and washed with water and 2N NaOH. The aqueous phase was separated, acidified with concentrated HCl, saturated with sodium chloride and extracted with ether. The combined ether extracts were washed with brine, dried over $Na_2SO_4$ and concentrated in vacuo to afford 11.894 g of N-[4-(ethoxycarbonylethyl)phenyl]trifluoromethanesulfonamide as an oil.

EXAMPLE 334

2-(2-(4-Pyridinyl)ethyl)-4-(4-chlorophenyl)-1(2H)-phthalazinone

A mixture of 2-(4-chlorobenzoyl)benzoic acid (65.13 g, 0.25 mol), toluene (500 mL) and pyridylethyl hydrazine (37.0 g, 0.27 mol) was refluxed for 1 hour while removing water with a Dean-Stark trap. The mixture was concentrated in vacuo, and the residue was diluted with tert-butylmethyl ether (200 mL). A precipitate formed, which was collected by filtration, dissolved in CH2Cl2, filtered through solka floc and the filtrate was diluted with hexane. The precipitate which formed was collected by filtration, and recrystallized from hot ethanol to afford 46.5 g (51.4%) of 2-(2-(4-pyridinyl)ethyl)-4-(4-chlorophenyl)-1(2H)-phthalazinone, m.p. 142°–144° C.

Iminoethers (alkoxyimines)

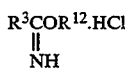

The ethoxy and methoxy imines used for condensation with the diamines were obtained from the corresponding nitriles by methods well known in the art. In general, the nitrile was dissolved in ether, chloroform or a mixture thereof, 1.1 equivalents of alkanol was added, 1.1 equivalents of dry HCl gas was bubbled in, and the mixture was held at 5° for 24–48 hours; the hydrochloride salt of the iminoether was recovered by simple filtration. The trialkylorthoesters were obtained by treating the corresponding iminoether with the appropriate alkanol under conditions known in the art.

EXAMPLE 337

N-[4-(Ethoxycarbonylmethoxy)-3-(methyl)phenyl]methanesulfonamide (Formula R³COOR¹²: R³=

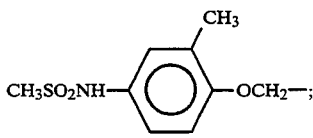

R¹²=ethyl)

The product was prepared by procedures which are well known in the art, that is, by the alkylation of 4-nitro-2-methylphenol (2. 508 g, 0. 0164 mol) with ethyl bromoacetate (3.00 g, 0.018 mol) in acetonitrile (50 mL) in the presence of potassium carbonate (2.76 g) to afford ethyl 4-nitro-2-methylphenoxyacetate (4.0 g, 100%); hydrogenation of the latter (4.0 g, 0.0164 mol) in ethanol (250 mL) in the presence of 10% palladium on carbon (1.0 g) to afford ethyl 4-amino-2-methylphenoxyacetate; which was then dissolved in CH2Cl2 (50 mL) and treated with pyridine (4.0 mL), followed by methanesulfonyl chloride (1.88 g) in CH2Cl2 (5.0 mL) to afford 3.27 g (69.4%) of N-[4-(ethoxycarbonylmethoxy)-3-(methyl) phenyl]methanesulfonamide, m.p. 83°–84 ° C., after purification by column chromatography on silica.

EXAMPLE 338

N-[4-(Ethoxycarbonylmethoxy)-2-(methyl)phenyl]methanesulfonamide (Formula R³COOR¹²: R³=

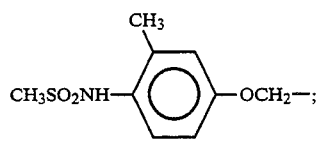

R¹²=ethyl)

The product was prepared by the alkylation of 4-nitro-3-methylphenol (15.3 g) with ethyl bromoacetate (16.7 g) in DMF (150 mL) in the presence of potassium carbonate (13.8 g) to afford ethyl 4-nitro-3-methylphenoxyacetate; hydrogenation of the latter (7.18 g, 0.03 mol) in ethanol (250 mL) in the presence of 5% palladium on carbon (2.1 g) to afford 6.20 g (99%) of ethyl 4-amino-3-methylphenoxyacetate as a brown oil; and treatment of the latter (6.2 g, 0.0296 mol) in CH2Cl2 (100 mL) with pyridine (10 mL), followed by methanesulfonylchloride (3.73 g, 0.033 mol) to afford 6.54 g (76.9%) of N-[4-(ethoxycarbonylmethoxy)-2-(methyl)phenyl]methanesulfonamide, m.p. 93°–94 ° C., after recrystallization from ethanol.

EXAMPLE 341

N-[4-(Ethoxycarbonylmethoxy)-3-(methoxy)-phenyl]methane sulfonamide (Formula R³COOR¹²: R³=

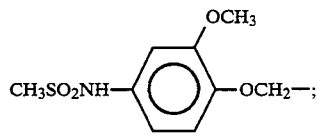

R¹²=ethyl)

The product was prepared by the alkylation of 4-nitro-2-methoxyphenol (10.0 g, 0.059 mol) with ethyl bromoacetate (10.0 g, 0.06 mol) in acetonitrile (50 mL) in the presence of potassium carbonate (8.0 g) to afford 14.33 g (95%) of ethyl 4-nitro-2-methoxyphenoxyacetate as a yellow solid, m.p. 87°–88° C., after recrystallization from tert-butylmethyl ether; hydrogenation of the latter (13.08 g, 0.051 mol) in THF (125 mL)/ethanol (125 mL) in the presence of 10% Pd/C (1.0 g) to afford 11.5 g (100%) of ethyl 4-amino-2-methoxyphenoxyacetate as a pink oil; and then treatment of the latter (11.5 g, 0.051 mol) in CH2Cl2 (100 mL) with pyridine (10 mL), followed by methanesulfonyl chloride (6.43 g, 0.056 mol) to afford 12.328 g (79.6%) of N-[4-(ethoxycarbonylmethoxy)-3-(methoxy)phenyl]methanesulfonamide, m.p. 118°–119° C., after purification by treatment with charcoal and filtration through silica eluting with ethyl acetate.

EXAMPLE 343

4,5-Dihydro-1-(4-chlorophenyl)-4-methyl-3-(4-pyridylmethyl)1H-2,4-benzodiazepine dihydrochloride (Formula I: R¹=R⁴=R⁶=H; R²=Me; R³=

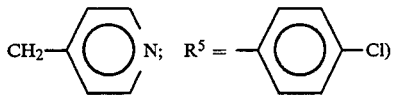

To a mixture of 2-[[(N-methyl)amino]methyl]-α-phenylbenzenemethanamine dihydrochloride (Formula VI: $R^1$=H; $R^2$=Me; $R^5$=4-Cl-Ph; $R^6$=H) (8.34 g, 0.025 mol) in sulfolane (75 mL) and toluene (25 mL) under nitrogen was added triisobutyl aluminum (38.0 mL, 0.076 mol). The mixture was stirred for 30 minutes, and then ethyl 4-pyridylacetate (5.36 g, 0.0325 mol) was added. The mixture was heated to 110° C. for 2 hours, the solution was cooled, poured into a saturated Rochelle salt solution (200 mL) and the mixture was diluted with water (200 mL) and extracted with $CH_2Cl_2$ (3×). The organic extracts were combined, washed with water, and the solvent was removed in vacuo to afford an oil. The oil was treated with ethyl acetate/HCl to afford the hydrochloride salt which was recrystallized from ethanol/acetonitrile, then isopropanol/acetonitrile to afford 4,5-dihydro-1-(4-chlorophenyl)-4-methyl-3-(4-pyridylmethyl)-1H-2,4-benzodiazepine dihydrochloride as a white solid, m.p. 185°–190° C. (dec.).

EXAMPLE 344

N-[4-(Ethoxycarbonylmethoxy)-3-chlorophenyl]methanesulfonamide (Formula $R^3COOR^{12}$: $R^3$=

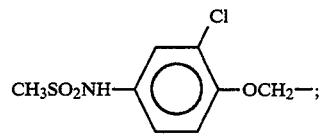

$R^{12}$=ethyl)

The product was prepared by the alkylation of 2-chloro-4-nitrophenol (17.35 g) in DMF (150 mL) with ethyl bromoacetate (16.7 g) in the presence of potassium carbonate (13.8 g) to afford 19.6 g (75.6%) of ethyl 4-nitro-2-chlorophenoxyacetate as a white solid, m.p. 73°– 74° C.; hydrogenation of the latter (10.0 g, 38.5 mmol) in ethanol (200 mL) on a Parr hydrogenator in the presence of 5% platinum on carbon (sulfided) (200 mg) afforded 8.1 g (92%) of ethyl 4-amino-2-chlorophenoxyacetate, m.p. 59°–62° C., after recrystallization from tert-butylmethylether, and finally, treatment of the latter (7.3 g, 31.8 mmol) in $CH_2Cl_2$ (75 mL) at 5° C. with pyridine (3.0 mL, 38.7 mmol) and methanesulfonyl chloride (2.29 mL) to afford N-[4-(ethoxycarbonylmethoxy)-3-chlorophenyl]methanesulfonamide, m.p. 87°–88° C. after recrystallization from tert-butylmethylether.

EXAMPLE 348

(+)-4,5-Dihydro-4-methyl-1-phenyl-3-[2-[(4-methylsulfonylamino)phenyl]ethyl]-1H-2,4-benzodiazepine.½ hydrate (Formula I: $R^1$=$R^4$=$R^6$=H; $R^2$=Me; $R^3$=

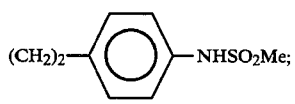

$R^5$=Ph)

A solution of (+)-4,5-dihydro-4-methyl-1-phenyl-3-[2-[(4-amino)phenyl]ethyl]-1H-2,4-benzodiazepine (3.00 g, 8.44 mmol) in $CH_2Cl_2$ (50 mL) was treated with an excess of ethereal.HCl, and the dihydrochloride salt which formed was isolated by removing the solvent in vacuo. The dihydrochloride salt was treated with $CH_2Cl_2$ (60 mL) and pyridine (25 mL) and the solution was cooled to 0° C. Methanesulfonyl chloride (1.00 mL) in $CH_2Cl_2$ (4.0 mL) was added and the reaction mixture was stirred at 0° C. for 30 minutes, then at room temperature for 2.5 hours. The reaction mixture was diluted with $CH_2Cl_2$ (50 mL), water (100 mL) and a saturated $Na_2CO_3$ solution (75 mL) and the organic layer was separated and dried over $Na_2SO_4$. The solvent was removed in vacuo and the residue was recrystallized from ethanol/ether to afford 3.15 g of (+)-4,5-dihydro-4-methyl-1-phenyl-3-[2-[(4-methylsulfonylamino)phenyl]ethyl]-1H-2,4-benzodiazepine.½ hydrate, m.p. 210°–211° C., $[\alpha]_D^{22}$=+204° (C=0.5, MeOH). An additional 0.44 g of product was also obtained by recrystallization of the mother liquor from ethanol/ether.

EXAMPLE 351

(−)-4,5-Dihydro-4-methyl-1-phenyl-3-[2-[(4-methylsulfonylamino)phenyl]ethyl]-1H-2,4-benzodiazepine.½ hydrate (Formula I: $R^1$=$R^4$=$R^6$=H; $R^2$=Me; $R^3$=

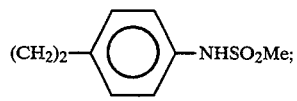

$R^5$=Ph)

Following a procedure similar to that described in Example 348, there was obtained 2.15 g (71%) of (−)-4,5-dihydro-4-methyl-1-phenyl-3-[2-[(4-methylsulfonylamino)phenyl]ethyl]-1H-2,4-benzodiazepine.½ hydrate, m.p. 211.5–212.5 after recrystallization from ethanol/ether (2×); from the dihydrochloride salt of (−)-4,5-dihydro-4-methyl-1-phenyl-3-[2-[(4-amino)phenyl]ethyl]-1H-2,4-benzodiazepine (2.49 g, 7 mmol of free base), $CH_2Cl_2$ (50 mL), pyridine (20 mL) and methanesulfonyl chloride (0.83 mL, 10.5 mmol).

EXAMPLE 353

4,5-Dihydro-4-methyl-1-phenyl-3-[2-[(4-amino)phenyl]ethyl]-1H-2,4-benzodiazepine monohydrochloride (Formula I: $R^1$=$R^4$=$R^6$=H; $R^2$=Me; $R^3$=

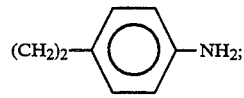

$R^5$=Ph)

To a solution of 4,5-dihydro-4-methyl-1-phenyl-3-[2-[(4-nitro)phenyl]ethyl]-1H-2,4-benzodiazepine (12.70 g, 0.0278 mol) in ethanol (150 mL) under nitrogen was added 10% palladium on carbon (1.91 g). The reaction mixture was hydrogenated on a Parr hydrogenator at 50 psi for 85 minutes. The catalyst was removed by filtration, the filtrate was concentrated in vacuo and the residue was recrystallized from ethanol/ether and then methanol/t-BuOMe to afford 9.86 (90.5%) of 4,5-dihydro-4-methyl-1-phenyl-3-[2-[(4-amino)phenyl]ethyl]-1H-2,4-benzodiazepine monohydrochloride, m.p. 158°–160.5° C.

EXAMPLE 354

4,5-Dihydro-4-methyl-1-phenyl-3-[2-[(4-ethylsulfonylamino)phenyl]ethyl]-1H-2,4-benzodiazepine monohydrochloride (Formula I: $R^1=R^4=R^6=H$; $R^2=Me$; $R^3=$

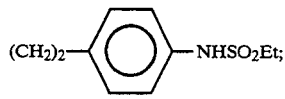

$R^5=Ph$)

To a cooled solution of 4,5-dihydro-4-methyl-1-phenyl-3-(2-[(4-amino)phenyl]ethyl]-1H-2,4-benzodiazepine monohydrochloride (3.00 g, 7.65 mmol) in CH$_2$Cl$_2$ (75 mL) under nitrogen was added pyridine (25 mL), followed by ethanesulfonyl chloride (0.87 mL, 9.18 mmol) in CH$_2$Cl$_2$ (5.0 mL). The reaction mixture was stirred at 0° C. for 1 hour, and then at room temperature for 1 hour. The mixture was treated with water (50 mL) and saturated Na$_2$CO$_3$ (25 mL), and the organic layer was separated. The aqueous layer was extracted with CH$_2$Cl$_2$ (100 mL) and the combined organic layers were washed with water (1×) and dried over Na$_2$SO$_4$. The solvent was removed in vacuo and the residue was treated with ethanolic.HCl and the hydrochloride salt thus formed was recrystallized from methanol/t-BuOMe to afford 2.915 g of 4,5-dihydro-4-methyl-1-phenyl-3-[2-[(4-ethylsulfonylamino)phenyl]ethyl]-1H-2,4-benzodiazepine monohydrochloride as an orange powder, m.p. 240°–241° C.

EXAMPLE 356

2-Methyl-4-(4-bromophenyl)-1-(2H)-phthalazinone (Formula VIII: $R^2=Me$; $R^5=4$-Br-Ph; $R^6=H$)

To a suspension of 2-(4-bromobenzoyl)benzoic acid (15.0 g, 49.2 mmol) in toluene (75 mL) at room temperature was added methylhydrazine (2.88 mL, 54.1 mmol). The reaction mixture was heated to reflux while collecting water in a Dean Stark trap for 3 hours, additional methylhydrazine (2.0 mL) was added and refluxing was continued for 15 minutes. The reaction mixture was cooled to room temperature and the product was collected by filtration and dried in vacuo to afford 13.4 g (87%) of 2-methyl-4-(4-bromophenyl)-1-(2H)-phthalazinone, m.p. 168°–170 ° C.

EXAMPLE 359

2-Methyl-4-(4-nitrophenyl)-1-(2H)-phthalazinone (Formula VIII: $R^2=Me$; $R^5=4$-NO$_2$-Ph; $R^6=H$)

Following a procedure similar to that described in Example 356, there was obtained 15.3 g (54%) of 2-methyl-4-(4-nitrophenyl)-1-(2H)-phthalazinone, m.p. 200°–202° C., after recrystallization from hot methanol; from 2-(4-nitrobenzyl)benzoic acid (27.1 g, 100 mmol), toluene (500 mL) and methyl hydrazine (6.38 mL, 120 mmol).

EXAMPLE 360

2-Methyl-4-(4-aminophenyl)-1-(2H)-phthalazinone (Formula VIII: $R^2=Me$; $R^5=4$—NH$_2$-Ph; $R^6=H$)

To a suspension of 2-methyl-4-(4-nitrophenyl)-1-(2H)-phthalazinone (3.0 g, 10.7 mmol) in ethanol (150 mL) under N$_2$ was added 10% Pd/C (0.75 g). The mixture was hydrogenated on a Parr hydrogenator at 50 psi for 2 hours, the catalyst was removed by filtration and the solvent was removed in vacuo to afford 2.67 g (97%) of 2-methyl-4-(4-aminophenyl)-1-(2H)-phthalazinone as a yellow solid.

EXAMPLE 361

2-Methyl-4-(4-methylsulfonylaminophenyl)-1-(2H)-phthalazinone (Formula VIII: $R^2=Me$; $R^5=4$—CH$_3$SO$_2$NH-Ph; $R^6=H$)

To a mixture of 2-methyl-4-(4-aminophenyl)-1-(2H)-phthalazinone (8.77 g, 34.9 mmol), CH$_2$Cl$_2$ (300 mL) and pyridine (3.11 mL, 38.4 mmol) at 0° C. was added dropwise methanesulfonyl chloride (2.97 mL, 38.4 mmol) in CH$_2$Cl$_2$ (20 mL) over 15 minutes. The reaction mixture was warmed to room temperature and stirred for 12 hours. Additional pyridine (0.5 mL) and methanesulfonyl chloride (0.5 mL) was added and the mixture was stirred as such for 2 hours. The reaction mixture was poured into 2N HCl, the organic layer was separated and then washed with water and dried over Na$_2$SO$_4$. The solvent was removed in vacuo and the residue was azeotroped with toluene and CH$_2$Cl$_2$ to afford 9.0 g (78%) of 2-methyl-4-(4-methylsulfonylaminophenyl)-1-(2H)-phthalazinone as a yellow solid.

EXAMPLE 365

2-(Isonicotinoyl)benzoic acid (Formula XIII: $R^5=4$-pyridyl; $R^6=H$)

To a warmed mixture of ether (500 mL) and magnesium turnings (14.9 g, 0.614 mol) was added dropwise 2-bromotoluene (105 g, 0.614 mol) and then a crystal of iodine. The reaction mixture was refluxed for 1 hour, then 4-cyanopyridine (30.2 g, 0.29 mol) in THF (130 mL) was added dropwise over 45 minutes. The mixture was refluxed for 1.5 hours, cooled to room temperature and quenched with 6N HCl (200 mL). The organic phase was separated, the aqueous phase was extracted with Et$_2$O, and the combined ether phases were extracted with 2N HCl. The aqueous acidic phases were combined, basified with concentrated NH$_4$OH, extracted with Et$_2$O (3×750 mL) and the combined organic layers were dried over Na$_2$SO$_4$ and the solvent was removed in vacuo to afford 54 g of crude 2-isonicotinoyltoluene.

The latter (54 g, 274 mmol) was mixed with water (3 L), and MgSO$_4$ (33 g, 274 mmol) and the mixture was heated to reflux. Potassium permanganate (188 g, 1.99 mol) was then added in portions over 15 minutes. The mixture was refluxed for 6 hours, cooled and filtered through celite. The filtrate was concentrated to 0.5 L, diluted with ethanol (500 mL) and the precipitate which formed was filtered and washed with ethanol. The filtrate was concentrated in vacuo and the residue was treated with acetic acid (50 mL) to give a white solid which was collected by filtration. The solid was triturated with ether and filtered to afford 16.79 g (27%) of 2-(isonicotinoyl)benzoic acid, m.p. 191°–193° C.

EXAMPLE 366

2-Methyl-4-(4-pyridyl)-1-(2H )-phthalazinone (Formula VIII: $R^2=Me$; $R^5=4$-pyridyl; $R^6=H$)

To a suspension of 2-(isonicotinoyl)benzoic acid (10.0 g, 44.1 mmol) in toluene (50 mL) was added methyl hydrazine (2.59 mL, 48.6 mmol). The mixture was heated to reflux while collecting water in a Dean-Stark trap for 6 hours. Additional methylhydrazine (2.59 mL) was added and the mixture was heated to reflux for another 5 hours. The reaction mixture was cooled to room temperature and the product was collected by filtration. The product was recrystallized from hot methanol to afford 8.5 g (81%) of 2-methyl-4-(4-pyridyl)-1-(2H)-phthalazinone, m.p. 173°-174 ° C.

EXAMPLE 367

Orthoester of Formula:

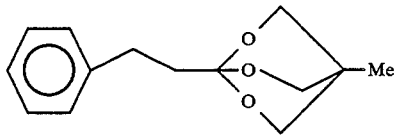

To a solution of hydrocinnamic acid (12.0 g, 79.8 mmol) in ether (400 mL) at room temperature under nitrogen was added dimethylamino pyridine (0,951 g, 7.8 mmol), oxetane (7.89 mL, 87 mmol) and dicyclohexylcarbodiimide (17.9 g, 87 mmol). The mixture was stirred at room temperature for 2 hours, the mixture was filtered and the filtrate was concentrated in vacuo. The residue was distilled under reduced pressure, and then passed through a silica column eluting with ethyl acetate to afford 12.8 g (69%) of an oxetane ester of the formula:

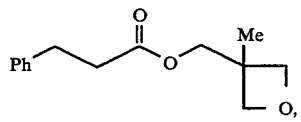

as an oil.

The latter (12.8 g, 54.7 mmol) was dissolved in CH₂Cl₂ (55 mL), cooled to −10° C. under nitrogen and then BF₃.Et₂O (1.69 mL, 13.7 mmol) was added via syringe over one minute. The mixture was stirred at −10° C. for 2 hours, then at 0° C. for 1 hour and the mixture was then warmed to room temperature and quenched with triethylamine. The solvent was removed in vacuo to afford 10.5 g (87%) of the desired orthoester.

EXAMPLE 368

4,5-Dihydro-4-methyl-1-(4-pyridyl)-3-[2-Phenylethyl]-1H-2,4-benzodiazepine fumarate (Formula I: $R^1=R^4=R^6=H$; $R^2=Me$; $R^3=CH_2CH_2Ph$; $R^5=$4-pyridyl)

To a mixture of 2-(N-methylaminomethyl)-α-(4-pyridyl)benzenemethanamine trihydrochloride of Example 146A (1.50 g, 4.46 mmol) in methanol (40 mL) at room temperature was added sodium acetate (0.92 g, 11.2 mmol) and the orthoester of Example 367 (1.31 g, 5.58 mmol). The mixture was heated to reflux for 5 hours, additional orthoester (1.31 g) was added and the mixture was refluxed for another 12 hours. The mixture was cooled to room temperature, the solvent was removed in vacuo and the residue was partitioned between half-saturated Na₂CO₃ and t-BuOMe. The aqueous layer was extracted with additional t-BuOMe and the organic layers were combined, dried over Na₂SO₄ and concentrated in vacuo. The residue was treated with fumaric acid and the mixture was dissolved in hot ethanol and diluted with ether. The fumarate salt was collected by filtration to afford 0.9 g (57%) of 4,5-dihydro-4-methyl-1-(4-pyridyl)-3-[2-phenylethyl]-1H-2,4-benzodiazepine fumarate, m.p. 173°-176° C.

EXAMPLE 369

2-(2-Methoxyethyl)-4-(4-chlorophenyl)-1-(2H)-phthalazinone (Formula VIII: $R^2=CH_2CH_2OMe$; $R^5=$4-Cl-Ph; $R^6=H$)

A slurry of 2-(4-chlorobenzoyl) benzoic acid (104 g, 0.4 mol) in toluene (400 mL) was treated with hydrazine hydrate (22.5 g, 0.45 mol) and the mixture was heated to reflux for 1.5 hours with removal of water by a Dean Stark trap. The reaction mixture was cooled and 101.28 g (98.7%) of 4-(4-chlorophenyl)-1-(2H)-phthalazinone, m.p. 270°-272 ° C., was collected.

The latter (25.6 g, 0.1 mol) is then added over 2 hours to a suspension of sodium hydride (4.8 g, 0.12 mol, prewashed with hexane) in DMSO (250 mL) under nitrogen. The mixture was stirred for 3/4 hour and then 2-chloroethylmethyl ether (12.29 g, 0.13 mol) in DMSO (25 mL) was added over 5 minutes. The reaction mixture was stirred overnight. The mixture was heated to 40° C. for 1.5 hours, additional 2-chloromethylmethyl ether (2.5 g) was added and the mixture was heated at 40° C. for 4 hours The reaction mixture was cooled, poured into water (1 L) and the precipitate which formed was collected by filtration and washed with water, then hexane. The solid was recrystallized from hot ethanol to afford 26.8 g (85%) of 2-(2-methoxyethyl)-4-(4-chlorophenyl)-1-(2H)-phthalazinone, m.p. 116.5°-117.5° C.

EXAMPLE 374

2-Methyl-4-(4-isopropylphenyl)-1-(2H)-phthalazinone (Formula VIII: $R^2=Me$; $R^5=$4-iPr-Ph; $R^6=H$)

Methyl hydrazine (8.05 g, 0.175 mol) was added to a mixture of 2-(4-isopropylbenzoyl)benzoic acid (40.2 g, 0.15 mol) in toluene (350 mL) and the mixture was heated to reflux for 3 hours with the removal of water with a Dean Stark trap. The reaction mixture was hot filtered through celite, the filtrate was concentrated to 125 mL and the filtrate was diluted with hexane (100 mL) and cooled. A solid was collected by filtration to afford 27.97 g (67%) of 2-methyl-4-(4-isopropylphenyl)-1-(2H)-phthalazinone, m.p. 107°-107.5° C.

EXAMPLE 378

(a)

4,5-Dihydro-4-methyl-1-phenyl-3-[1-(4-nitrophenyl)methyl]-1H-2,4-benzodiazepine fumarate (Formula I: $R^1=R^4=R^6=H$; $R^2=Me$; $R^3=$

$R^5=Ph$)

Anhydrous sodium acetate (2.62 g, 32 mmol) was added to a mixture of 2-(N-methylaminomethyl)-α-phenylbenzenemethanamine of Example 132 (4.78 g, 16 mmol), the imino ester hydrochloride of formula PhCH₂C(NH)OCH₃.HCl (11.06 g, 48 mmol) and methanol (80 mL) and the mixture was stirred at room temperature for 64 hours. The reaction mixture was filtered, the filtrate was concentrated in vacuo, and the residue was dissolved in methanol and diluted with ether. The solvent was decanted, the residue was washed with additional ether, and then was treated with $CH_2Cl_2$ and a water/saturated $Na_2CO_3$ solution. The layers were separated, the aqueous layer was extracted with $CH_2Cl_2$ and the combined organic layers were washed with water containing saturated $Na_3CO_3$ (3 drops), dried over $Na_2SO_4$ and concentrated in vacuo. The residue was purified by column chromatography on silica eluting with 3% isopropylamine/$CH_2Cl_2$ to afford an oil which was crystallized by the addition of ether. The solid product was dissolved in ethanol, treated with fumaric acid (2.4 g) and diluted with ether to afford the fumarate salt which was collected by filtration. The fumarate salt was recrystallized from methanol/ether to afford 2.78 g (36%) of 4,5-dihydro-4-methyl-1-phenyl-3-[1-(4-nitrophenyl)methyl]-1H-2,4-benzodiazepine fumarate, m.p. 205.5°–207° C.

(b)

4,5-Dihydro-4-methyl-1-phenyl-2-[1-(4-aminophenyl)methyl]-1H-2,4-benzodiazepine dihydrochloride (Formula I: $R^1=R^4=R^6=H$; $R^2=Me$; $R^3=$

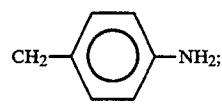

$R^5=Ph$)

To a solution of the 2,4-benzodiazepine of Example 378(a) (0.49 g, 1 mmol) in methanol (50 mL) was added 10% Pd/C (0.07 g) and the mixture was hydrogenated on a Parr hydrogenator at 54 psi for 25 minutes. The catalyst was removed by filtration through solka floc and the filtrate was concentrated in vacuo and the residue was combined with the crude product obtained from a similar experimental run starting with 1.8 g of the 2,4-benzodiazepine of Example 378(a). The combined residue was dissolved in $CH_2Cl_2$, basified with saturated $Na_2CO_3$ and the layers were separated. The aqueous phase was extracted with $CH_2Cl_2$ and the organic layers were combined, dried over $Na_2SO_4$ and acidified with ethereal HCl. The solvent was removed in vacuo and the residue was recrystallized from methanol/ether to afford 1.49 g (76%) of 4,5-dihydro-4-methyl-1-phenyl-3-[1-(4-aminophenyl)methyl]-1H-2,4-benzodiazepine dihydrochloride.

(c)

4,5-Dihydro-4-methyl-1-phenyl-3-[1-(4-methylsulfonylaminophenyl)methyl]-1H-2,4-benzodiazepine (Formula I: $R^1=R^4=R^6=H$; $R^2=Me$; $R^3=$

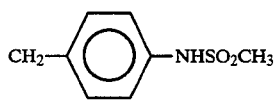

$R^5=Ph$)

To a cooled mixture of the diamine dihydrochloride of Example 378 (b) (1.16 g, 28 mmol), $CH_2Cl_2$ (25 mL) and pyridine (6 mL) under nitrogen was added methanesulfonyl chloride (0.64 g, 56 mmol). The reaction mixture was stirred, with cooling in ice-bath, for 1¾ hours and then was poured into a solution of water/saturated $Na_2CO_3$. The layers were separated, the aqueous layer was extracted with $CH_2Cl_2$, and the organic layers were combined and washed with water/saturated $Na_2CO_3$. The organic layer was dried over $Na_2SO_4$, the solvent was removed in vacuo, and the residue was diluted with hexane. A precipitate formed which was slurried with t-BuOMe and collected by filtration. The solid was recrystallized from hot $CH_2Cl_2$/hexane to afford 0.85 g (73%) of 4,5-dihydro-4-methyl-1-phenyl-3-[1-(4-methylsulfonylaminophenyl)-methyl]-1H-2,4-benzodiazepine as an off-white solid, m.p. 182°–185° C.

EXAMPLE 379

4,5-Dihydro-4-methyl-1-phenyl-3-[2-(2-methylsulfonylaminophenyl)ethyl]-1H-2,4-benzodiazepine hydrochloride (Formula I: $R^1=R^4=R^6=H$; $R^2=Me$; $R^3=$

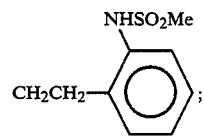

$R^5=Ph$)

To a mixture of 4,5-dihydro-4-methyl-1-phenyl-3-[2-(2-aminophenyl)ethyl-1H-2,4-benzodiazepine dihydrochloride of Example 253 (3.7 g, 8.6 mmol), $CH_2Cl_2$ (65 mL), and pyridine (17 mL, 0.21 mol) at 0° C. under nitrogen was added methanesulfonyl chloride (1.67 g, 14.6 mol) in $CH_2Cl_2$ (2.0 mL). The mixture was stirred as such for 2 hours, diluted with water (100 mL) and basified with a saturated $Na_2CO_3$ solution. The layers were separated, the aqueous layer was extracted with $CH_2Cl_2$ and the combined organic extracts were washed with water containing 1 mL of saturated $Na_2CO_3$. The solvent was dried over $Na_3SO_4$, and concentrated in vacuo to afford a residual oil. The oil was crystallized from t-BuOMe (50 mL) and hexane (100 mL) and the crystalline product was recrystallized from $CH_2Cl_2$ (10 mL)/t-BuOMe (10 mL)/hexane (40 mL) to afford 3.34 g (90%) of the product as the free base, m.p. 208°–212° C. The free base was slurried with methanol (20 mL), acidified with ethereal HCl, and diluted with ether to afford a precipitate which was collected by filtration to afford 3.62 g (90%) of 4,5-dihydro-4-methyl-1-phenyl-3-[2-(2-methylsulfonylaminophenyl)ethyl]-1H-2,4-benzodiazepine hydrochloride as a white solid, m.p. 245°–246° C.

EXAMPLE 380

Methyl 3-(2-pyridyl)propionate (Formula: $R^3COOR^{12}$; $R^3=$

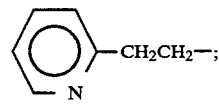

$R^{12}=Me$)

To a solution of methyl triphenylphosphoranylidene acetate (31.2 g) in $CH_2Cl_2$ (120 mL) was added dropwise over 15 minutes 2-pyridine carboxaldehyde (8.9 mL, 0.093 mol) in CH₂Cl₂ (40 mL). The mixture was heated to reflux for 8 hours, additional ylide (3.1 g) was added and the mixture was refluxed overnight. The reaction mixture was cooled, concentrated to ½ value and allowed to stand for 2 hours. A solid was collected by filtration and was washed with CH₂Cl₂/hexane. The filtrate was concentrated in vacuo and the residue was vacuum distilled at 80°–107° C. and 1.5 mm Hg to afford 12.2 g (80%) of methyl 3-(2-pyridyl)-2-propenoate.

A mixture of the latter (12.2 g), ethanol (150 mL) and 10% Pd/C (1.22 g) was hydrogenated on a Parr hydrogenator for about 15 hours, the catalyst was removed by filtration and the filtrate was concentrated in vacuo to afford 12.26 g of methyl 3-(2-pyridyl) propionate.

EXAMPLE 382

Methyl-3-(3-pyridyl)propionate (Formula $R^3CO_2R^{12}$; $R^3=$

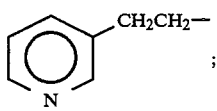

$R^{12}=Me$)

A mixture of 3-bromopyridine (4.82 mL, 0.05 mol), palladium acetate (0.22 g, 0.02 equiv.), tri-(o-tolyl)phosphine (0.61 g, 0.04 equiv.), methyl acrylate (9.01 mL, 2 equiv.), triethylamine (12.5 mL) and CH₃CN (25 mL) was sealed in a bomb and heated to 100° C. for 3.5 hours. The mixture was cooled in an ice-bath, the bomb was vented and the reaction mixture was concentrated in vacuo. The residue was extracted with 0.5N HCl/Et₂O (3×), the organic layer was backwashed with additional 0.5N HCl and the aqueous layers were combined, basified with saturated NaHCO₃ and extracted with ether. The ether layer was washed with brine, dried over Na₂SO₄ and concentrated in vacuo to afford 7.89 g (97%) of methyl 3-(3-pyridyl)-2-propenoate.

A mixture of the latter (9.34 g, 0.057 mol), ethanol (100 mL) and 10% Pd/C was hydrogenated on a Parr hydrogenator for 3 hours. The catalyst was removed by filtration and the filtrate was concentrated in vacuo to afford 8.75 g (93%) of methyl 3-(3-pyridyl)propionate.

EXAMPLE 384

(a)

4,5-Dihydro-4-methyl-1-(4-methoxyphenyl)-3-[2-(4-nitrophenyl)ethyl]-1H-2,4-benzodiazepine hydrochloride (Formula I: $R^1=R^4=R^6=H$; $R^2=Me$; $R^3=$

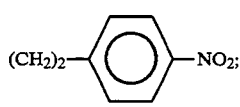

$R^5=Ph$)

A mixture of the diamine dihydrochloride of Example 126C (7.15 g, 0.022 mol), the ortho ester of the formula (MeO)₃C-(CH₂)₂-4-NO₂-Ph (15 g), sodium acetate (4.3 g) and isopropyl acetate (150 mL) was refluxed for 2.5 hours. The mixture was filtered while hot, and the filtrate was extracted with 2N NaOH/CH₂Cl₂. The mixture was filtered through solka floc, the pad was washed with brine, 2N NaOH and water. The filtrate was dried over Na₂SO₄ and concentrated in vacuo. The residue was recrystallized from methanol/ether to afford 4.7 g of the free base which was converted into the hydrochloride salt for use in the next step.

(b)

4,5-Dihydro-4-methyl-1-(4-methoxyphenyl)-3-[2-(4-aminophenyl)ethyl]1H-2,4-benzodiazepine dihydrochloride (Formula I: $R^1=R^4=R^6=H$; $R^2=Me$; $R^3=$

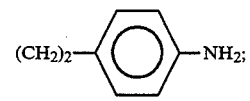

$R^5=Ph$)

A mixture of the benzodiazepine of Example 384 (a) (4.5 g, 0.01 mol), ethanol (120 mL) and 10% Pd/C was hydrogenated in a Parr hydrogenator for 1.5 hours. The catalyst was removed by filtration and the filtrate was concentrated in vacuo. The residue was converted into the dihydrochloride salt, and the salt was recrystallized from EtOH/CH₃CN/Et₂O then MeOH/CH₃CN/Et₂O. The mother liquor was concentrated in vacuo, the residue converted back into the free base, and the free base was purified by column chromatography on silica eluting with t-BuOMe/2–4% isopropylamine. The residue was converted into the dihydrochloride salt and the salt was combined with that obtained above to afford 4.82 g (54%) of 4,5-dihydro-1-(4-methoxyphenyl)-3-[2-(4-aminophenyl)ethyl]-1H-2,4-benzodiazepine dihydrochloride.

(c)

4,5-Dihydro-4-methyl-1-(4-methoxyphenyl)-3-[2-(4-methylsulfonylaminophenyl)ethyl]-1H-2,4-benzodiazepine hydrochloride (Formula I: $R^1=R^4=R^6=H$; $R^2=Me$; $R^3=$

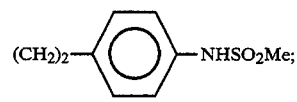

$R^5=Ph$)

To an ice-cooled solution of the amine of Example 384 (b) (3.33 g, 7.3 mmol) in CH₂Cl₂ (35 mL) was added pyridine (17 mL), followed by methanesulfonyl chloride (0.84 mL) in CH₂Cl₂ (10 mL). The mixture was warmed to room temperature, stirred for 1.5 hours, and poured into saturated K₂CO₃ (50 mL). The organic layer was separated and the precipitate which formed over 2 hours was collected by filtration. The solid was converted into the fumarate salt, which was purified by column chromatography on neutral alumina eluting with 5–6% methanol in CH₂Cl₂. The purified salt was then converted back into the free base and then into the hydrochloride salt to afford 1.224 g of 4,5-dihydro-4-methyl-1-(4-methoxyphenyl)-3-[2-(4-methylsulfonylaminophenyl)ethyl]-1H-2,4-benzodiazepine hydrochloride as a light yellow powder, m.p. 149° C. (dec.).

EXAMPLE 386

2-Methyl-4-(3,4-dichlorophenyl)-1-(2H)-phthalazinone (Formula VIII: $R^2$=Me, $R^5$=3,4-$(Cl)_2$-Ph; $R^6$=H)

To a solution of 2-(3,4-dichlorobenzoyl)benzoic acid (29.4 g, 0.1 mol) in toluene (100 mL) was added methyl hydrazine (5.8 mL). The mixture was brought to reflux for 3 hours, with the removal of water via a Dean Stark trap. The mixture was cooled, and the product was collected by filtration to afford 25.54 g (84%) of 2-Methyl-4-(3,4-dichlorophenyl)-1-(2H)-phthalazinone, m.p. 179°–181° C.

EXAMPLE 389

2-Methyl-4-(3-methylsulfonylamino-4-chlorophenyl)-1-(2H)-phthalazinone (Formula VIII: $R^2$=Me; $R^5$=3-$CH_3SO_2NH$-4-Cl-Ph; $R^6$=H)

To a mixture of 2-methyl-4-(3-amino-4-chlorophenyl)-1-(2H)-phthalazinone (38.72 g, 0,136 mol), $CH_2Cl_2$ (380 mL) and pyridine (75 mL) at 0° C. was added methanesulfonyl chloride (15.75 mL) in $CH_2Cl_2$ (75 mL). The reaction mixture was stirred overnight, poured into 1N HCl (400 mL) and stirred for 45 minutes. The mixture was filtered and the filtrate layers were separated. The solid thus obtained was treated with saturated $NaHCO_3$, filtered, stirred with hexane, then filtered, stirred with hot methanol, then filtered and finally stirred with hot ethyl acetate and filtered to afford 38.8 g (78%) of 2-methyl-4-(3-methylsulfonylamino-4-chlorophenyl)-1-(2H)-phthalazinone, m.p. 234°–236° C.

EXAMPLE 394

Methyl 3-(4-pyridyl)propionate (Formula $R^3CO_2R^{12}$: $R^3$=

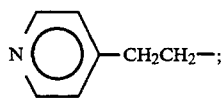

$R^{12}$=Me)

A mixture of 4-bromopyridine (40.6 g, 0.25 mmol), palladium acetate (1.16 g, 5.14 mmol), tri-(O-tolyl)phosphine (3.14 g, 10.3 mmol), $CH_3CN$ (129 mL), triethylamine (64.3 mL, 0.46 mmol) and methyl acrylate (46.8 mL, 0,514 mmol) was sealed in a bomb and placed in an oil bath at 120° C. for 4 hours. The mixture was cooled to 0° C., the bomb was vented, and the slurry thus obtained was partitioned between $CH_2Cl_2$/water. The aqueous phase was separated, extracted with $CH_2Cl_2$ (2×200 mL) and the combined organic layers were dried over $MgSO_4$. The solvent was removed in vacuo to afford 38 g of methyl 3-(4-pyridyl)propenoate.

To a solution of the latter (10.07 g, 0.06 mol) in ethanol (200 mL) was added 10% Pd/C (1.1 g). The mixture was hydrogenated on a Parr hydrogenator for 2 hours, then the catalyst was removed by filtration and the filtrate was concentrated in vacuo to afford 10.09 g (100%) of methyl 3-(4-pyridyl)propionate.

EXAMPLE 400

1-Methyl-4-(2,4-dichlorophenyl)-1-(2H)-phthalazinone

Formula VIII: $R^2$=Me; $R^5$=2,4-$(Cl)_2$-Ph; $R^6$=H)

A mixture of 2-(2,4-dichlorobenzoyl) benzoic acid (31.37 g, 0.106 mol), toluene (100 mL) and methyl hydrazine (6.2 mL) was refluxed for 3 hours with the removal of water via a Dean Stark trap. The mixture was cooled, and the product was collected by filtration and dried to afford 20.74 g of 1-methyl-4-(2,4-dichlorophenyl)-1-(2H)-phthalazinone as an off-white powder, m.p. 145°–146° C.

EXAMPLE 404

2-Methyl-4-(3-chloro-4-methoxyphenyl)-1-(2H)-phthalazinone (Formula VIII: $R^2$=Me; $R^5$=3-Cl-4-$CH_3O$-Ph; $R^6$=H)

A mixture of 2-(3-chloro-4-methoxybenzoyl)benzoic acid (10.46 g, 0,036 mol), toluene (50 mL) and methyl hydrazine (2.1 mL) was refluxed in the presence of a Dean Stark trap until the theoretical amount of water had been collected. The reaction mixture was cooled, and the product was collected by filtration to afford 7.42 g (68.7%) of 2-methyl-4-(3-chloro-4-methoxyphenyl)-1-(2H)-phthalazinone, m.p. 195°–195° C. An additional 1.89 g of product was also collected from the filtrate for a total of 9.31 g (86.2%).

EXAMPLE 407

2-Methyl-4-(4-methylphenyl)-1-(2H)-phthalazinone (Formula VIII: $R^2$=Me; $R^5$=4-$CH_3$-Ph; $R^6$=H)

Following a procedure similar to that described above for Example 404, there was prepared 25.78 g (82.4%) of 2-methyl-4-(4-methylphenyl)-1-(2H)-phthalazinone, m.p. 150°–152° C., from 2-(p-tolyl)benzoic acid (30.0 g, 0.125 mol), toluene (100 mL) and methyl hydrazine (7.3 mL).

EXAMPLE 411

2-(2,4-diethylbenzoyl) benzoic acid (Formula XIII: $R^5$=2,4-$(Et)_2$-Ph; $R^6$=H)

To a cooled mixture of phthalic anhydride (50 g, 0.34 mol) and aluminum chloride (99 g) in tetrachloroethane (300 mL) was added dropwise 1,3-diethylbenzene (50 g) over 1¼ hours. The mixture was stirred in an ice bath for 30 minutes, additional tetrachloroethane was added, and the mixture was stirred for 2 hours. The reaction mixture was poured into concentrated HCl/ice (1 L), ether (500 mL) was added and the mixture was filtered. The organic layer was separated, washed with saturated $Na_2CO_3$ (6×), the basic layer was extracted with $CH_2Cl_2$ and the $CH_2Cl_2$ layer was extracted with 2N NaOH and the 2N NaOH layer was acidified. The basic layer was acidified with aqueous HCl, this acidic layer was combined with the above acidified 2N NaOH layer and the mixture was extracted with ether. The $CH_2Cl_2$ layer and the ether layer were combined and concentrated in vacuo. The residue was slurried with water, filtered and rinsed with hexane to afford 88.8 g (93%) of 2-(2,4-diethylbenzoyl)benzoic acid, m.p. 115°–118° C.

EXAMPLE 412

2-Methyl-4-(2,4-diethylphenyl)-1-(2H)-phthalazinone (Formula VIII: $R^2$=Me; $R^5$=2,4-$(Et)_2$-Ph; $R^6$=H)

A mixture of 2-(2,4-diethylbenzoyl)benzoic acid (40 g, 0.14 mol), toluene (120 mL) and methyl hydrazine (7.5 mL) were refluxed for 3 hours with removal of water via a Dean Stark trap. Additional toluene (100 mL) and methyl hydrazine (4.0 mL) were added and the mixture was refluxed until 2.8 mL of water was collected. The mixture was cooled, extracted with CH$_2$Cl$_2$/2N NaOH, then 1N HCl and the organic layer was separated, dried over Na$_2$SO$_4$ and concentrated in vacuo. The residue was crystallized from ethanol/water and recrystallized from ethanol/water to afford 22.86 g (55.9%) of 2-methyl-4-(2,4-diethylphenyl)-1-(2H)-phthalazinone, m.p. 94.5°–96.5 ° C.

EXAMPLE 416

4,5-Dihydro-1-(4-hydroxyphenyl)-4-methyl-3-[2-(4-pyridyl)ethyl]-1H-2,4-benzodiazepine dihydrochloride (Formula I: R$^1$=R$^4$=R$^6$=H; R$^2$=Me; R$^3$=

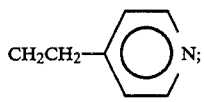

R$^5$=4-HO-Ph)

To a mixture of 4,5-dihydro-1-(4-methoxyphenyl)-4-methyl-3-[2-(4-pyridyl)ethyl]-1H-2,4-benzodiazepine dihydrochloride (3.81 g, 8.6 mmol, prepared from the fumarate of Example 398 by standard procedures) in CH$_2$Cl$_2$ (40 mL) in an ice-bath under N$_2$ was added boron tribromide (17.2 mL, 1M in CH$_2$Cl$_2$). The mixture was stirred for 3 hours, 2N HCl was added and the mixture was stirred for ½ hour. The layers were separated, the aqueous layer was extracted with CH$_2$Cl$_2$ and the combined organic layers were washed with 2N HCl. The organic layer was treated with saturated Na$_2$CO$_3$ and the product which precipitates was collected by filtration to afford 3.06 g (83%) of 4,5-dihydro-1-(4-hydroxyphenyl)-4-methyl-3-[2-(4-pyridyl)ethyl]-1H-2,4-benzodiazepine dihydrochloride, m.p. 258°–259° C. after recrystallization from methanol/ether.

EXAMPLE 417

4,5-Dihydro-1-phenyl-2-methyl-3-[4-methylsulfonylaminophenyl]-1H-2,4-benzodiazepine.ethanol (Formula I: R$^4$=R$^5$=R$^6$=H; R$^1$=Ph; R$^2$=Me; R$^3$=

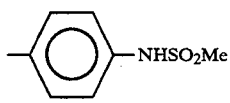

)

Following a procedure similar to that described in General Method F2, but refluxing the material for 6 hours rather than for 50 minutes to 2.5 hours, there was obtained 3.863 g (57.8%) of 4,5-dihydro-1-phenyl-2-methyl-3-[4-methylsulfonylaminophenyl ]-1H-2,4-benzodiazepine.ethanol, m.p. 123.5°–126° C. after recrystallization for ethanol/ether then ethanol; from 2-aminomethyl-N-methyl-α-phenylbenzenemethanamine of Example 175 (5.0 g, 0.0167 mol), trimethyl aluminum (29.24 mL, 0.05848 mol), sulfolane (50 mL) and N-[4-(ethoxycarbonyl)phenyl]methanesulfonamide (4.27 g, 0.01754 mol).

EXAMPLE 418

4,5-Dihydro-1-(4-methylsulfonylaminophenyl)-4-methyl-3-[2-(4-methylsulfonylaminophenyl)ethyl]-1H-2,4-benzodiazepine hydrochloride (Formula I: R$^1$=R$^4$=R$^6$=H; R$^2$=Me; R$^3$=

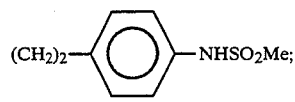

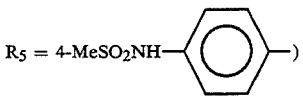

To a solution of the diamine dihydrochloride of Example 362 (1.96 g, 5.00 mmol) in sulfolane (30 mL) at room temperature was added 2M trimethylaluminum (8.74 mL, 17.5 mmol) over 10 minutes. The mixture was stirred for 30 minutes then N-[4-(2-(ethoxycarbonyl)ethyl)phenyl]methanesulfonamide of Example 326 (1.42 g, 5.25 mmol) was added. The mixture was heated to 100°–120° C. for 2 hours, cooled to room temperature and quenched with a Rochelle salt solution (50 mL). CH$_2$Cl$_2$ (100 mL) and water (50 mL) were added, followed by a half saturated solution of Na$_2$CO$_3$ (25 mL) and then additional CH$_2$Cl$_2$ (100 mL). The organic layer was separated, and the aqueous layer was acidified with 2N HCl, filtered and then extracted with CH$_2$Cl$_2$. The combined organic layers were dried over Na$_2$SO$_4$ and concentrated in vacuo. The residue was azeotroped with ethanol, the solvent was removed in vacuo. The residue was purified by column chromatography on silica eluting with CHCl$_3$/iPrOH/CF$_3$CO$_2$H (67/30/3) then CHCl$_3$/EtOH/CF$_3$CO$_2$H (67/30/3) to afford the product as the CF$_3$CO$_2$H salt. The CF$_3$CO$_2$$^H$ salt was treated with ethanolic HCl and the HCl salt thus obtained was recrystallized from hot ethanol to afford 1.07 g (41%) of 4,5-dihydro-1-(4-methylsulfonylaminophenyl)-4-methyl-3-[2-(4-methylsulfonylaminophenyl)ethyl]-1H-2,4-benzodiazepine hydrochloride, m.p. 274°–275° C.

EXAMPLE 419

(a)

2-Methyl-4-phenyl-8-amino-1-(2H)-phthalazinone hydrochloride (Formula VIII: R$^2$=Me; R$^5$=Ph; R$^6$=8-NH$_2$)

A mixture of 2-benzoyl-6-aminobenzoic acid (5.4 g, 22.4 mmol), methyl hydrazine (2.30 g, 50 mmol), ethanol (50 mL) and toluene (25 mL) was heated at 70° C. for 2 hours and then at reflux for 22 hours with removal of water via a Dean Stark trap. Additional methyl hydrazine (0.6 g) was added and the mixture was refluxed for 5 hours. The solvent was removed in vacuo, the residue was dissolved in CH$_2$Cl$_2$, additional crude product (0.4 g) was added from a similar experimental run, and the mixture was diluted with water and 2N NaOH. The aqueous layer was separated, and extracted with CH$_2$Cl$_2$, and the combined organic layers were washed with water containing 2N NaOH (1 mL), dried over Na$_2$SO$_4$ and concentrated in vacuo. The residue was treated with ethanolic HCl and the mixture was diluted with ether to afford the HCl salt which was collected by filtration and dried at 85° C. in vacuo to afford 5.40 g (79%) of 2-methyl-4-phenyl-8-amino-1-(2H)-phthalazinone hydrochloride, m.p. 199°–213° C.

(b)

2-Methyl-4-phenyl-8-methylsulfonylamino-1-(2H)-phthalazinone (Formula VIII: $R^2$=Me; $R^5$=Ph; $R^6$=8-NHSO$_2$Me)

A mixture of the phthalazinone of Example 419(a) (5.2 g, 17 mmol) CH$_2$Cl$_2$ (90 mL), and pyridine (23 mL) was cooled in an ice-bath and treated with methanesulfonyl chloride (6.18 g, 54 mmol) in CH$_2$Cl$_2$ (5 mL). The mixture was warmed to room temperature over 1.5 hours and then was stirred for 4 hours. The solvent was removed in vacuo, the residue was diluted with water (60 mL) and concentrated HCl (15 mL). The mixture was filtered, and the collected precipitate was slurried with water and saturated Na$_2$CO$_3$ (5 mL), and this mixture was filtered and washed with water. The product was then slurried with acetone/hexane (1/1, 40 mL) and collected by filtration to afford 5.73 g (100%) of 2-methyl-4-phenyl-8-methylsulfonylamino-1-(2H)-phthalazinone, m.p. 217°–218° C.

EXAMPLE 421

4,5-Dihydro-1-phenyl-3-[2-phenylethyl]-2-methyl-6-methylsulfonylamino-1H-2,4-benzodiazepine hydrochloride (Formula I: $R^1$=$R^4$=H; $R^2$=Me; $R^3$=(CH$_2$)$_2$Ph; $R^5$=Ph; $R^6$=6-CH$_3$SO$_2$NH)

A mixture of 2-(N-methylaminoethyl)-3-methylsulfonylamino-α-phenylbenzenemethanamine of Example 420 (0.70 g, 2.6 mmol), the ortho ester of formula Ph (CH$_2$)$_2$C (OMe) 3 (2.18 g, 10.4 mol), methanol (8 mL), acetic acid (0.62 g, 10.4 mol) and methanolic HCl (2 drops) was stirred at room temperature for 1 day, then additional methanolic HCl (2 drops) was added and the mixture was stirred for 24 hours. Additional methanolic HCl was added and the reaction was stirred for another four days. The reaction mixture was acidified with methanolic HCl, diluted with ether, and cooled in an ice-bath and the precipitate thus obtained was collected by filtration and washed with methanol/ether to afford 0.75 g (68%) of 4,5-dihydro-1-phenyl-3-[2-phenylethyl]-2-methyl-6-methylsulfonylamino-1H-2,4-benzodiazepine hydrochloride, m.p. 270°–270.5° C.

BIOLOGICAL TEST RESULTS

The compounds of this invention having formulas XXXVI, XXX, III, II and XXXVII have antiarrhythmic activity as shown by the results of standard pharmacological tests carried out on representative examples as described below.

Antiarrhythmic activity was demonstrated by a procedure, which is a modification of standard programmed electrophysiological techniques utilized in large animals and in clinical studies in humans. Male Duncan-Hartley guinea pigs (600–800 grams) were anesthetized with sodium pentobarbital (30 mg/kg, i.p.) and artificially ventilated with a Harvard small-animal respirator. A left thoracotomy was performed and a fluid-filled catheter and transducer (Millar Micro-tip, Model 4F, Millar Inst. Inc., Houston, Tex.) were inserted through the anterior wall of the left ventricle to monitor left ventricular pressure (LVP). The first derivative of the LVP (dP/dt) was obtained from a Grass differentiator (Model 7P20B) and used as an index of contractile function. A lead II EKG along with LVP and dP/dt were continuously recorded on a Grass polygraph (Model 7B). Rate pressure product (RPP), an index of cardiac work, was calculated using peak systolic LVP and heart rate (HR).

Effective refractory periods (ERP) were evaluated during left ventricular pacing. Grass subcutaneous electrodes were implanted as bipolar ventricular electrodes to deliver stimuli from a Bloom DTU-2 stimulator (Bloom Electronics, Inc., Reading, Pennsylvania) and stimulus isolation unit. Hearts were stimulated at the slowest frequency allowing consistent pacing (S1, 240–300 bpm) using 2 ms pulses at twice diastolic threshold. Threshold was determined by increasing the stimulation voltage until a 1:1 capture of the ventricular response with the stimulus was observed. A train of 8 normal pulses was delivered followed by a premature (S2) pulse. The interval between the last S1 and the premature S2 pulse was reduced in 10-ms increments until a ventricular response was not initiated. The longest S1-S2 interval that failed to produce a ventricular response was defined as the ERP. Pacing stimuli and the EKG were displayed at a sampling frequency of 92 Hz on an Apple IIe microcomputer using a two-channel 8-bit A/D converter (R.C. Electronics, Compu-Scope APL-D2, Santa Barbara, Calif.).

Baseline hemodynamic function was evaluated followed by ventricular pacing to determine ERP. Pacing was discontinued prior to drug administration and resumed at set intervals during the protocol to evaluate ERP. Test compounds were administered (1 mL/kg) via the left ventricular catheter over a 15-second interval for doses less than 10 mg/kg. Higher doses (>10 mg/kg) were slowly infused over a 1-minute interval. Doses were cumulatively increased every 15 minutes until a maximally tolerated dose which reduced dP/dt by 50% was noted. Ten minutes after each dose, hemodynamics and ERP were reevaluated.

Data were analyzed using an analysis of variance for repeated measures of raw data and are expressed as means. An effective dose to increase ERP by a minimum of 20 msecs (ED$_{20}$), which was consistently a statistically significant increase, was derived for each animal from a linear regression of the data and expressed as a mean for the treated population. Biological significance was established at a probability of error less than 0.05. The results are presented in Table N.

TABLE N

| EXAMPLE | ED$_{20}$ (mg/kg) |
| --- | --- |
| 1 | 0.31 |
| 2 | 1.17 |
| 4 | 0.20 |
| 5 | 1.0–1.2 |
| 7 | 0.72–0.91 |
| 8 | 0.4–2.5 |
| 8B | 0.32–0.42 |
| 8C | 0.31 |
| 8D | 0.16 |
| 8E | 0.93 |
| 9 | 0.50 |
| 10 | 0.44 |
| 11 | 0.14–0.39 |
| 12 | 0.08 |
| 13 | 0.14 |
| 14 | 0.13 |
| 16 | 0.53 |
| 17 | 0.52–1.29 |
| 18 | 0.25–0.44 |
| 19 | 0.57 |
| 20 | 0.40 |
| 21 | 0.35 |
| 22 | 0.23 |
| 23 | 0.21 |
| 24 | 0.15 |
| 25 | 0.04–0.2 |

TABLE N-continued

| EXAMPLE | ED$_{20}$ (mg/kg) |
|---|---|
| 26 | 1.97 |
| 27 | 0.99 |
| 28 | 0.65 |
| 29 | 0.43 |
| 30 | 0.28 |
| 31 | 4.40 |
| 32 | 0.28 |
| 34 | 0.17 |
| 35 | 0.11 |
| 37 | 1.27 |
| 39 | 0.22 |
| 40 | 0.10 |
| 41 | 0.35 |
| 42 | 0.34 |
| 43 | 0.17 |
| 44 | 0.24 |
| 45 | 0.60 |
| 46 | 0.60 |
| 47 | 0.41 |
| 48 | 2.20 |
| 49 | 1.36 |
| 50 | 0.50 |
| 51 | 0.52 |
| 52 | 0.18 |
| 53 | 0.15 |
| 54 | 0.23 |
| 55 | 0.25 |
| 56 | 0.09 |
| 57 | 0.14 |
| 58 | 0.10 |
| 59 | 0.02–0.1 |
| 60 | 0.13 |
| 61 | 0.05 |
| 62 | 1.4–1.74 |
| 63 | 0.20 |
| 64 | 0.39–1.2 |
| 65 | 0.48–0.95 |
| 66 | 0.40 |
| 67 | 0.2–0.4 |
| 68 | NE* |
| 69 | 0.54 |
| 70 | 0.71 |
| 72 | 0.57 |
| 74 | 0.43 |
| 75 | 0.41 |
| 76 | 0.42 |
| 77 | 0.25 |
| 78 | 0.15 |
| 80 | 0.04 |
| 81 | 0.41 |
| 82 | 0.29 |
| 84 | 0.39 |
| 85 | 0.93 |
| 86 | 0.28 |
| 87 | NE* |
| 88 | 0.08 |
| 89 | 0.08 |
| 90 | 0.47 |
| 91 | 0.35 |
| 92 | 0.22 |
| 93 | 0.28 |
| 94 | 0.56 |
| 95 | 0.16–0.66 |
| 96 | 0.76–0.83 |
| 97 | 2.49 |
| 98 | 0.42 |
| 99 | 0.80 |
| 100 | 0.57 |
| 101 | 0.32 |
| 102 | 0.04–0.18 |
| 103 | 0.18 |
| 104 | 0.27–1.87 |
| 105 | 0.26 |
| 106 | 0.30 |
| 107 | 0.4–0.81 |
| 108 | 0.16 |
| 109 | 2.40 |
| 112 | 0.38–2.32 |
| 113 | 0.27 |
| 114 | 0.53 |
| 115 | 0.14 |
| 116 | 0.10 |
| 117 | 0.30 |
| 118 | 0.15 |
| 119 | 0.34 |
| 120 | 0.88 |
| 121 | 0.29–0.60 |
| 122 | 0.08 |
| 123 | 0.34 |
| 125 | 29.9 |
| 129 | 2.12 |
| 130 | 0.66 |
| 131 | 0.50 |
| 133 | NE* |
| 134 | 1.00 |
| 143 | 1.40 |
| 149 | 0.23 |
| 150 | 1.10–1.18 |
| 151 | 1.70 |
| 153 | 0.70 |
| 155 | 0.18 |
| 156 | 2.00 |
| 157 | 1.7–3.2 |
| 159 | 4.39 |
| 160 | NE* |
| 161 | 0.38–1.94 |
| 162 | 0.80 |
| 163 | 0.15 |
| 164 | 0.12–0.45 |
| 165 | 0.19 |
| 166 | 0.36 |
| 167 | 0.01–0.05 |
| 168 | 0.02–0.15 |
| 169 | 0.17 |
| 170 | NE* |
| 171 | 0.03–1.0 |
| 176 | 0.81 |
| 177 | 2.63 |
| 179 | 1.66 |
| 180 | 0.18 |
| 181 | 0.84–5.7 |
| 182 | 1.14 |
| 183 | 5.50 |
| 184 | 1.14 |
| 200 | 0.20 |
| 201 | 0.06 |
| 202 | 0.70 |
| 203 | 0.08 |
| 204 | 0.003 |
| 205 | 0.10 |
| 206 | 0.07 |
| 209 | 0.16 |
| 210 | 0.80 |
| 211 | 0.04 |
| 212 | 0.05 |
| 213 | 0.20 |
| 214 | 0.10 |
| 215 | 0.03 |
| 216 | 0.06 |
| 217 | 0.10 |
| 218 | 170.00 |
| 219 | 0.40 |
| 220 | 0.40 |
| 223 | 0.20 |
| 224 | 0.40 |
| 225 | 0.60 |
| 226 | 0.10 |
| 227 | 0.20 |
| 228 | 0.50 |
| 229 | 0.07 |
| 230 | 0.20 |
| 232 | 0.02 |
| 235 | 0.20 |
| 236 | 0.40 |
| 237 | 0.20 |
| 238 | 0.30 |
| 239 | 0.08 |
| 240 | 0.20 |
| 241 | 0.04 |
| 243 | 0.07 |
| 244 | 0.28 |
| 249 | 0.05 |

TABLE N-continued

| EXAMPLE | ED$_{20}$ (mg/kg) |
|---------|-------------------|
| 250 | 0.10 |
| 251 | 0.11 |
| 257 | 1.00 |
| 259 | 0.17 |
| 260 | 0.19 |
| 261 | 0.17 |
| 262 | 0.07 |
| 263 | 0.16 |
| 266 | 0.20 |
| 267 | 0.10 |
| 268 | 0.50 |
| 273 | 434.00 |
| 280 | 0.65 |
| 281 | 0.20 |
| 282 | 15.00 |
| 283 | 0.10 |
| 284 | 1.10 |
| 285 | 0.10 |
| 286 | 0.55 |

The antiarrhythmic activity of representative compounds of the invention was also demonstrated by the following procedure:

Rabbit Langendorff Model:

New Zealand White male rabbits (2.5–3.5 kg, Hazelton Farms, N.Y.) were anesthetized with 35 mg/kg sodium pentobarbital intravenously via an ear vein. Heparin (1000 U) was subsequently injected. A tracheotomy was performed and the animal was intubated and ventilated with room air. A medialsternal thoracotomy was performed. The pericardium was removed and the aorta was dissected free. The inferior vena cava was occluded and the pulmonary vein was severed. The aorta was cannulated and retrograde perfusion (20 mL/min) with 37° C. Krebs solution was begun. The heart was then excised and transferred directly to the Langendorff apparatus and perfused at 30 mL/min. All experimental procedures were performed in accord with the guidelines for the Care and Use of Animals (NIH Publication No. 86-23, 1985), and the Animal Welfare Act (P.L. 89-544, as amended).

A latex balloon (size 12 Hugo Sachs Eletronik Hugstetten, Germany) was inserted into the left ventricle via the left atria. The balloon was connected to a pressure transducer (Gould p23ID, Cleveland, Ohio). The balloon was inflated with Krebs solution until a stable end diastolic pressure of approximately 5 mm Hg was established. The right atrium was removed and the AV node crushed. Bipolar stimulating electrodes (Grass platinum, Quincy, MA) were placed in the free wall of the right ventricle. The heart was stimulated at a base frequency (S1) of 120 stimuli/min with 2 ms constant current pulses at twice threshold with a 1 mA minimum intensity. Stimulation parameters were controlled by a Bloom Associates (Reading, PA) model DTU 215 stimulator with isolation unit. Two other electrodes were placed at the extremes of the ventricular longitudinal axis to monitor the electrocardiogram (Grass model 7P6C preamplifier and polygraph). A pressure transducer (Gould p23ID) was connected, at the level of the heart, to the perfusion line to monitor perfusion pressure.

The Krebs solution was composed of (in mM): 118.0 NaCl, 4.5 KCl, 1.3 mM CaCl$_2$, 1.16 MgSO$_4$, 11 dextrose, 25.0 NaHCO$_3$. The solution was equilibrated with 95% O$_2$ and 5% CO$_2$ and maintained at 37° C.

Measured ventricular function parameters included end diastolic ventricular pressure (EDLVP), systolic ventricular pressure (SLVP), developed pressure (SLVP-EDLVP) and perfusion pressure in mm Hg. The first derivative (dP/dt) of the ventricular pressure was determined electronically. Data was collected by a Buxco Electronics logging analyzer system (LS-14, Sharron, CT). The heart was allowed to equilibrate for 45 minutes prior to determining control (drug free) effective refractory period (ERP). Ventricular function parameters were determined at −15, −10, −5 and −1 min prior to determining ERP. Each concentration of the test agent was perfused for 15 minutes with function parameters recorded every 5 minutes. At the end of each 15 min exposure ERP was determined. Cumulative concentration responses were recorded for 5 concentrations of each test agent.

Effective refractory period was determined by inserting a premature stimuli (S2) into the base frequency of stimulation (S1). The interval between S1 and S2 was reduced by 5 ms until there was no contraction associated with S2. The last interval from S1 to S2 which resulted in a contraction was reported as the ERP. Stimulation intensity was determined for each concentration of test agent. A minimum of 20 S1 stimuli were allowed between ERP interrogation.

A change (delta) in ERP $\geq$20 ms (approx. 20%) or a change in dp/dt (+or −) of a magnitude $\geq$220 mm Hg (approx. 20%) were considered to be physiologically important. A four parameter logistic curve was fit to the ERP and dp/dt concentration response for each heart using Sigmaplot (4.0) software (Jandel Scientific, Corte Madera, Calif.). The concentration (in nM) at which there was a change in ERP of 20 ms (EC$_{20\ ms}$) was determined from the curve. The concentration (in nM) at which there was a change in dp/dt of $\pm$220 mm Hg was determined from the curve and was termed the EC$_{dp/dt}$. A positive (+) number for EC$_{dp/dt}$ (nM) indicates that the compounds are mild positive ionotropes which do not reduce (depress) cardiac function. An entry of NE* for EC$_{dp/dt}$ (nM) indicates that no estimate was obtained as the compound failed to show a concentration related effect on contraction. Compounds which have a positive (+) value or an entry of NE* for EC$_{dp/dt}$ (nM) are thus useful in the treatment of cardiac arrhythmias in patients with impaired ventricular function or congestive heart failure. A negative (−) number for EC$_{dp/dt}$ (nM) indicates that the compounds reduce (depress) cardiac function and, although they are useful as antiarrhythmic agents, their use in the treatment of cardiac arrhythmias in patients with impaired ventricular function or congestive heart failure would be contraindicated.

Data were analyzed using an analysis of variance for repeated measures of raw data relative to time course control experiments and expressed as mean change (delta) from baseline. Biological significance was established at a probability of error less than 0.05.

The following table summarizes the results obtained from the testing of representative compounds of the invention in the Rabbit Langendorff Model.

TABLE O

| Example No. | EC$_{20ms}$ (nM) | EC$_{dp/dt}$ (nM) |
|-------------|------------------|-------------------|
| 61 | 39 | −129 |
| 62 | IA | NE* |
| 72 | 196 | −611 |
| 167 | 61 | −700 |
| 201 | 27 | −582 |
| 232 | IA | NE* |
| 241 | 33 | NE* |

TABLE O-continued

| Example No. | EC$_{20ms}$ (nM) | EC$_{dp/dt}$ (nM) |
|---|---|---|
| 243 | 66 | NE* |
| 257 | 20 | +11900 |
| 258 | insoluble | insoluble |
| 260 | 39 | NE* |
| 261 | insoluble | insoluble |
| 262 | 20 | +420 |
| 263 | 655 | NE* |
| 264 | 10 | NE* |
| 265 | 24 | −369 |
| 269 | 260 | NE* |
| 275 | 179 | NE* |
| 288 | 6 | +43 |
| 288A | 9 | NE* |
| 288B | 5 | +4 |
| 288G | 3.8 | NE* |
| 293 | 2.7 | NE* |
| 293A | 1.5 | +4 |
| 293B | 4.1 | +3 |
| 298 | 4 | +38 |
| 301 | 3 | NE* |
| 302 | 5.5 | NE* |
| 303 | 1 | +8 |
| 303A | 1.9 | +2 |
| 303B | 0.5 | +10 |
| 305 | 4 | NE* |
| 305B | 7.6 | NE* |
| 305D | 6.5 | +18 |
| 312 | 4.2 | NE* |
| 312A | 5.5 | NE* |
| 312B | 5.9 | NE* |
| 312C | 8.2 | NE* |
| 312D | 6.9 | NE* |
| 312E | 7.0 | NE* |
| 329 | 19 | +17 |
| 330 | 136 | NE* |
| 331F | 470 | NE* |
| 333 | 520 | NE* |
| 336 | 2.4 | +1.9 |
| 339 | 7 | NE* |
| 342 | 3 | NE* |
| 343 | 110 | NE* |
| 345 | 6 | NE* |
| 348 | 20 | NE* |
| 351 | 200 | NE* |
| 354 | 100 | NE* |
| 355 | 2 | NE* |
| 358 | 1 | +100 |
| 363 | 780 | NE* |
| 364 | 140 | +270 |
| 368 | 90 | +480 |
| 371 | 7 | +6.9 |
| 372 | 15 | NE* |
| 373 | 29 | NE* |
| 376 | 10 | NE* |
| 377 | 7100 | NE* |
| 378C | 386 | NE* |
| 379 | 500 | NE* |
| 381 | 60 | NE* |
| 383 | 200 | NE* |
| 384C | 212 | NE* |
| 385 | 1000 | NE* |
| 388 | 2 | NE* |
| 391 | 100 | NE* |
| 392 | 170 | NE* |
| 393 | 24 | NE* |
| 395 | 10 | +70 |
| 396 | 3 | NE* |
| 397 | 50 | −31 |
| 398 | 26 | +48 |
| 399 | 2 | +2.7 |
| 402 | 0.8 | NE* |
| 403 | 2 | NE* |
| 406 | 4 | NE* |
| 409 | 30 | NE* |
| 410 | 4 | NE* |
| 414 | 10 | NE* |
| 415 | 16 | NE* |
| 416 | IA | NE* |
| 417 | 1000 | NE* |
| 418 | IA | NE* |
| 421 | IA | NE* |

TABLE O-continued

| Example No. | EC$_{20ms}$ (nM) | EC$_{dp/dt}$ (nM) |
|---|---|---|
| 422 | 20 | +6.5 |

IA = inactive
NE* = No estimate as compound failed to show a concentration related effect on contraction.

The compounds of the invention can be prepared for use by conventional pharmaceutical procedures: that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf.

We claim:

1. A compound of formula:

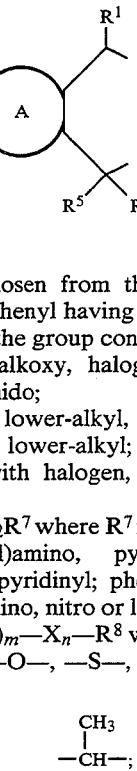

wherein
A is a ring chosen from the group consisting of phenyl, and phenyl having one or two substituents chosen from the group consisting of amino, lower-alkyl, lower-alkoxy, halogen, nitro, and lower-alkylsulfonamido;

$R^1$ is hydrogen, lower-alkyl, or phenyl;

$R^2$ is hydrogen; lower-alkyl; benzyl; phenyl; phenyl substituted with halogen, lower-alkyl or lower-alkoxy; or $R^2$ is —CH$_2$CH$_2$R$^7$ where $R^7$ is lower-alkoxy; benzyl; di(lower-alkyl)amino, pyrrolidino; piperidino; morpholino; pyridinyl; phenyl; or phenyl substituted with amino, nitro or lower-alkylsulfonamido;

$R^3$ is Y$_p$—(CH$_2$)$_m$—X$_n$—R$^8$ wherein

Y is —NH—, —O—, —S—, or $$-\overset{CH_3}{\underset{|}{CH}}-;$$

p is zero or one;
m is an integer from zero to seven;
X is —S—, —O—, —SO$_2$—,

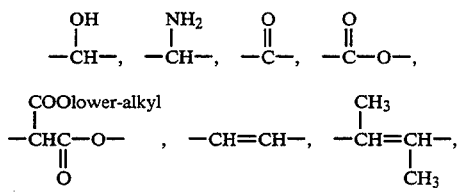

—NHSO$_2$—;

n is zero or one; and

R$^8$ is hydrogen; lower-alkyl; phenyl; furanyl; thienyl, pyridinyl, phenyl having one or two substituents chosen independently from the group consisting of halogen, lower-alkyl, nitro, hydroxy, lower-alkoxy, lower-alkylamido, lower-alkylsulfonamido, polyfluorolower-alkylsulfonamido, lower-alkylaminosulfonyl, di-lower-alkylaminosulfonyl, and amino; or when n is zero and m is other than zero, R$^8$ is additionally halogen; benzyl(lower-alkyl)amino; di-(lower-alkyl)amino; or a 5- or 6-membered heterocycle selected from the group consisting of morpholinyl, piperidinyl, piperazinyl, and imidazolyl, said heterocycle being unsubstituted or substituted with one lower-alkyl group; or X and R$^8$ taken together are cyclohexylidine; or when, m and p are zero, R$^8$ is additionally morpholinyl, piperidinyl, pyrrolidinyl, or di-(lower-alkyl)amino;

R$^4$ is hydrogen; lower-alkyl; allyl; lower-alkoxy-lower-alkyl; acetyl; lower-alkylaceto; lower-alkyl carboxyl; or α-hydroxy-lower-alkyl; and R$^5$ is hydrogen; lower-alkyl; naphthyl; thienyl; pyridinyl; benzyl; phenyl; or phenyl having one or two substituents chosen independently from the group consisting of lower-alkyl, lower-alkoxy, halogen, hydroxyl, amino, di(lower-alkyl)amino, lower-alkylsulfonamido, lower-acylamino, lower-alkylthio, and lower-alkylsulfonyl; or an acid-addition salt thereof;

with the proviso that the total number of carbon atoms in R$^1$ plus R$^2$ plus R$^4$ plus R$^5$ must be five or greater; further provided that when A is phenyl, R$^1$ and R$^2$ are hydrogen or lower-alkyl, and R$^4$ is hydrogen or lower-alkyl, R$^5$ is other than hydrogen or lower-alkyl.

2. A compound according to claim 1 wherein:

R$^2$ is hydrogen; lower-alkyl; benzyl; phenyl; phenyl substituted with halogen, lower-alkyl or lower-alkoxy; or R$^2$ is —CH$_2$CH$_2$R$^7$ where R$^7$ is lower-alkoxy; benzyl; di(lower-alkyl)amino, pyrrolidino; piperidino; morpholino; phenyl; phenyl substituted with amino, nitro or lower-alkylsulfonamido;

R$^3$ is Y$_p$—(CH$_2$)$_m$—X$_n$—R$^8$ wherein

Y is —NH—, —O—, —S—, or

p is zero or one;
m is an integer from zero to seven;
X is —S—, —O—, —SO$_2$—,

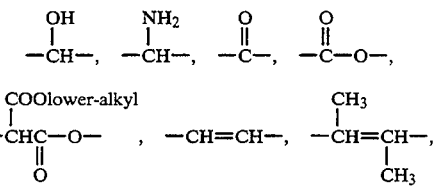

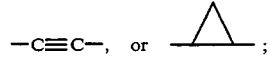

n is zero or one; and

R$^8$ is hydrogen; lower-alkyl; phenyl; furanyl, thienyl, pyridinyl, phenyl having one or two substituents chosen independently from the group consisting of halogen, lower-alkyl, nitro, hydroxy, lower-alkoxy, lower-alkylamido, lower-alkylsulfonamido di-lower-alkylaminosulfonyl, and amino; or when n is zero and m is other than zero, R$^8$ is additionally halogen; benzyl(lower-alkyl)amino; di-(lower-alkyl)amino; or a 5- or 6-membered heterocycle selected from the group consisting of morpholinyl, piperidinyl, piperazinyl, and imidazolyl, said heterocycle being unsubstituted or substituted with one lower-alkyl group; or X and R$^8$ taken together are cyclohexylidine; or when n, m, and p are zero, R$^8$ is additionally morpholinyl, piperidinyl, pyrrolidinyl, or di-(lower-alkyl)amino; and R$^5$ is hydrogen; lower-alkyl; naphthyl; thienyl; pyridinyl; benzyl; phenyl; or phenyl having one or two substituents chosen independently from the group consisting of lower-alkyl, lower-alkoxy, halogen, hydroxyl, amino, di-(lower alkyl)amino, lower-alkylsulfonamido and lower acylamino.

3. A compound according to claim 2 wherein at least one of R$^1$, and R$^5$ is phenyl, naphthyl, thienyl, pyridinyl, benzyl, or phenyl having one or two substituents chosen from the group consisting of lower-alkyl, lower-alkoxy, halogen, hydroxyl, amino, di(lower-alkyl)amino, lower-alkylsulfonamido and lower-acylamino.

4. A compound according to claim 3 wherein both R$^4$ and R$^5$ are other than hydrogen.

5. A compound according to claim 4 wherein R$^1$ is hydrogen, R$^2$ and R$^4$ are methyl and R$^5$ is phenyl or phenyl having one or two substituents chosen from the group consisting of lower-alkyl, lower-alkoxy, halogen, hydroxyl, amino, di(lower-alkyl)amino, lower-alkylsulfonamido and lower-acylamino.

6. A compound according to claim 2 wherein R$^4$ and R$^5$ are both hydrogen and R$^1$ is phenyl.

7. A compound according to claim 2 wherein R$^1$ and R$^4$ are both hydrogen.

8. A compound according to claim 7 wherein R$^2$ is lower-alkyl.

9. A compound according to claim 9 wherein R$^5$ is phenyl or phenyl having one or two substituents chosen from the group consisting of lower-alkyl, lower-alkoxy, halogen, hydroxyl, amino, di(lower-alkyl)amino, lower-alkylsulfonamido and lower-acylamino.

10. A compound according to claim 9 wherein, in R$^3$, p is zero, m is one or two, n is one, X is O, S, or SO$_2$ and R$^8$ is phenyl or phenyl having one or two substituents chosen from the group consisting of halogen, lower-alkyl, nitro, hydroxy, lower-alkoxy, lower-alkylamido, lower-alkylsulfonamido, dilower-alkylaminosulfonyl, and amino.

11. A compound according to claim 10 wherein $R^2$ is methyl and m is one.

12. A compound according to claim 11 selected from the group consisting of:
- 4,5-dihydro-3-[(4-methanesulfonamidophenoxy)methyl]-4-methyl-1-phenyl-1H-2,4-benzodiazepine;
- 4,5-dihydro-3-[(4-methanesulfonamidophenoxy)methyl]-4-methyl-1-(4-chlorophenyl)-1H-2,4-benzodiazepine;
- 4,5-dihydro-3-[(4-methanesulfonamidophenoxy)methyl]-4-methyl-1-(4-methoxyphenyl)-1H-2,4-benzodiazepine; and
- 4,5-dihydro-3-[(4-methanesulfonamidophenylsulfonyl)methyl]-4-methyl-1-(4-chlorophenyl)-1H-2,4-benzodiazepine.

13. (+)-4,5-Dihydro-3-[(4-methanesulfonamidophenoxy)methyl]-4-methyl-1-phenyl-1H-2,4-benzodiazepine according to claim 11.

14. A compound according to claim 2 wherein $R^1$ is hydrogen, $R^2$ is lower-alkyl; and $R^4$ is lower-alkyl.

15. A compound according to claim 14 wherein $R^5$ is phenyl or phenyl having one or two substituents chosen from the group consisting of lower-alkyl, lower-alkoxy, halogen, hydroxyl, amino, di-(lower-alkyl) amino, lower-alkylsulfonamido and lower-acylamino.

16. A compound according to claim 15 wherein, in $R^3$, p is zero, m is one or two, n is one, x is O, S, or $SO_2$ and $R^8$ is phenyl or phenyl having one or two substituents chosen from the group consisting of halogen, lower-alkyl, nitro, hydroxy, lower-alkoxy, lower-alkylamido, lower-alkylsulfonamido, dilower-alkylaminosulfonyl, and amino.

17. A compound according to claim 16 wherein $R^2$ and $R^4$ are methyl and m is one.

18. 4,5-Dihydro-3-[(4-methanesulfonamidophenoxy)methyl]-1,4-dimethyl-1-(4-chlorophenyl)-1H-2,4-benzodiazepine according to claim 17.

19. A compound according to claim 1 having the formula:

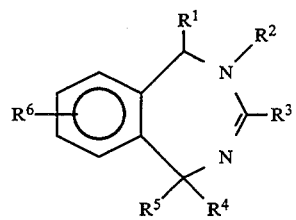

wherein:
$R^1$ is hydrogen; $R^2$ is lower-alkyl or $-CH_2CH_2-$pyridinyl; $R^4$ is hydrogen;
$R^5$ is phenyl or phenyl having one or two substituents chosen from the group consisting of lower-alkyl, lower-alkoxy, halogen, hydroxyl, amino, di(lower-alkyl)amino, lower-alkylsulfonamido, lower-acylamino, lower-alkylthio, and lower-alkylsulfonyl; and
$R^6$ is one or two substituents chosen from the group consisting of hydrogen, lower-alkyl, lower-alkoxy, amino, halogen, nitro and lower-alkylsulfonamido; or $R^6$ is a fused benzene ring.

20. A compound according to claim 19 wherein, in $R^3$, p is zero, m is one or two, n is one, x is O, S, or $SO_2$ and $R^8$ is phenyl or phenyl having one or two substituents chosen from the group consisting of halogen, lower-alkyl, nitro, hydroxy, lower-alkoxy, lower-alkylamido, lower-alkylsulfonamido, dilower-alkylaminosulfonyl, and amino.

21. A compound according to claim 20 wherein $R^2$ is methyl or $CH_2CH_2$-4-pyridinyl, and m is one.

22. 4,5-Dihydro-3-[(4-methanesulfonamidophenoxy)methyl]-4-methyl-1-(4-methylthiophenyl)-1H-2,4-benzodiazepine according to claim 21.

23. A compound according to claim 9 wherein, in $R^3$, p is zero, m is two or three, n is zero and $R^8$ is phenyl or phenyl having one or two substituents chosen from the group consisting of halogen, lower-alkyl, nitro, hydroxy, lower-alkoxy, lower-alkylamido, lower-alkylsulfonamido, dilower-alkylaminosulfonyl, and amino.

24. A compound according to claim 23 wherein m is two and $R^2$ is methyl.

25. 4,5-Dihydro-4-methyl-1-phenyl-3-(2-phenylethyl)-1H-2,4-benzodiazepine according to claim 24.

26. R-(+)-4,5-Dihydro-4-methyl-1-phenyl-3-(2-phenylethyl)-1H-2,4-benzodiazepine according to claim 24.

27. 4,5-Dihydro-1-(4-hydroxyphenyl)-4-methyl-3-(2-phenylethyl)-1H-2,4-benzodiazepine according to claim 24.

28. 4,5-Dihydro-3-[2-(4-hydroxyphenyl)ethyl]-4-methyl-1-phenyl-1H-2,4-benzodiazepine according to claim 24.

29. 4,5-Dihydro-4-methyl-1-(2,4-difluorophenyl)-3-[2-(4-methanesulfonamidophenyl)ethyl]-1H-2,4-benzodiazepine according to claim 24.

30. A compound according to claim 9 wherein, in $R^3$, p and n are both zero and $R^8$ is lower-alkyl.

31. A compound according to claim 30 wherein $R^2$ and $R^8$ are methyl.

32. A compound according to claim 9 wherein, in $R^3$, p is zero, n is one, and X is $-CH=CH-$.

33. 4,5-Dihydro-4-methyl-1-phenyl-3-(2-phenylethenyl)-1H-2,4-benzodiazepine according to claim 32.

34. A compound of formula

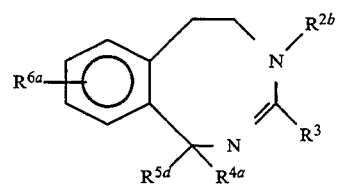

wherein
$R^{2b}$ is hydrogen; lower-alkyl; benzyl; phenyl; or phenyl substituted with halogen, lower-alkyl or lower-alkoxy;
$R^3$ is $Y_p-(CH_2)_m-X_n-R^8$ wherein
Y is $-NH-$, $-O-$, $-S-$, or

p is zero or one;
X is $-S-$, $-O-$, $-SO_2-$,

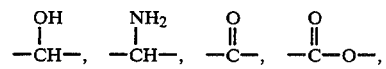

-continued

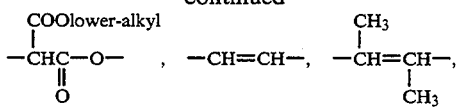

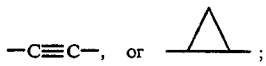

m is an integer from zero to seven;
n is zero or one; and
$R^8$ is hydrogen; lower-alkyl; phenyl; furanyl, thienyl, pyridinyl, phenyl having one or two substituents chosen from the group consisting of halogen, lower-alkyl, nitro, hydroxy, lower-alkoxy, lower-alkylamido, lower-alkylsulfonamido and amino; or when n is zero and m is other than zero, $R^8$ is additionally halogen; benzyl(lower alkyl)amino; di-(lower-alkyl)amino; or X and $R^8$ taken together are cyclohexylidine;
$R^{4a}$ is hydrogen or lower-alkyl;
$R^{5d}$ is lower-alkyl; phenyl; naphthyl; thienyl; pyridinyl; benzyl; or phenyl having one or two substituents chosen from the group consisting of lower-alkyl, lower-alkoxy and halogen;
$R^{6a}$ is one or two substituents chosen independently from the group consisting of hydrogen, lower-alkyl, lower-alkoxy and halogen;
or an acid-addition salt thereof.

35. A compound according to claim 34 wherein $R^{2b}$ is methyl, p is zero, $R^8$ is phenyl or phenyl having one or two substituents chosen from the group consisting of halogen, lower-alkyl, nitro, hydroxy, lower-alkoxy, lower-alkylamido, lower-alkylsulfonamido dilower-alkylamino-sulfonyl, and amino, $R^{4a}$ is hydrogen and $R^{5d}$ is phenyl.

36. 4-Methyl-1-phenyl-3-(2-phenylethyl)-1,4,5,6-tetrahydro-2,4-benzodiazocine according to claim 35.

37. A method for the treatment of cardiac arrhythmia in a patient in need of such treatment which comprises the administration of an antiarrhythmically effective amount of a compound according to claim 1.

38. A method for the treatment of cardiac arrhythmia in a patient in need of such treatment which comprises the administration of an antiarrhythmically effective amount of a compound according to claim 2.

39. A method for the treatment of cardiac arrhythmia in a patient in need of such treatment which comprises the administration of an antiarrhythmically effective amount of a compound according to claim 9.

40. A method for the treatment of cardiac arrhythmia in a patient in need of such treatment which comprises the administration of an antiarrhythmically effective amount of a compound according to claim 13.

41. A method for the treatment of cardiac arrhythmia in a patient in need of such treatment which comprises the administration of an antiarrhythmically effective amount of a compound according to claim 26.

42. A method for the treatment of cardiac arrhythmia in a patient in need of such treatment which comprises the administration of an antiarrhythmically effective amount of a compound according to claim 34.

43. A composition for the treatment of cardiac arrhythmia comprising an antiarrhythmically effective amount of a compound according to claim 1.

44. A composition for the treatment of cardiac arrhythmia comprising an antiarrhythmically effective amount of a compound according to claim 2.

45. A composition for the treatment of cardiac arrhythmia comprising an antiarrhythmically effective amount of a compound according to claim 9.

46. A composition for the treatment of cardiac arrhythmia comprising an antiarrhythmically effective amount of a compound according to claim 13.

47. A composition for the treatment of cardiac arrhythmia comprising an antiarrhythmically effective amount of a compound according to claim 26.

48. A composition for the treatment of cardiac arrhythmia comprising an antiarrhythmically effective amount of a compound according to claim 34.

49. A method for the treatment of cardiac arrhythmia in a patient with impaired ventricular function or congestive heart failure which comprises the administration of an antiarrhythmically effective amount of a compound of the formula:

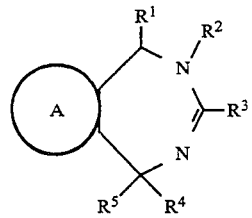

wherein:
A is a ring chosen from the group consisting of phenyl, and phenyl substituted at any available carbon atom by one or two lower-alkylsulfonamido groups;
$R^1$ is hydrogen or phenyl;
$R^2$ is lower-alkyl or $-CH_2CH_2R^{7'}$ wherein $R^{7'}$ is lower-alkoxy, pyridinyl, phenyl or phenyl having one or two lower-alkylsulfonamido substituents;
$R^3$ is $-(CH_2)_m-X_n-R^8$ wherein
m is an integer from zero to seven;
X is $-S-$, $-O-$, $-SO_2-$, $-CH=CH-$, or $-NHSO_2-$;
n is zero or one;
$R^8$ is lower-alkyl, phenyl, pyridinyl, phenyl having one or two substituents chosen independently from the group consisting of halogen, lower-alkyl, lower-alkoxy, lower-alkylsulfonamido, dilower-alkylaminosulfonyl and polyfluorolower-alkylsulfonamido; or pyridinyl having one or two lower-alkyl substituents;
$R^4$ is hydrogen or lower-alkyl; and
$R^5$ is hydrogen, pyridinyl, benzyl, phenyl or phenyl having one or two substituents chosen independently from the group consisting of halogen, lower-alkyl, lower-alkoxy, lower-alkylthio, lower-alkylsulfonyl, lower-alkylsulfonamido, and hydroxy;
or an acid-addition salt thereof; with the proviso that the total number of carbon atoms in $R^1$ plus $R^2$ plus $R^4$ plus $R^5$ must be five or greater; further provided that at least one of $R^2$, $R^3$, $R^5$ or ring A must contain a pyridinyl group, an $-NHSO_2-$ group, or a lower-alkylsulfonamido, dilower-alkylaminosulfonyl, or polyfluorolower-alkylsulfonamido substituent.

50. A method according to claim 49 wherein the compound is of the formula:

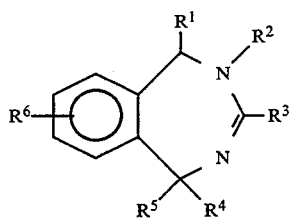

wherein R⁶ is hydrogen, or one or two lower-alkylsulfonamido groups substituted at any available phenyl ring carbon atoms.

51. A method according to claim 50 wherein:
R² is lower-alkyl, or —CH₂CH₂R⁷' wherein R⁷' is lower-alkoxy, pyridinyl, or phenyl having one lower-alkylsulfonamido substituent;
R³ is —(CH₂)ₘ—Xₙ—R⁸ wherein
m is an integer from zero to three;
R⁸ is lower-alkyl, phenyl, 2-, 3-, or 4-pyridinyl, phenyl having one or two substituents chosen independently from the group consisting of halogen, lower-alkyl, lower-alkoxy, lower-alkylsulfonamido, dilower-alkylaminosulfonyl and trifluoromethylsulfonamido; or 2-, 3- or 4-pyridinyl having one lower-alkyl substituent; and
R⁶ is hydrogen, or a lower-alkylsulfonamido group substituted at any available phenyl ring carbon atom.

52. A method according to claim 51 wherein:
R² is methyl, or —CH₂CH₂R⁷' wherein R⁷' is methoxy, 4-pyridinyl, or phenyl having one methylsulfonamido substituent;
R⁸ is lower-alkyl, phenyl, 2-, 3- or 4-pyridinyl, phenyl having one or two substituents chosen independently from the group consisting of halogen, lower-alkyl, lower-alkoxy, lower-alkylsulfonamido, dilower-alkylaminosulfonyl and trifluoromethylsulfonamido; or 2-pyridinyl having one methyl substituent;
R⁴ is hydrogen or methyl;
R⁵ is hydrogen, 4-pyridinyl, benzyl, phenyl or phenyl having one or two substituents chosen independently from the group consisting of halogen, lower-alkyl, lower-alkoxy, lower-alkylthio, lower-alkylsulfonyl, lower-alkylsulfonamido, and hydroxy; and
R⁶ is hydrogen, or a 6- or 8-methylsulfonamido group.

53. A method according to claim 52 wherein the compound is selected from the group consisting of:
4,5-dihydro-3-[(4-methanesulfonamidophenoxy)methyl]-4-methyl-1-phenyl-1H-2,4-benzodiazepine;
4,5-dihydro-3-[(4-methanesulfonamidophenoxy)methyl]-4-methyl-1-(4-chlorophenyl)-1H-2,4-benzodiazepine;
4,5-dihydro-3-[(4-methanesulfonamidophenoxy)methyl]-4-methyl-1-(4-methoxyphenyl)-1H-2,4-benzodiazepine;
4,5-dihydro-3-[(4-methanesulfonamidophenylsulfonyl)methyl]-4-methyl-1-(4-chlorophenyl)-1H-2,4-benzodiazepine;
4,5-dihydro-3-[(4-methanesulfonamidophenoxy)methyl]-4-methyl-1-(4-methylthiophenyl)-1H-2,4-benzodiazepine; and
4,5-dihydro-4-methyl-1-(2,4-difluorophenyl)-3-[2-(4methanesulfonamidophenyl)ethyl]-1H-2,4-benzodiazepine.

54. A method according to claim 52 wherein the compound is (+)-4,5-Dihydro-3-[(4-methanesulfonamidophenoxy)methyl]-4-methyl-1-phenyl-1H-2,4-benzodiazepine.

55. A composition for the treatment of cardiac arrhythmia in a patient with impaired ventricular function or congestive heart failure which comprises an antiarrhythmically effective amount of a compound of the formula:

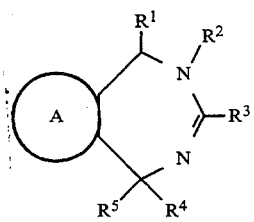

wherein:
A is a ring chosen from the group consisting of phenyl, and phenyl substituted at any available carbon atom by one or two lower-alkylsulfonamido groups;
R¹ is hydrogen or phenyl;
R² is lower-alkyl or —CH₂CH₂R⁷' wherein R⁷' is lower-alkoxy, pyridinyl, phenyl or phenyl having one or two lower-alkylsulfonamido substituents;
R³ is —(CH₂)ₘ—Xₙ—R⁸ wherein
m is an integer from zero to seven;
X is —S—, —O—, —SO₂—, —CH=CH—, or —NHSO₂—;
n is zero or one;
R⁸ is lower-alkyl, phenyl, pyridinyl, phenyl having one or two substituents chosen independently from the group consisting of halogen, lower-alkyl, lower-alkoxy, lower-alkylsulfonamido, dilower-alkylaminosulfonyl and polyfluorolower-alkylsulfonamido; or pyridinyl having one or two lower-alkyl substituents;
R⁴ is hydrogen or lower-alkyl; and
R⁵ is hydrogen, pyridinyl, benzyl, phenyl or phenyl having one or two substituents chosen independently from the group consisting of halogen, lower-alkyl, lower-alkoxy, lower-alkylthio, lower-alkylsulfonyl, lower-alkylsulfonamido, and hydroxy;

or an acid-addition salt thereof; together with a pharmaceutically acceptable vehicle, adjuvant or excipient; with the proviso that the total number of carbon atoms in R¹ plus R² plus R⁴ plus R⁵ must be five or greater; further provided that at least one of R², R³, R⁵ or ring A must contain a pyridinyl group, an —NHSO₂— group, or a lower-alkylsulfonamido, dilower-alkylaminosulfonyl, or poly-fluorolower-alkylsulfonamido substituent.

56. A composition according to claim 55 wherein the compound is of the formula:

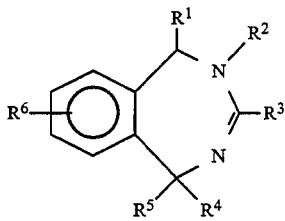

wherein R⁶ is hydrogen, or one or two lower-alkylsulfonamido groups substituted at any available phenyl ring carbon atoms.

57. A composition according to claim 56 wherein:
R² is lower-alkyl, or —CH₂CH₂R⁷' wherein R⁷' is lower-alkoxy, pyridinyl, or phenyl having one lower-alkylsulfonamido substituent;
R³ is —(CH₂)$_m$—X$_n$—R⁸ wherein
m is an integer from zero to three;
R⁸ is lower-alkyl, phenyl, 2-, 3-, or 4-pyridinyl, phenyl having one or two substituents chosen independently from the group consisting of halogen, lower-alkyl, lower-alkoxy, lower-alkylsulfonamido, dilower-alkylaminosulfonyl and trifluoromethylsulfonamido; or 2-, 3- or 4-pyridinyl having one lower-alkyl substituent; and
R⁶ is hydrogen, or a lower-alkylsulfonamido group substituted at any available phenyl ring carbon atom.

58. A composition according to claim 57 wherein:
R² is methyl, or —CH₂CH₂R⁷' wherein R⁷' is methoxy, 4-pyridinyl, or phenyl having one methylsulfonamido substituent;
R⁸ is lower-alkyl, phenyl, 2-, 3- or 4-pyridinyl, phenyl having one or two substituents chosen independently from the group consisting of halogen, lower-alkyl, lower-alkoxy, lower-alkylsulfonamido, dilower-alkylaminosulfonyl and trifluoromethylsulfonamido; or 2-pyridinyl having one methyl substituent;
R⁴ is hydrogen or methyl;
R⁵ is hydrogen, 4-pyridinyl, benzyl, phenyl or phenyl having one or two substituents chosen independently from the group consisting of halogen, lower-alkyl, lower-alkoxy, lower-alkylthio, lower-alkylsulfonyl, lower-alkylsulfonamido, and hydroxy; and
R⁶ is hydrogen, or a 6- or 8-methylsulfonamido group.

59. A composition according to claim 58 wherein the compound is selected from the group consisting of:
4,5-dihydro-3-[(4-methanesulfonamidophenoxy)methyl]-4-methyl-1-phenyl-1H-2,4-benzodiazepine;
4,5-dihydro-3-[(4-methanesulfonamidophenoxy)methyl]-4-methyl-1-(4-chlorophenyl)-1H-2,4-benzodiazepine;
4,5-dihydro-3-[(4-methanesulfonamidophenoxy)methyl]-4-methyl-1-(4-methoxyphenyl)-1H-2,4-benzodiazepine;
4,5-dihydro-3-[(4-methanesulfonamidophenylsulfonyl)methyl]-4-methyl-1-(4-chlorophenyl)-1H-2,4-benzodiazepine;
4,5-dihydro-3-[(4-methanesulfonamidophenoxy)methyl]-4-methyl-1-(4-methylthiophenyl)-1H-2,4-benzodiazepine; and
4,5-dihydro-4-methyl-1-(2,4-difluorophenyl)-3-[2-(4methanesulfonamidophenyl)ethyl]-1H-2,4-benzodiazepine.

60. A composition according to claim 58 wherein the compound is (+)-4,5-Dihydro-3-[(4-methanesulfonamidophenoxy)methyl]-4-methyl-1-phenyl-1H-2,4-benzodiazepine.

\* \* \* \* \*